US012616232B2

(12) United States Patent
Brandhorst et al.

(10) Patent No.: US 12,616,232 B2
(45) Date of Patent: May 5, 2026

(54) FASTING MIMICKING DIET

(71) Applicant: UNIVERSITY OF SOUTHERN CALIFORNIA, Los Angeles, CA (US)

(72) Inventors: Sebastian Brandhorst, Redondo Beach, CA (US); Valter D. Longo, Playa del Rey, CA (US); Min Wei, West Covina, CA (US); Fabrizio Schirano, Plano, TX (US)

(73) Assignee: University of Southern California, Los Angeles, CA (US)

( * ) Notice: Subject to any disclaimer, the term of this patent is extended or adjusted under 35 U.S.C. 154(b) by 770 days.

(21) Appl. No.: 17/009,382

(22) Filed: Sep. 1, 2020

(65) Prior Publication Data

US 2021/0137149 A1       May 13, 2021

Related U.S. Application Data

(63) Continuation of application No. 15/432,803, filed on Feb. 14, 2017, now Pat. No. 11,284,640.

(51) Int. Cl.
| | |
|---|---|
| *A23L 33/00* | (2016.01) |
| *A23F 3/40* | (2006.01) |
| *A23L 2/38* | (2021.01) |
| *A23L 2/52* | (2006.01) |
| *A23L 19/00* | (2016.01) |
| *A23L 23/00* | (2016.01) |
| *A23L 23/10* | (2016.01) |
| *A23L 25/00* | (2016.01) |
| *A23L 33/115* | (2016.01) |
| *A23L 33/15* | (2016.01) |
| *A23L 33/155* | (2016.01) |
| *A23L 33/16* | (2016.01) |
| *A61K 36/00* | (2006.01) |

(52) U.S. Cl.
CPC ............... *A23L 33/40* (2016.08); *A23F 3/40* (2013.01); *A23L 2/38* (2013.01); *A23L 2/52* (2013.01); *A23L 19/05* (2016.08); *A23L 23/00* (2016.08); *A23L 23/10* (2016.08); *A23L 25/30* (2016.08); *A23L 33/115* (2016.08); *A23L 33/15* (2016.08); *A23L 33/155* (2016.08); *A23L 33/16* (2016.08); *A23L 33/30* (2016.08); *A61K 36/00* (2013.01); *A23V 2002/00* (2013.01)

(58) Field of Classification Search
CPC .......... A23L 19/05; A23L 23/10; A23L 33/30; A23L 33/115; A23L 33/16; A23L 15/00; A23L 23/00; A23L 33/155; A23L 2/52; A23L 33/40; A23F 3/40; A61K 36/00; A23V 2002/00
USPC ..... 426/648, 72, 73, 74, 615, 108, 112, 580, 426/549
See application file for complete search history.

(56) References Cited

U.S. PATENT DOCUMENTS

| | | | | |
|---|---|---|---|---|
| 5,595,772 | A | * | 1/1997 | Wurtman ................ A23L 35/00 426/810 |
| 5,977,059 | A | * | 11/1999 | Khoo ...................... A23L 33/21 514/19.5 |
| 6,413,545 | B1 | | 7/2002 | Alviar et al. |
| 7,790,670 | B2 | | 9/2010 | Ward et al. |
| 8,211,700 | B2 | | 7/2012 | Longo |
| 8,728,815 | B2 | | 5/2014 | Longo |
| 8,865,646 | B2 | | 10/2014 | Longo |
| 8,924,239 | B1 | | 12/2014 | Kurple |
| 9,237,761 | B2 | | 1/2016 | Longo et al. |
| 9,386,790 | B2 | | 7/2016 | Longo et al. |
| 10,015,980 | B2 | | 7/2018 | Longo et al. |
| 10,052,516 | B1 | | 8/2018 | Lin |
| 10,172,839 | B2 | | 1/2019 | Longo et al. |
| 10,246,446 | B2 | | 4/2019 | Longo et al. |
| 10,433,576 | B2 | | 10/2019 | Longo et al. |
| 10,660,932 | B2 | | 5/2020 | Longo et al. |
| 10,821,177 | B2 | | 11/2020 | Longo |
| 2011/0118528 | A1 | | 5/2011 | Longo et al. |
| 2012/0301559 | A1 | | 11/2012 | Pridmore-Merten et al. |
| 2013/0045215 | A1 | | 2/2013 | Longo et al. |
| 2013/0261183 | A1 | | 10/2013 | Bhagat |
| 2013/0316948 | A1 | | 11/2013 | Longo |
| 2014/0328863 | A1 | | 11/2014 | Longo |
| 2015/0133370 | A1 | | 5/2015 | Longo |
| 2016/0303056 | A1 | | 10/2016 | Longo et al. |

(Continued)

FOREIGN PATENT DOCUMENTS

| | | |
|---|---|---|
| JP | 2009-263307 | 11/2009 |
| JP | 2013-539454 | 10/2013 |

(Continued)

OTHER PUBLICATIONS

Ramesh, B., "Dietary Management of Pancreatic Beta-Cell Homeostasis and Control of Diabetes," Medical Hypotheses, (1996) 46, 357-361 (Year: 1996).*
Japanese Journal of Medicine and Pharmaceutical Science, Feb. 2007, v. 57, n. 2, pp. 141-145 (in Japanese).
Office Action dated Nov. 16, 2021 for Japanese Appn. No. 2019-564381, 3 pgs. (in Japanese).
Anonymous: "PROLON", Feb. 5, 2017 retrieved from Internet: URL: http://web.archive.org/web/20170205183548/http:/l-nutra.com/prolon/, 4 pgs.

(Continued)

*Primary Examiner* — Jeffrey P Mornhinweg
(74) *Attorney, Agent, or Firm* — Brooks Kushman P.C.

(57) ABSTRACT

A fasting mimicking diet package providing daily meal portions for a predetermined number of days is provided. The fasting mimicking diet package includes a kale cracker composition, a first vegetable broth composition, a mushroom soup composition, a tomato soup composition, a quinoa-containing minestrone soup composition, a bean-containing minestrone soup composition, and a pumpkin soup composition. Characteristically, the daily meal portions are packaged into meal servings or into a total daily serving to be divided into meals.

14 Claims, 48 Drawing Sheets

(56) References Cited

U.S. PATENT DOCUMENTS

| | | |
|---|---|---|
| 2016/0324193 A1 | 11/2016 | Longo et al. |
| 2016/0331016 A1 | 11/2016 | Longo et al. |
| 2017/0027217 A1 | 2/2017 | Longo et al. |
| 2017/0035093 A1 | 2/2017 | Longo et al. |
| 2017/0035094 A1 | 2/2017 | Longo et al. |
| 2017/0325493 A1 | 11/2017 | Longo et al. |
| 2018/0228198 A1 | 8/2018 | Longo et al. |
| 2019/0029301 A1 | 1/2019 | Longo et al. |
| 2019/0276445 A1 | 9/2019 | Longo et al. |
| 2019/0285640 A1 | 9/2019 | Longo |
| 2020/0029614 A1 | 1/2020 | Longo et al. |

FOREIGN PATENT DOCUMENTS

| | | |
|---|---|---|
| JP | 2015-535177 | 2/2015 |
| WO | 02-071874 A2 | 9/2002 |
| WO | 2012/007516 A1 | 1/2012 |
| WO | 2014/060555 A1 | 4/2014 |
| WO | 2016/179466 | 11/2016 |

OTHER PUBLICATIONS

Brandhorst, S. et al., "A Periodic Diet that Mimics Fasting Promotes Multi-System Regeneration, Enhanced Cognitive Performance, and Healthspan," Cell Metabolism, v. 22, n. 1, Jul. 1, 2015, pp. 86-99.
European Office Action dated Mar. 15, 2021 for EP 18754069.5, 13 pgs.
Spindler, S.R., "Caloric Restriction: From Soups to Nuts," Ageing Research Reviews, v. 9, n. 3, Jul. 1, 2010, pp. 324-353.
"Green Tea-Scented Quinoa with Corn, Delicious Living," 2003, http://deliciousliving.com/recipes/green-tea-scented-quinoa-com, pp. 1-4.
Hosie, R. "Fasting mimicking: the scientific new diet that's making people lose half a stone in five days," The Indepdnent, https://www.independent.co.uk/life-style/health-and-families/prolong-fasting-mmicking-diet-weight-loss-natural-plant-based-a7518081.html, Jan. 10, 2017, pp. 1-11.
Lambert, V., "Forget the fast diet—and try the fast mimicking diet", The Telegraph, https://www.telegraph.co.uk/lifestyle/welbeing/diet/11776466/Forget-the-Fast-Diet-and-try-the-Fast-Mimicking-Diet . . . html, Aug. 2, 2015, pp. 1-5.
Final Office Action dated Jul. 27, 2018 for U.S. Appl. No. 15/432,803, filed Feb. 14, 2017, 11 pgs.
Final Office Action dated Aug. 29, 2019 for U.S. Appl. No. 15/432,803, filed Feb. 14, 2017, 10 pgs.
Office Action dated Feb. 25, 2019 for U.S. Appl. No. 15/432,803, filed Feb. 14, 2017, 9 pgs.
Office Action dated Mar. 13, 2020 for U.S. Appl. No. 15/432,803, filed Feb. 14, 2017, 9 pgs.
Office Action dated Mar. 15, 2018 for U.S. Appl. No. 15/432,803, filed Feb. 14, 2017, 23 pgs.
Office Action dated Aug. 27, 2020 for U.S. Appl. No. 15/432,803, filed Feb. 14, 2017, 11 pgs.
Office Action dated May 28, 2021 for U.S. Appl. No. 15/432,803, 14 pgs.

* cited by examiner

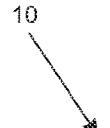
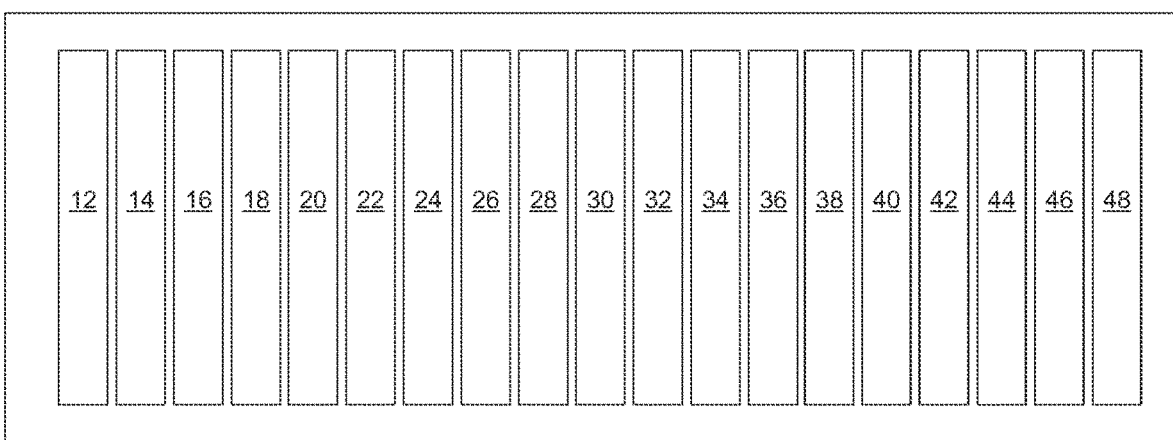
Fig. 1A

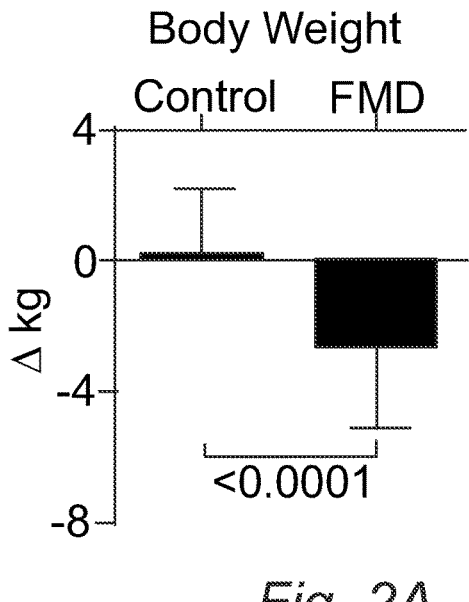
*Fig. 2A*
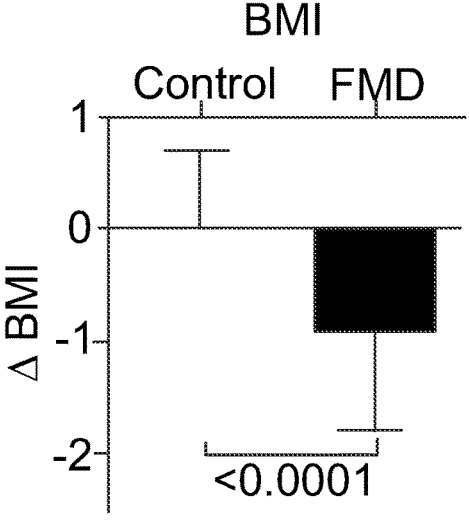
*Fig. 2B*
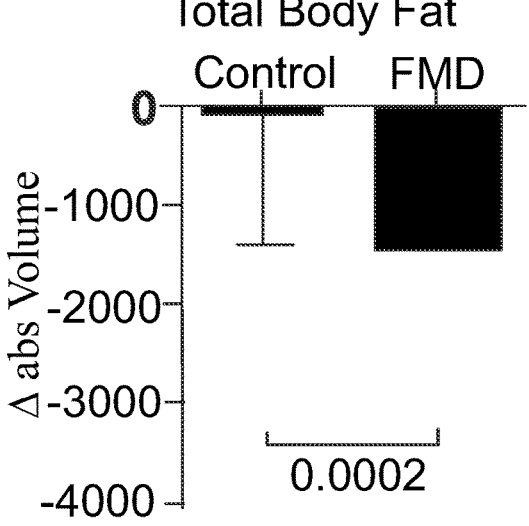
*Fig. 2C*
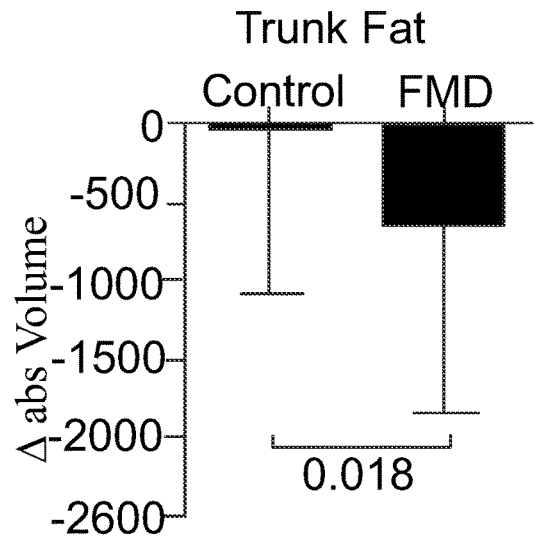
*Fig. 2D*

Lean Body Mass

Circumference glucose

IGF-1

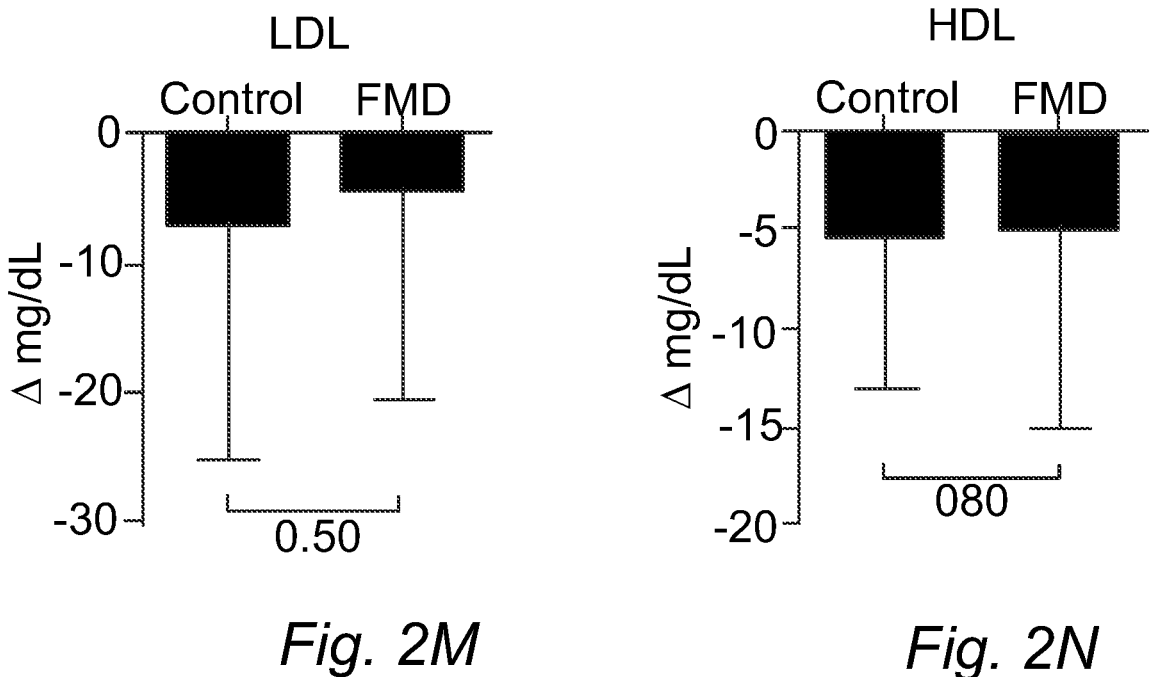
*Fig. 2M*                       *Fig. 2N*
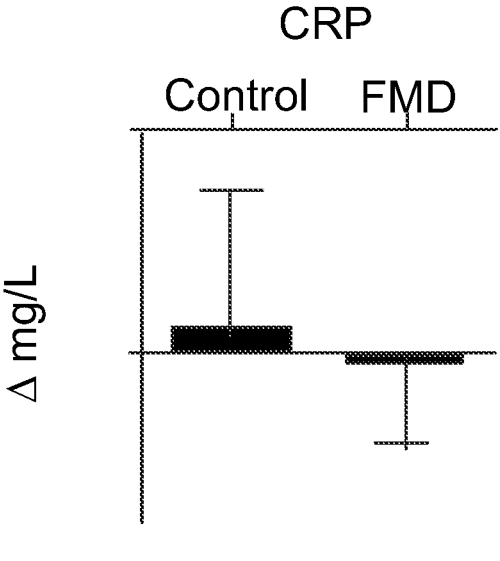
*Fig. 2O*

Glucose

Triglycerides

Total Cholesterol

LDL (>199 Cholesterol)

HDL

CRP

A) BMI
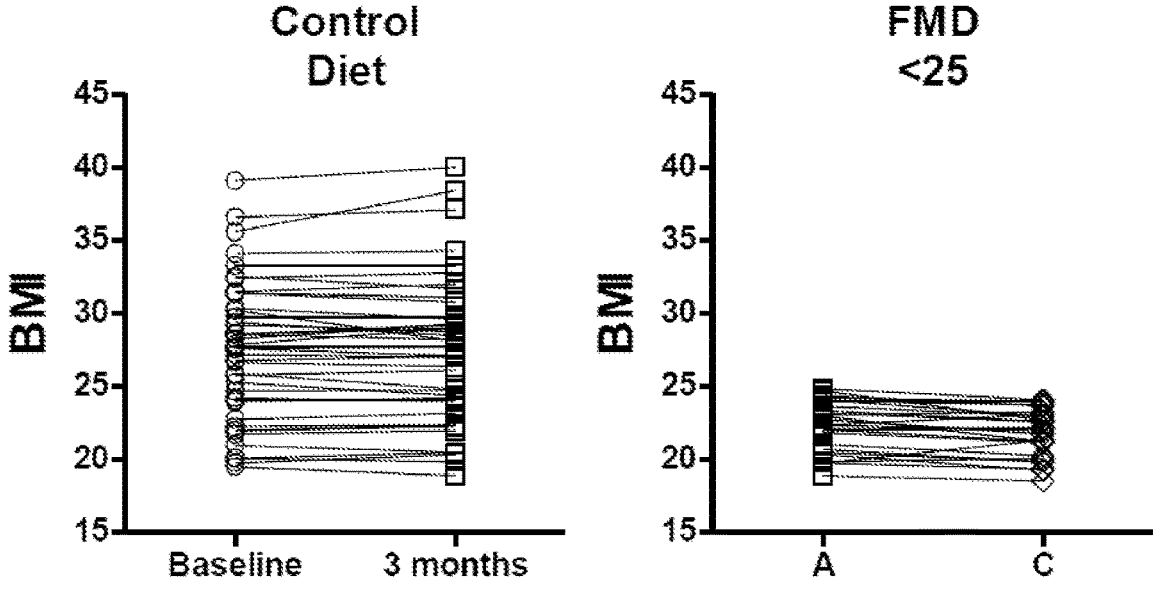
*Fig. 6A-1*        *Fig. 6A-2*
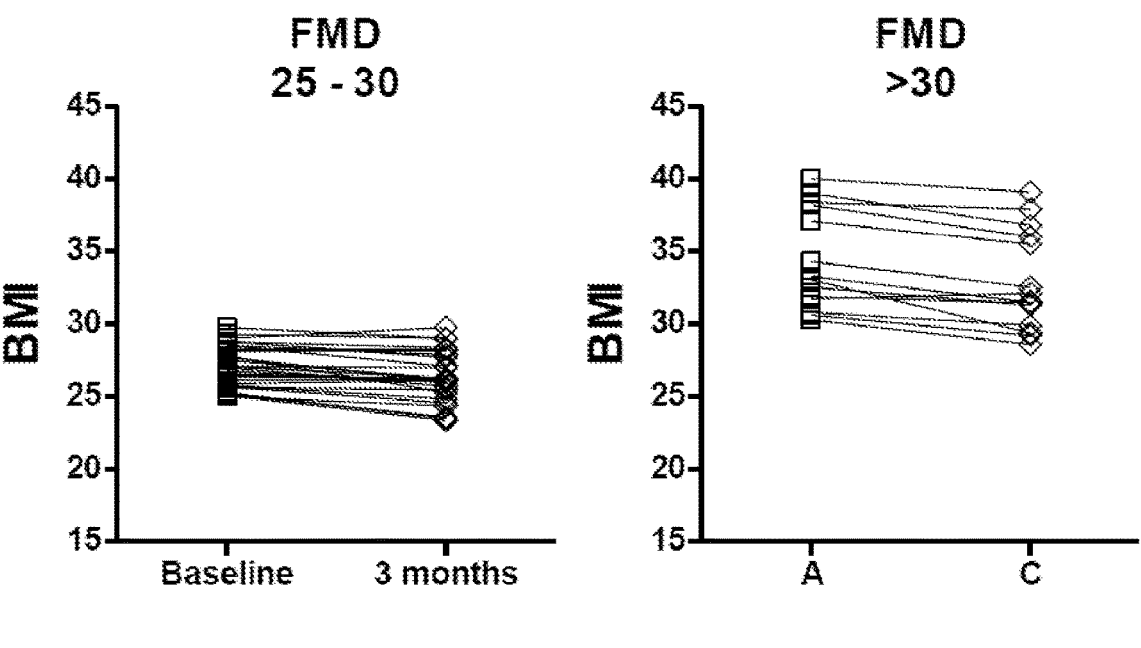
*Fig. 6A-3*        *Fig. 6A-4*

B) Systolic Blood Pressure

C) Diastolic Blood Pressure

Fig. 6C-1                    Fig. 6C-2

D) Fasting Glucose

E) IGF-1

F) Triglycerides

G) Total Cholesterol

H) LDL

I) HDL
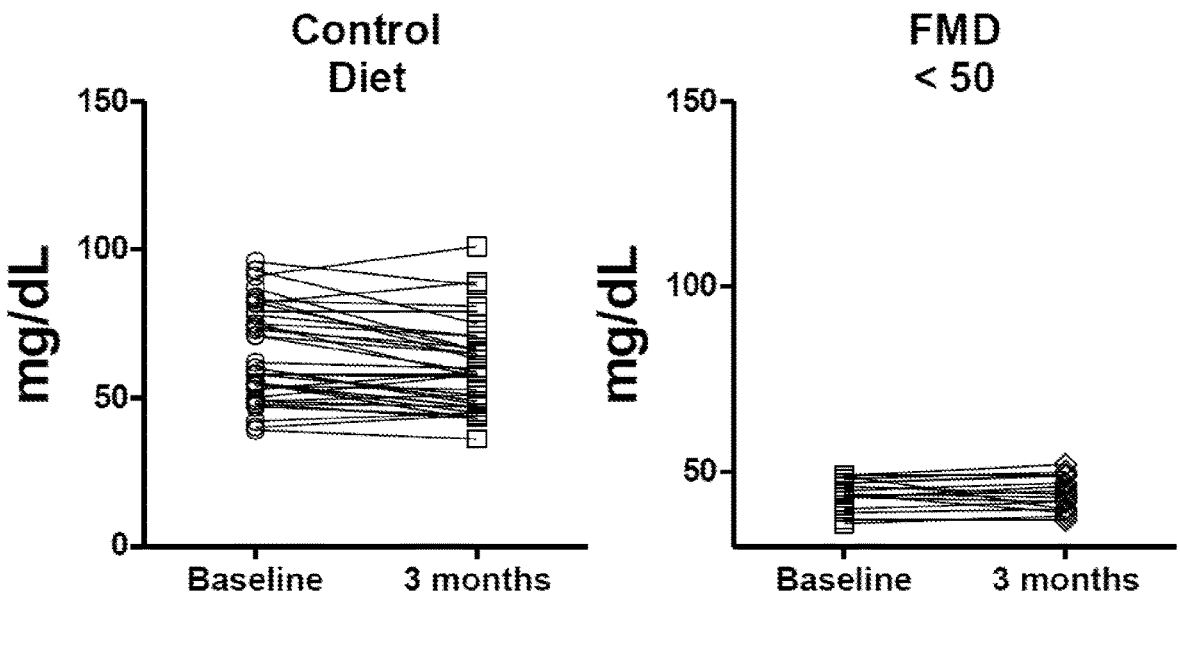
Fig. 6I-1
Fig. 6I-2
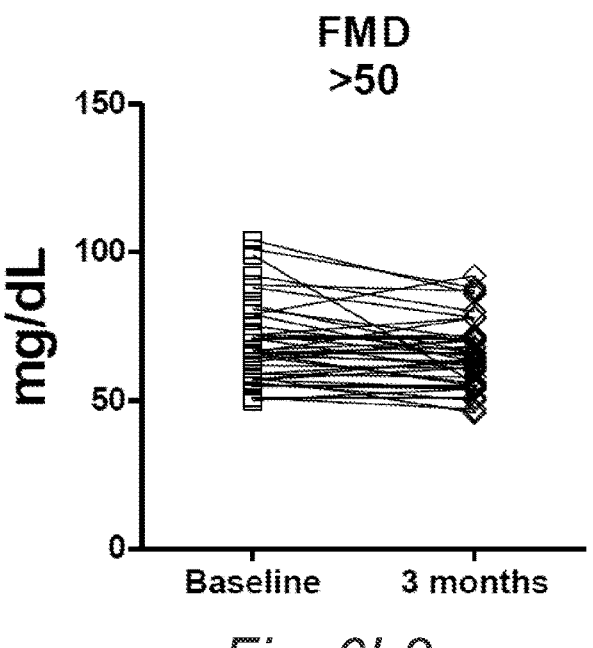
Fig. 6I-3

SOUPS

Vegetable Soup Mix

INGREDIENTS: Rice Flour, Dried Onion, Inulin (Chicory Fiber), Dried Tomato, Dried Carrot, Salt, Dried Red Pepper, Dried Leek, Potato Starch, Olive Oil, Freeze Dried Basil, Spinach Powder, Dried Parsley, Natural Flavor

Nutrition Facts

Serving Size 1.2 oz (33g); (10 fl oz Prepared)

Servings Per Package 1

Amount Per Serving

Calories          100

Calories from Fat 20

| | | % Daily Value* |
|---|---|---|
| Total Fat | 2 g | 3% |
| Saturated Fat | 1 g | 5% |
| Trans Fat | 0 g | |
| Cholesterol | 0 mg | |
| Sodium | 650 mg | 27% |
| Total Carbohydrate | 19 g | 6% |
| Dietary Fiber | 5 g | 20% |
| Sugars | 5 g | |
| Proteins | 2 g | |
| Vitamin A (RAE) | | 45% |
| Vitamin C | | 45% |
| Calcium | | 4% |
| Iron | | 6% |

* Percent Daily Values are based on a 2,000 calorie diet.

*Fig. 7A*

SOUPS

Mushroom Soup Mix

INGREDIENTS: Rice Flour, Carrot Powder, Dried Onion, Champignon Mushroom Powder, Inulin (Chicory Fiber), Dried Champignon Mushroom, Salt, Yeast Extract, Potato Starch, Olive Oil, Dried Parsley, Natural Flavor Nutrition Facts Serving Size 1.2 oz (33g); (10 fl oz Prepared)

Servings Per Package 1

| Amount Per Serving | | % Daily Value* |
|---|---|---|
| Calories | 100 | |
| Calories from Fat 20 | | |
| Total Fat | 2 g | 3% |
| Saturated Fat | 1 g | 5% |
| Trans Fat | 0 g | |
| Cholesterol | 0 mg | |
| Sodium | 910 mg | 38% |
| Total Carbohydrate | 18 g | 6% |
| Dietary Fiber | 4 g | 16% |
| Sugars | 9 g | |
| Proteins | 3 g | |
| Vitamin A (RAE) | | 90% |
| Vitamin C | | 4% |
| Calcium | | 2% |
| Iron | | 2% |

* Percent Daily Values are based on a 2,000 calorie diet.

*Fig. 7B*

SOUPS

Tomato Soup Mix

INGREDIENTS: Rice Flour, Dried Tomato Powder, Dried Onion, Inulin (Chicory Fiber), Potato Starch, Dried Tomato Pieces, Olive Oil, Salt, Yeast Extract, Dried Basil, Dried Parsley, Natural Flavor Nutrition Facts Serving Size 1.2 oz (33g); (10 fl oz Prepared)

Servings Per Package 1

Amount Per Serving

Calories    110

Calories from Fat 10

| | | % Daily Value* |
|---|---|---|
| Total Fat | 1 g | 1% |
| Saturated Fat | 0 g | 0% |
| Trans Fat | 0 g | |
| Cholesterol | 0 mg | |
| Sodium | 800 mg | 33% |
| Total Carbohydrate | 25 g | 8% |
| Dietary Fiber | 6 g | 24% |
| Sugars | 6 g | |
| Proteins | 3 g | |
| Vitamin A (RAE) | | 0% |
| Vitamin C | | 6% |
| Calcium | | 10% |
| Iron | | 10% |

* Percent Daily Values are based on a 2,000 calorie diet.

*Fig. 7C*

Energy Drink Mix

INGREDIENTS: Purified Water, Natural Vegetable Glycerin, Polylysine (Natural Preservative).

Nutrition Facts

Serving Size 0.6 fl oz (17mL)

Servings Per Package 4

| Amount Per Serving | |
| --- | --- |
| | % Daily Values* |
| Calories 20 | |
| Total Fat 0g | 0% |
| Sodium 0g | 0% |
| Total Carbohydrate 5g | 2% |
| Proteins 0g | |

Not a significant source of fat, cholesterol, fiber, sugars, vitamin A, vitamin C, calcium and iron.

*Percent Daily Values (DV) are based on a 2,000 calorie diet.

Fig. 7D

Energy Bar

INGREDIENTS: Almond Meal, Macadamia Nut Butter, Honey, Pecan, Coconut, Flaxseed Meal, Coconut Oil, Vanilla, Sea Salt.

Nutrition Facts

Serving Size 1.6 oz (45g)

Serving Per Package 1

Amount Per Serving

Calories    270

Calories from Fat 200

| | | % Daily Value* |
|---|---|---|
| Total Fat | 23 g | 35% |
| Saturated Fat | 4.5 g | 24% |
| Trans Fat | 0 g | |
| Cholesterol | 0 mg | |
| Sodium | 350 mg | 15% |
| Total Carbohydrate | 13 g | 4% |
| Dietary Fiber | 3 g | 13% |
| Sugar | 8 g | |
| Proteins | 5 g | |
| Calcium | | 4% |
| Iron | | 14% |

Not a significant source of vitamin A and vitamin C.

* Percent Daily Values are based on a 2,000 calorie diet.

*Fig. 7E*

Chip Snack

INGREDIENTS: Kale, Red Bell Peppers, Cashews, Sunflower Seeds, Nutritional Yeast, Lemon Juice, Cayenne Pepper, Sea Salt

Nutrition Facts

Serving Size 1.05 oz (30g)

Serving Per Package 1

Amount Per Serving

Calories    160

Calories from Fat 110

| | | % Daily Value* |
|---|---|---|
| Total Fat | 11 g | 17% |
| Saturated Fat | 1 g | 5% |
| Trans Fat | 0 g | |
| Cholesterol | 0 mg | |
| Sodium | 190 mg | 8% |
| Total Carbohydrate | 13 g | 4% |
| Dietary Fiber | 4 g | 16% |
| Sugar | 1 g | |
| Proteins | 7 g | |
| Vitamin A (RAE) | | 60% |
| Vitamin C | | 40% |
| Calcium | | 8% |
| Iron | | 15% |

Not a significant source of vitamin A and vitamin C.

* Percent Daily Values are based on a 2,000 calorie diet.

*Fig. 7F*

Algal Oil

INGREDIENTS: Gelatin, Glycerin, Purified Water, Turmeric (Color), Annatto Extract (Color)

Nutrition Facts

Serving Size 1 Softgel

| Amount Per Serving | % Daily Values* |
|---|---|
| Calories 6 | |
| Calories from Fat 5 | |
| Total Fat 0.5g | < 1% |
| Sodium 0g | 0% |
| Total Carbohydrate 0g | 0% |
| Proteins 0g | |
| DHA Omega-3 (from Algal Oil) 200 mg** | |

*Percent Daily Values (DV) are based on a 2,000 calorie diet.

**Daily value not established.

*Fig. 7G*

NR-1
Vegetable Powder with Vitamins and Minerals Supplements

OTHER INGREDIENTS: Stearic Acid, Microcrystalline Cellulose, Dicalcium Phosphate, Croscarmellose Sodium, Magnesium Stearate, Silicone Dioxide, Food-grade Shellac Nutrition Facts
Serving Size 1 Tablet
Servings Per Container: 2

| Amount per Serving | | % Daily Value* |
|---|---|---|
| Vitamin A (as Beta Carotene) | 1,250 IU | 25% |
| Vitamin C (Ascorbic Acid) | 15 mg | 25% |
| Vitamin D (as Cholecalciferol) | 100 IU | 25% |
| Vitamin E (as DL-Alpha Tocopherol Acetate) | 7.5 IU | 25% |
| Vitamin K (as Phytonadione) | 20 mcg | 25% |
| Thiamine (as Thiamine Mononitrate) | 0.37 mg | 25% |
| Riboflavin | 0.42 mg | 25% |
| Niacin (as Niacinamide) | 5 mg | 25% |
| Vitamin B6 (as Pyridoxine HCl) | 0.5 mg | 25% |
| Folic Acid | 100 mcg | 25% |
| Vitamin B12 (as Cyanocobalamin) | 1.5 mcg | 25% |
| Biotin | 15 mcg | 5% |
| Pantothenic Acid (as Calcium-D-Pantothenate) | 2.5 mg | 25% |
| Calcium (as Calcium Carbonate and Tribasic Calcium Phosphate) | 100 mg | 10% |
| Iron (as Ferrous Fumarate) | 4.5 mg | 25% |
| Phosphorous (as Tribasic Calcium Phosphate) | 10 mg | 1% |
| Iodine (as Potassium Iodine) | 37.5 mcg | 25% |
| Magnesium (as Magnesium Oxide) | 26 mg | 7% |
| Zinc (Zinc Oxide) | 3.75 mg | 25% |
| Selenium (as Sodium Selenate) | 7.5 mcg | 11% |
| Copper (as Cupric Sulfate) | 0.25 mg | 13% |
| Manganese (as Manganese Sulfate) | 0.5 mg | 25% |
| Chromium (as Chromium Picolinate) | 17.4 mcg | 15% |
| Molybdenum (as Sodium Molybdate) | 18.75 mcg | 25% |
| L-Nutra Power Blend (Beet Root, Spinach Leaf, Tomato Fruit, Carrot Root, Collard Leaf, Kale Leaf) | 600 mg | ** |

* Percent Daily Values are based on a 2,000 calorie diet.
** Daily Values not established.

*Fig. 7H*

| Table 1.Baseline Characteristics of Subjects * | | |
|---|---|---|
| Characteristics | Arm 1 (N=48) | Arm 2 (N=52) |
| Sex – no. of subjects (%) | | |
| Male | 18 (37.5) | 19 (35.5) |
| Female | 30 (62.5) | 33 (63.5) |
| Race or ethnic group-no. of subjects (%)[†] | | |
| White | 26 (54.2) | 25 (48.1) |
| Black | 2 (4.2) | 5 (9.6) |
| Hispanic | 13 (27.1) | 14 (26.9) |
| Asian | 6 (12.5) | 7(13.5) |
| Other | 1 (2.1) | 1 (1.9) |
| Age (years) | 42.2 ± 12.5 | 43.3 ± 11.7 |
| Weight (kg) | 77.0 ± 15.9 | 74.3 ± 16.6 |
| Education (years) | 16.7 ± 2.8 | 16.6 ± 2.3 |
| Smoking Status – no. of subjects (%)[†] | | |
| Never smoked | 29 (60.4) | 39 (75.0) |
| Former smoker | 13 (27.1) | 9 (17.3) |
| Current smoker | 6 (12.5) | 4 (7.7) |
| Body-mass Index[‡] | | |
| Mean | 27.8 ± 5.1 | 26.6 ± 4.9 |
| < 25 - no. of subjects (%) | 17 (35.4) | 20 (38.4) |
| 25- 30 - no. of subjects (%) | 18 (37.5) | 21 (40.4) |
| > 30 - no. of subjects (%) | 13 (27.1) | 11 (21.2) |
| Systolic blood pressure (mm Hg) | 117.2 ± 12.3 | 117.2 ± 13.0 |
| Diastolic blood pressure (mm Hg) | 75.6 ± 9.2 | 75.2 ± 7.8 |
| Triglycerides (mg/dL) | 104.0 ± 64.6 | |
| Cholesterol (mg/dL) | | |
| Total | 197.5 ± 39.6 | 185.7 ± 36.6 |
| Low-density lipoprotein | 114.5 ± 36.1 | 110.3 ± 61.6 |
| High-density lipoprotein | 62.2 ± 16.4 | 65.2 ± 18.1 |

*Plus-minus values are mean± SD rounded to the nearest tenth.*

*† The race or ethnic group was assigned by the subjects themselves.*
*‡ The body-mass index is the weight in kliograms divided by the square of the height in meters.*

*Fig. 8*

Table 2. Study Arm -specific Biomarkers of Adherence and Changes in Risk Factors

| Variable | N= | Baseline Mean ± SD (95%CI) | CTRL: 3 months after Baseline FMD: 5 Days After 3rd FMD Cycle Mean ± SD (95%CI) | p-value§ | Difference:∆* | Efficacy (comparing Δ) p-value* |
|---|---|---|---|---|---|---|
| Body Weight (kg) | | | | | | |
| Control Diet, Arm 1 | 43 | 77.2±15.6 (72.1-82.2) | 77.3±17.0 (72.0-82.5) | 0.72 | 0.1 ±2.1 | <0.0001** |
| FMD, Arm 2 | 39 | 74.1±15.5 (69.3– 78.9) | 71.6±14.6 (67.0-76.1) | <0.0001 | -2.5±2.5 | |
| Body-mass Index‡ | | | | | | |
| Control Diet, Arm 1 | 43 | 27.4±4.8 (25.9-28.9) | 27.4±5.0 (25.9-28.9) | 0.82 | 0.00±0.7 | <0.0001** |
| FMD, Arm 2 | 39 | 26.2±4.4 (24.8-27.6) | 25.3±4.3 (24.0-26.5) | <0.0001 | -0.9±0.9 | |
| **Total Body Fat* (abs.Volume)** | | | | | | |
| Control Diet, Arm 1 | 43 | 23651±8155 (21142-26161) | 23607±8337 (21041-26173) | 0.83 | -44±1365 | 0.0002** |
| FMD, Arm 2 | 38 | 20643±8459 (17953-23332) | 19249±7792 (16772-21726) | <0.0001 | -1393±1786 | |
| **Trunk Fat* (abs. Volume)** | | | | | | |
| Control Diet, Arm 1 | 43 | 8429±4742 (6969-9888) | 8395±4776 (6925-9865) | 0.83 | -33±1046 | 0.18 |
| FMD, Arm 2 | 38 | 6573±4877 (5022-8124) | 5938±4295 (4572-7303) | 0.0023 | -636±1198 | |
| **Lean Body Mass* (rel. Volume %)** | | | | | | |
| Control Diet, Arm 1 | 43 | 63.9±8.2 (61.4-66.4) | 64.0±8.7 (61.3-66.7) | 0.64 | 0.1±1.5 | 0.70 |
| FMD, Arm 2 | 38 | 66.8±9.6 (63.7-69.8) | 67.6±9.4 (64.6-70.6) | 0.016 | 0.8±2.0 | |
| Waist Circumference (cm) | | | | | | |
| Control Diet, Arm 1 | 28 | 95.4±14.2 (89.9-100.9) | 94.6±14.5 (88.9-100.2) | 0.10 | -0.8±25 | 0.0035** |
| FMD, Arm 2 | 28 | 92.1±11.2 (87.9-96.2) | 87.9±120 (83.5-92.4) | 0.0003 | -4.1±5.2 | |
| Fasting Glucose (mg/dL) | | | | | | |
| Control Diet, Arm 1 | 41 | 88.1±8.9 (85.3-90.9) | 90.3±9.7 (87.3-93.4) | 0.14 | 2.2±9.5 | 0.27 |
| FMD, Arm 2 | 36 | 89.7±8.5 86.5-92.1) | 89.0±8.0 (86.4-91.6) | 0.87 | -08. ±9.9 | |
| IGF-1 (ng/mL) | | | | | | |
| Control Diet, Arm 1 | 41 | 180.2±84.5 (153.5-206.9) | 188.9±91.0 (160.2-217.7) | 0.14 | 8.7±36.9 | 0.0017** |
| FMD, Arm 2 | 38 | 168.6±69.1 (146.6-190.5) | 146.9±62.3 (127.0-166.7) | 0.0063 | -21.7±46.2 | |

*Fig. 9A*

| | n | mean±SD | (range) | mean±SD | (range) | p | change±SD | p |
|---|---|---|---|---|---|---|---|---|
| Systolic Blood Pressure (mmHg) | | | | | | | | |
| Control Diet, Arm 1 | 43 | 116±12.3 | (112.7-120.3) | 115.8±13.6 | (111.6-120.0) | 0.60 | -0.7±8.4 | 0.023 |
| FMD, Arm 2 | 38 | 118.0±13.4 | (113.7-122.2) | 113.5±13.2 | (109.3-117.7) | <0.0001 | -4.5±6.0 | |
| Diastolic Blood Pressure (mmHg) | | | | | | | | |
| Control Diet, Arm 1 | 43 | 75.5±9.6 | (72.5-78.5) | 74.8±10.0 | (71.7-77.9) | 0.45 | -0.7±6.2 | 0.053 |
| FMD, Arm 2 | 38 | 75.7±8.0 | (73.2-78.3) | 72.6±8.7 | (70.5-76.0) | 0.0089 | -3.1±4.7 | |
| Triglycerides (mg/dL) | | | | | | | | |
| Control Diet, Arm 1 | 37 | 100.5±68.2 | (77.7-123.2) | 101.5±57.1 | (82.5-120.6) | 0.85 | 1.0±35.0 | 0.27 |
| FMD, Arm 2 | 30 | 83.0±39.5 | (69.1-96.9) | 74.9±37.6 | (61.7-88.2) | 0.19 | -8.1±33.5 | |
| Total Cholesterol (mg/dL) | | | | | | | | |
| Control Diet, Arm 1 | 37 | 195.9±38.9 | (182.9-208.9) | 183.9±35.2 | (172.1-195.6) | 0.0015 | -12.0±21.3 | 0.81 |
| FMD, Arm 2 | 30 | 175.3±25.3 | (166.4-184.2) | 164.4±23.4 | (156.1-172.6) | 0.0012 | -10.9±17.0 | |
| LDL Cholesterol (mg/dL) | | | | | | | | |
| Control Diet, Arm 1 | 37 | 111.2±35.6 | (99.4-123.1) | 104.0±31.8 | (93.4-114.6) | 0.018 | -7.2±17.7 | 0.50 |
| FMD, Arm 2 | 30 | 94.1±23.0 | (86.0-102.2) | 89.7±22.8 | (81.7-97.7) | 0.13 | -4.4±16.0 | |
| HDL Cholesterol (mg/dL) | | | | | | | | |
| Control Diet, Arm 1 | 37 | 64.3±16.1 | (59.2-69.9) | 59.3±14.9 | (54.3-64.3) | 0.0002 | -5.3±7.8 | 0.90 |
| FMD, Arm 2 | 30 | 64.8±17.2 | 58.6-70.6) | 59.6±12.8 | (55.1-64.2) | 0.0097 | -5.0±10.0 | |
| C-reactive Protein (mg/L) | | | | | | | | |
| Control Diet, Arm1 | 42 | 1.5±1.9 | (0.92-2.11) | 1.9±2.7 | (1.07-2.75) | 0.31 | 0.4±2.5 | 0.27 |
| FMD, Arm 2 | 38 | 1.1±1.3 | (0.71-1.52) | 1.0±1.2 | (0.61-1.37) | 0.61 | -0.1±1.5 | |

‡ The body-mass index is the weight in kilograms divided by the square of the height in meters.
¥ Analysed by dual energy x-ray absorptiometry.
§ p-values comparing within-group changes were calculated using paired two-tailed Student's t-test.
* Plus-minus values are meant ± SD rounded to the nearest tenth
Between-arm comparison was calculated using two-tailed two-sample equal variance t-tests. Using the Benjamini-Hochberg method for controlling the false discovery rate of 0.05. p-values with *** indicates that the null hypothesis of no difference between the Control Diet (Arm 1) to FMD (Arm 2) can be rejected.

*Fig. 9B*

| Table 3. Comparisons of Changes in Risk Factors by Baseline Subgroups | | | |
|---|---|---|---|
| Subgroup | Group Differences (FMD – Control) Mean (95% CI) | Within subgroup p-value | Interaction p-value |
| Body Mass Index | | | |
| <25 | -0.5 (-1.2, -0.05) | 0.03 | 0.03 |
| 25-30 | -0.8 (-1.4, -0.3) | 0.003 | |
| >30 | -1.9 (-2.6, -1.1) | 0.0009 | |
| Systolic Blood Pressure | | | |
| >120 mmHg | -3.4 (-7.2, 0.5) | 0.086 | 0.80 |
| ≥120 mm Hg | -4.3 (-10.4, 1.8) | 0.17 | |
| Diastolic Blood Pressure | | | |
| <80 mmHg | -2.5 (-5.3, 0.3) | 0.08 | 0.87 |
| ≥80 mmHg | -3.0 (-8.2, 2.3) | 0.26 | |
| Fasting Glucose | | | |
| <99 mg/dL | -0.8 (-5.2, 3.6) | 0.72 | 0.12 |
| ≥99 mg/dL | -11.7 (-25.0, 1.5) | 0.08 | |
| IGF-1 | | | |
| <225 ng/mL | -18.7 (-38.6, 1.2) | 0.065 | 0.018 |
| ≥225 ng/mL | -70.9 (-109.3, -32.6) | 0.0004 | |
| Triglycerides | | | |
| <100 mg/dL | -4.6 (-24.1, 15.0) | 0.64 | 0.38 |
| ≥100 mg/dL | -19.1 (-45.8, 7.6) | 0.16 | |
| Cholesterol | | | |
| Total, <199 mg/dL | -1.8 (-12.6, 9.0) | 0.73 | 0.88 |
| Total, ≥199 mg/dL | -0.2 (-18.2, 17.7) | 0.98 | |
| LDL, <199 mg/dL Total Cholesterol | 1.0 (-8.8, 10.8) | 0.84 | 0.60 |
| LDL, ≥199 mg/dL Total Cholesterol | 6.2 (-11.2, 23.6) | 0.48 | |
| HDL, <50 mg/dL | -1.2 (-9.0, 0.5) | 0.75 | 0.70 |
| HDL, ≥50 mg/dL | 0.5 (-4.2, 5.2) | 0.83 | |
| C-reactive Protein | | | |
| <1 mg/L | 0.4 (-1.5, 8.7) | 0.47 | 0.59 |
| ≥1 mg/L | -0.9 (-2.4, 0.6) | 0.24 | |

Fig. 10

Table 4. Post hoc Analysis of Risk factors for age-related Diseases and Conditions, Diabetes and Cardio Vascular Disease in At-Risk Subjects

| Variable (at baseline) | N= | Baseline Mean ± SD (95%CI) | | FMD: 5 Days After 3rd FMD Cycle Mean ± SD (95%CI) | | p-value§ | Δ* | Efficacy (comparing Δ) p-value* |
|---|---|---|---|---|---|---|---|---|
| Body-mass Index‡ | | | | | | | | 0.0020△ |
| < 25 | 27 | 22.4±1.7 | (21.68-23.03) | 21.9±1.6 | (21.24-22.53) | 0.0014 | -0.5±0.7 | |
| 25-30 | 30 | 27.1±.4 | (26.58-27.60) | 26.4±1.6 | (25.76-26.99) | <0.0001 | -0.7±0.7 | |
| >30 | 14 | 34.4±3.5 | (32.37-36.36) | 33.0±3.5 | (30.95-34.95) | 0.0001 | 1.4±1.0 | |
| Systolic Blood Pressure (mmHg) | | | | | | | | |
| <120 mmHg | 49 | 110.3±6.9 | (108.5-112.4) | 107.9±7.7 | (105.7-110.1) | 0.0089 | -2.4±6.3 | 0.013 |
| >120 mmHg | 21 | 133.4±9.0 | (129.3-137.5) | 126.7±11.3 | (121.5-131.8) | 0.0002 | -6.7±6.9 | |
| Diastolic Blood Pressure (mmHg) | | | | | | | | |
| <80 mmHG | 53 | 71.8±5.0 | (70.43-73.21) | 70.3±5.9 | (68.64-71.89) | 0.032 | -1.5±5.1 | 0.010 |
| >80 mmHG | 17 | 87.7±6.9 | (84.20-91.27) | 82.2±10.0 | (77.09-87.38) | 0.0026 | -5.5±6.4 | |
| Fasting Glucose (mg/dL) | | | | | | | | |
| <99 mg/dL | 53 | 87.7±6.4 | (85.97-89.50) | 89.0±8.2 | (86.75-91.25) | 0.29 | 1.3±8.6 | < 0.0001 |
| >99 mg/dL | 13 | 104.2±4.4 | (101.5-106.9) | 92.4±8.2 | (87.42-97.35) | < 0.0001 | -11.8±6.9 | |
| IGF-1 (ng/mL) | | | | | | | | |
| <225 ng/mL | 52 | 145.1±38.4 | (134.4-155.8) | 131.0±46.8 | (118.0-144.0) | 0.014 | -14.1±39.9 | 0.00088 |
| >225 ng/mL | 17 | 286.6±47.0 | (261.6-311.7) | 231.5±64.7 | (197.0-265.9) | 0.0002 | -55.1±45.6 | |
| Triglycerides (mg/dL) | | | | | | | | |
| <100 mg/dL | 34 | 65.8±18.4 | (59.45-72.09) | 69.5±28.9 | (59.58-79.45) | 0.33 | 3.7±22.3 | 0.0035 |
| >100 mg/dL | 21 | 149.3±41.2 | (127.9-160.8) | 123.7±52.7 | (97.54-148.0) | 0.058 | -25.6±50.2 | |

*Fig. 11A*

| Cholesterol (mg/dL) | | | | | | | |
|---|---|---|---|---|---|---|---|
| Total, <199 mg/dL | 40 | 170.3±18.3 | (164.4-176.2) | 164.2±20.2 | (157.7-170.6) | 0.016 | -6.1±15.3 | |
| Total, >199 mg/dL | 15 | 228.1±23.0 | (215.4-240.9) | 208.2±26.3 | (193.6-222.8) | 0.0088 | -19.9±25.4 | 0.015 |
| LDL, <199 mg/dL Total Cholesterol | 40 | 91.4±20.2 | (85.0-97.73) | 88.8±21.0 | (82.13-95.38) | 0.22 | -2.6±13.4 | |
| LDL, >199 mg/dL Total Cholesterol | 15 | 141.1±29.1 | (125.0-157.2) | 126.2±24.7 | (112.2-139.9) | 0.018 | -14.9±21.7 | 0.13 |
| HDL, <50 mg/dL | 17 | 44.1±4.1 | (41.94-46.17) | 44.2±4.6 | (41.87-46.6) | 0.82 | 0.1±3.1 | |
| HDL, >50 mg/dL | 38 | 69.6±14.1 | (65.06-74.17) | 65.6±11.6 | (61.81-69.32) | 0.015 | -4.0±10.0 | 0.94 |
| C-reactive Protein (mg/L) | | | | | | | |
| <1 mg/L | 43 | 0.4±0.3 | (0.28-0.46) | 0.6±0.9 | (0.27-0.85) | 0.20 | 0.2±1.0 | |
| >1 mg/L | 26 | 3.3±2.8 | (2.22-4.44) | 1.6±1.2 | (1.06-2.15) | 0.0085 | -1.7±3.1 | 0.0003 |

‡ The body-mass index is the weight in kilograms divided by the square of the height in meters.

§ p-values comparing within-group changes were calculated using paired two-tailed Student's t-test.

* Plus-minus values are meant ± SD rounded to the nearest tenth

Between-arm comparison was calculated using two-tailed two-sample equal variance t-tests.

△ One-way analysis of variance for the BMI groups

*Fig. 11B*

Table 5. Complete Metabolic Panel

| Variable | N= | Baseline | | After Completion of 1st FMD cycle | | | | CTRL: 3 months after Baseline / FMD: 5 Days After 3rd FMD Cycle | | | | Efficacy (comparing Δ) p-value§ |
|---|---|---|---|---|---|---|---|---|---|---|---|---|
| | | Mean ±SD | (95%CI) | Mean±SD | (95% CI) | p-value§ | Δ* | Mean±SD | (95% CI) | p-value§ | Δ* | |
| Albumin (g/dL) | | | | | | | | | | | | |
| Control Diet, Arm 1 | 22 | 4.7±0.3 | (4.5-4.8) | | - | | | 4.4±0.4 | (4.3-4.6) | 0.0013 | -0.3±0.3 | |
| FMD, Arm 2 | 31 | 4.4±0.3 | (4.3-4.5) | 4.7±0.2 | (4.6-4.7) | < 0.0001 | 0.3±0.2 | 4.3±0.3 | (4.2-4.4) | 0.033 | -0.1±0.2 | 0.087 |
| Alkaline phosphatase (units/L) | | | | | | | | | | | | |
| Control Diet, Arm 1 | 22 | 59.3±17.7 | (51.7-66.9) | | | | | 56.6±13.7 | (50.9-62.3) | 0.37 | -2.7±13.3 | |
| FMD, Arm 2 | 31 | 58.5±14.5 | (53.4-63.7) | 59.7±14.2 | (54.5-64.8) | 0.13 | 1.2±5.6 | 55.2±13.4 | (50.4-60.) | 0.00059 | -3.3±6.1 | 0.819 |
| Alanine transaminase (units/L) | | | | | | | | | | | | |
| Control Diet, Arm 1 | 22 | 19.7±8.2 | (16.1-23.3) | | | | | 19.2±15.7 | (12.6-25.7) | 0.95 | -0.5±10.2 | |
| FMD, Arm 2 | 31 | 25.7±23.0 | (17.6-33.8) | 30.1±29.5 | (19.5-40.6) | 0.12 | 4.4±13.8 | 19.4±11.8 | (15.2-23.5) | 0.078 | -6.3±19.4 | 0.19 |
| Aspartate transaminase (units L) | | | | | | | | | | | | |
| Control Diet, Arm 1 | 22 | 22.4±6.4 | (19.7-25.2) | | | | | 24.2±9.2 | (20.4-28.1) | 0.28 | 1.8±8.5 | |
| FMD, Arm 2 | 31 | 27.9±24.3 | (19.3-36.4) | 31.6±17.4 | (25.4-37.8) | 0.34 | 3.7±20.3 | 24.2±8.8 | (21.1-27.3) | 0.37 | -3.7±22.6 | 0.27 |
| Bilirubin (Total) (mg/dL) | | | | | | | | | | | | |
| Control Diet, Arm 1 | 22 | 0.6±0.4 | (0.4-0.8) | | | | | 0.5±0.3 | (0.4-0.6) | 0.14 | -0.1±0.2 | |
| FMD, Arm 2 | 31 | 0.6±0.5 | (0.4-0.8) | 0.9±0.9 | (0.6-1.3) | 0.00035 | 0.3±0.4 | 0.5±0.3 | (0.4-0.6) | 0.027 | -01±0.3 | 0.50 |

Fig. 12A

| Group | n | Baseline ± SD | (range) | Mid ± SD | (range) | p | Change | Post ± SD | (range) | value | Change ± SD | p |
|---|---|---|---|---|---|---|---|---|---|---|---|---|
| Blood Urea Nitrogen (mg/dL) | | | | | | | | | | | | |
| Control Diet, Arm 1 | 22 | 13.6±5.0 | (11.4-15.7) | 9.8±3.3 | (8.6-11.0) | < 0.0001 | -4.0±2.8 | 13.3±5.0 | (11.2-15.4) | 0.96 | -0.3±4.4 | 0.68 |
| FMD, Arm 2 | 31 | 13.8±4.9 | (12.0-15.5) | | | | | 13.3±4.6 | (11.6-14.9) | 0.41 | -0.5±3.3 | |
| Calcium (mg/dL) | | | | | | | | | | | | |
| Control Diet, Arm 1 | 22 | 9.5±0.4 | (9.3-9.6) | 9.5±0.4 | (9.4-9.6) | 0.0093 | 0.2±0.3 | 9.4±0.3 | (9.5-9.5) | 0.38 | -0.1±0.4 | 0.55 |
| FMD, Arm 2 | 31 | 9.3±0.4 | (9.2-9.5) | | | | | 9.3±0.4 | (9.2-9.4) | 0.46 | 0.0±0.2 | |
| Chloride (mmol/L) | | | | | | | | | | | | |
| Control Diet, Arm 1 | 22 | 101.5±2.1 | (100.7-102.4) | 99.6±2.7 | (98.5-102.7) | 0.00011 | -1.9±2.4 | 101.3±1.7 | (100.6-102.0) | 0.64 | -0.2±2.1 | 0.23 |
| FMD, Arm 2 | 31 | 101.5±2.1 | (100.8-102.3) | | | | | 102.0±2.3 | (101.2-102.8) | 0.16 | 0.5±1.6 | |
| $CO_2$ (mmol/L) | | | | | | | | | | | | |
| Control Diet, Arm 1 | 22 | 27.3±2.2 | (26.2-28.4) | 25.8±2.4 | (24.9-26.7) | 0.0029 | 1.1±1.9 | 26.9±1.5 | (26.2-27.7) | 0.57 | -0.4±2.6 | 0.47 |
| FMD, Arm 2 | 32 | 26.9±2.5 | (26-27.8) | | | | | 27.1±2.8 | (26.0-28.1) | 0.73 | 0.2±2.1 | |
| Creatinine (mg/dL) | | | | | | | | | | | | |
| Control Diet, Arm 1 | 22 | 0.8±0.2 | (0.7-0.9) | 0.90.8±20.2 | (0.8-0.9) | 0.0001 | 0.1±0.2 | 0.8±0.2 | (0.7-0.9) | 0.36 | 0.0±0.1 | 0.082 |
| FMD, Arm 2 | 31 | 0.8±0.2 | (0.7-0.9) | | | | | 0.8±0.2 | (0.8-0.9) | 0.11 | 0.0±0.1 | |
| Potassium (mmol/L) | | | | | | | | | | | | |
| Control Diet, Arm 1 | 22 | 4.3±0.5 | (4.1-4.5) | 4.3±0.3 | (4.1-4.4) | 0.39 | 0.1±0.5 | 4.3±0.4 | (4.2-4.5) | 0.47 | 0.0±0.5 | 0.82 |
| FMD, Arm 2 | 31 | 4.2±0.3 | (4.1-4.3) | | | | | 4.3±0.5 | (4.1-4.5) | 0.13 | 0.1±0.4 | |
| Sodium (mmol/L) | | | | | | | | | | | | |
| Control Diet, Arm 1 | 22 | 138.7±2.0 | (137.9-139.6) | 137I.7±3.0 | (13.6-138.8) | 0.13 | -0.8±2.3 | 137.6±1.6 | (136.9-138.2) | 0.47 | 0.0±0.5 | 0.024 |
| FMD, Arm 2 | 31 | 138.5±2.2 | (137.7-139.3) | | | | | 138.8±2.5 | (137.9-139.7) | 0.43 | 0.1±0.4 | |

*Fig. 12B*

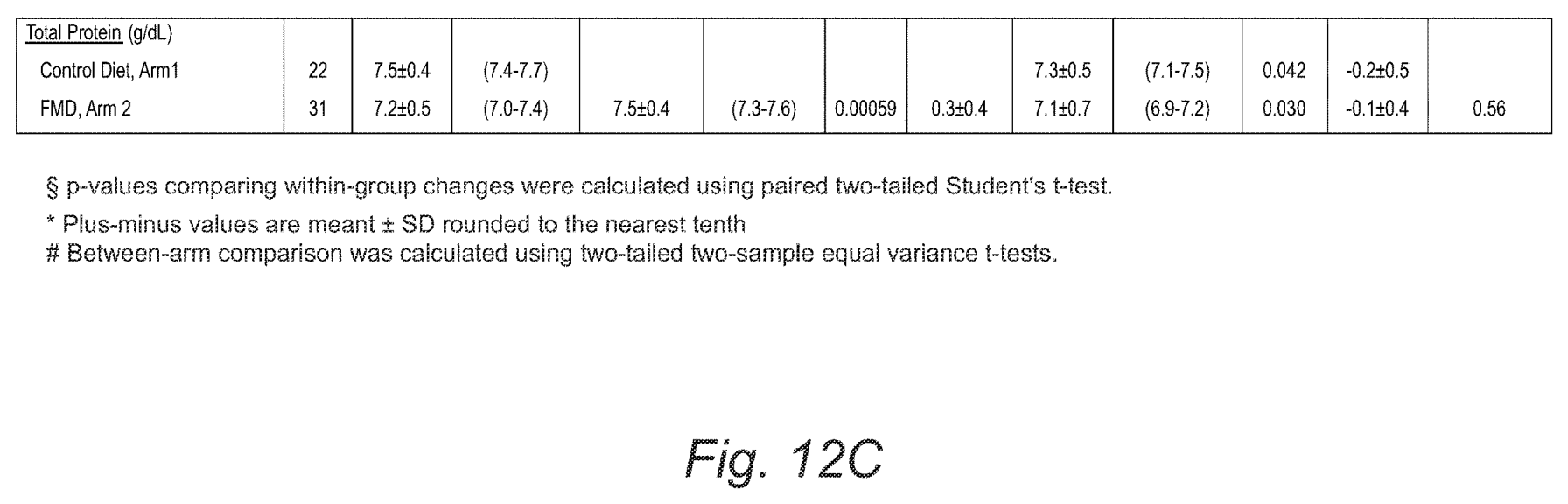

| Total Protein (g/dL) | | | | | | | | |
|---|---|---|---|---|---|---|---|---|
| Control Diet, Arm1 | 22 | 7.5±0.4 | (7.4-7.7) | | | 7.3±0.5 | (7.1-7.5) | 0.042 | -0.2±0.5 |
| FMD, Arm 2 | 31 | 7.2±0.5 | (7.0-7.4) | 7.5±0.4 | 0.00059 | 0.3±0.4 | (7.3-7.6) | 7.1±0.7 | (6.9-7.2) | 0.030 | -0.1±0.4 | 0.56 |

§ p-values comparing within-group changes were calculated using paired two-tailed Student's t-test.

* Plus-minus values are meant ± SD rounded to the nearest tenth

Between-arm comparison was calculated using two-tailed two-sample equal variance t-tests.

*Fig. 12C*

Table 6. Arm-specific Markers of Adherence and Changes in Risk factors, including Arm 1 after Cross-over to FMD, and Summary of FMD Arm 1 and 2

| Variable | N= | Baseline Mean ± SD | (95%CI) | CTRL: 3 months after Baseline / FMD: 5 Days After 3rd FMD Cycle Mean ± SD | (95%CI) | p-value§ | Δ* | Efficacy p-value§ (FMD Arm 2 vs.) CTRL (Arm 1) | FMD (Arm 1) |
|---|---|---|---|---|---|---|---|---|---|
| Body Weight (kg) | | | | | | | | | |
| Control Diet, Arm 1 | 43 | 77.2±16.5 | (72.1-82.2) | 77.3±17.0 | (72.0-82.6) | 0.72 | 0.1±2.1 | | |
| FMD, Arm 2 | 39 | 74..1±15.5 | (69.3-78.9) | 71.6±14.6 | (67.0-76.1) | <0.0001 | -2.6±2.5 | <0.0001 | 0.12 |
| FMD, Arm 1 | 32 | 79.0±18.4 | (72.6-85.3) | 77.3±17.5 | (71.2-83.3) | <0.0001 | -1.7±2.0 | | |
| FMD, Arm 1 and 2 | 71 | 76.3±16.9 | (72.3-80.3) | 74.1±16.1 | (70.3-77.9) | <0.0001 | -2.2±2.3 | | |
| Body-mass Index‡ | | | | | | | | | |
| Control Diet, Arm 1 | 43 | 27.4±4.8 | (25.9-28.9) | 27.4±5.0 | (25.9-28.9) | 0.82 | 0.0±0.7 | | |
| FMD, Arm 2 | 39 | 26.2±4.4 | (24.8-27.6) | 25.3±4.3 | (24.0-26.5) | <0.0001 | -0.9±0.9 | <0.0001 | 0.71 |
| FMD, Arm 1 A | 32 | 27.4±5.3 | (25.5-29.2) | 26.8±5.1 | (25.0-28.6) | <0.0001 | -0.6±0.7 | | |
| FMD, Arm 1 and 2 | 71 | 26.7±4.8 | 25.6-27.9 | 26.0±4.5 | (24.9-27.0) | <0.0001 | -0.7±0.8 | | |
| **Total Body Fat* (abs.Volume)** | | | | | | | | | |
| Control Diet, Arm 1 | 43 | 23651±8155 | (21142-26161) | 23607±8337 | (21041-26173) | 0.83 | -44±1365 | | |
| FMD, Arm 2 | 38 | 20643±8459 | (17953-23332) | 19249±7792 | (16722-21726) | <0.0001 | -1393±1786 | 0.0002 | 0.67 |
| FMD, Arm 1 | 32 | 22841±8733 | 19185-25866 | 21618±8567 | (18650-24587) | 0.0001 | -1222±1484 | | |
| FMC, Arm 1 and 2 | 70 | 21648±8594 | 19598-23697 | 20332±8182 | 18381-22283 | <0.0001 | -1315±1646 | | |

*Fig. 13A-1*

| | n | | | | | | | | |
|---|---|---|---|---|---|---|---|---|---|
| **Total Body Fat* (rel. Volume %)** | | | | | | | | | |
| Control, Arm 1 | 43 | 33.4±8.6 | (30.7-36.0) | 33.3±9.0 | (30.5-36.1) | 0.68 | -0.1±1.5 | | |
| FMD, Arm 2 | 38 | 30.3±10.0 | (27.2-33.5) | 29.4±9.8 | (26.3-32.6) | 0.0095 | -0.9±2.0 | 0.043 | 0.72 |
| FMD, Arm 1 | 32 | 31.4±8.9 | (28.3-34.5) | 30.3±8.8 | (27.3-33.4) | 0.0031 | -1.1±1.8 | | |
| FMD, Arm 1 and 2 | 70 | 30.8±9.5 | (28.6-33.1) | 29.8±9.3 | (27.6-32.1) | <0.0001 | -1.0±1.9 | | |
| **Trunk Fat* (abs. Volume)** | | | | | | | | | |
| Control Diet, Arm 1 | 43 | 8429±4742 | (6969-9888) | 8395±4776 | (6925-9865) | 0.83 | -33±1046 | | |
| FMD, Arm 2 | 38 | 6573±4877 | (5022-8124) | 5938±4295 | (4572-7303) | 0.0023 | -636±1198 | 0.018 | 0.77 |
| FMD, Arm 1 | 32 | 7807±4848 | (6127-9486) | 7092±4578 | (5506-8678) | 0.0004 | -715±1015 | | |
| FMD, Arm 1 and 2 | 70 | 7137±4869 | (5976-8298) | 6465±4432 | (5408-7522) | <0.0001 | -672-1111 | | |
| **Trunk Fat* (rel. Volume %)** | | | | | | | | | |
| Control, Arm 1 | 43 | 11.7±5.7 | (9.92-13.44) | 11.7±6.0 | (9.81-13.52) | 0.96 | 0.0±1.3 | | |
| FMD, Arm 2 | 38 | 9.5±6.1 | (7.52-11.40) | 8.9±5.6 | (7.12-10.69) | 0.016 | -0.6±1.4 | 0.069 | 0.47 |
| FMD, Arm 1 | 32 | 10.5±5.9 | (8.46-12.55) | 9.7±5.4 | (7.84-11.57) | 0.0037 | -0.8±1.5 | | |
| FMD, Arm 1 and 2 | 70 | 9.9±6.0 | 8.51-11.37) | 9.2±5.5 | (7.96-10.58) | 0.0002 | -0.7±1.4 | | |
| **Lean Body Mass* (abs. Volume)** | | | | | | | | | |
| Control, Arm 1 | 43 | 45016±11318 | (41533-48500) | 45188±11885 | (41531-48846) | 0.44 | 172±1441 | | |
| FMD, Arm 2 | 38 | 45321±11794 | (41571-49071) | 44423±11247 | (40655-47807) | 0.0002 | -1089±1613 | 0.0004 | 0.81 |
| FMD, Arm 1 | 32 | 47451±12323 | (43151-51691) | 47016±11555 | (43006-51014) | 0.14 | -411±1575 | | |
| FMD, Arm 1 and 2 | 70 | 46281±11997 | (43240-49142) | 45501±11392 | (42785-48218) | 0.0001 | -780±1620 | | |
| **Lean Body Mass* (rel. Volume %)** | | | | | | | | | |
| Control, Arm 1 | 43 | 63.9±8.2 | (61.4-66.4) | 64.0±8.7 | (61.3-66.7) | 0.64 | 0.1±1.5 | | |
| FMD, Arm 2 | 38 | 66.8±9.6 | (63.7-69.8) | 67.6±9.4 | (64.6-70.6) | 0.016 | 0.8±2.0 | 0.070 | 0.67 |
| FMD, Arm 1 | 32 | 65.8±8.6 | (62.8-68.8) | 66.8±8.4 | (63.9-69.7) | 0.0052 | 1.0±1.8 | | |
| FMD, Arm 1 and 2 | 70 | 66.3±9.1 | (64.2-68.5) | 67.2±9.2 | (65.1-69.3) | 0.0002 | 0.9±1.9 | | |

*Fig. 13A-2*

| | N | | | | | p | Change | p | p |
|---|---|---|---|---|---|---|---|---|---|
| Waist Circumference (cm) | | | | | | | | | |
| Control, Arm 1 | 28 | 95.4±14.2 | (89.9-100.9) | 94.6±14.5 | (88.9-100.2) | 0.10 | -0.8±25 | | |
| FMD, Arm 2 | 28 | 92.1±11.2 | (87.9-96.2) | 87.9±120 | (83.5-92.4) | 0.0003 | -4.1±5.2 | 0.0035 | 0.073 |
| FMD, Arm 1 | 24 | 97.6±15.5 | (91.4-103.8) | 95.8±13.7 | (90.3-101.3) | 0.022 | -1.8±3.6 | | |
| FMD, Arm 1 and 2 | 52 | 94.6±13.5 | (90.9-98.4) | 91.6±13.3 | (87.9-95.3) | < 0.0001 | -3.0±4.6 | | |
| Fasting Glucose (mg/dL) | | | | | | | | | |
| Control, Arm 1 | 41 | 88.1±8.9 | (85.3-90.9) | 90.3±9.7 | (87.3-93.4) | 0.14 | 2.2±9.5 | | |
| FMD, Arm 2 | 36 | 89.7±8.5 | (86.5-92.1) | 89.0±8.0 | (86.4-91.6) | 0.87 | -0.8±9.9 | 0.27 | 0.35 |
| FMD, Arm 1 | 30 | 93.0±9.1 | (89.8-96.3) | 90.2±8.4 | (87.4-93.5) | 0.14 | -2.8±8.8 | | |
| FMD, Arm 1 and 2 | 66 | 91.0±9.0 | (88.8-93.2) | 89.7±8.2 | (87.7-91.7) | 0.28 | -1.3±9.8 | | |
| B-Hydroxybutyrate (mM) | | | | | | | | | |
| Control, Arm 1 | 42 | 0.5±0.4 | (0.35-0.61) | 0.5±0.6 | (0.28-0.68) | 0.99 | 0.0±0.8 | | |
| FMD, Arm 2 | 38 | 0.4±0.3 | (0.34-0.55) | 0.4±0.3 | (0.33-0.50) | 0.55 | 0.0±0.3 | 0.82 | 0.67 |
| FMD, Arm 1 | 31 | 0.4±0.3 | (0.32-0.55) | 0.4±0.2 | (0.30-0.44) | 0.26 | 0.0±0.3 | | |
| FMD, Arm 1 and 2 | 69 | 0.4±0.3 | (0.36-0.52) | 0.4±0.2 | (0.34-0.45) | 0.23 | 0.0±0.3 | | |
| IGF-1 (ng/mL) | | | | | | | | | |
| Control, Arm 1 | 41 | 180.2±84.5 | (153.5-206.9) | 188.9±91.0 | (160.2-217.7) | 0.14 | 8.7±36.9 | | |
| FMD, Arm 2 | 38 | 168.6±69.1 | (146.6-190.5) | 146.9±62.3 | (127.0-166.7) | 0.063 | -21.7±46.2 | 0.0017 | 0.54 |
| FMD, Arm 1 | 31 | 191.3±75 | (165.9-217.7) | 162.9±71.0 | (137.9-187.9) | 0.0011 | -28.4±43.6 | | |
| FMD, Arm 1 and 2 | 69 | 178.8±72.2 | (161.5-196.1) | 154.1±66.4 | (138.1-170.0) | < 0.0001 | -24.7±44.9 | | |
| IGFBP-1 (ng/mL) | | | | | | | | | |
| Control, Arm 1 | 41 | 35.5±43.6 | (21.8-49.3) | 36.5±47.9 | (21.4-51.7) | 0.81 | 1.0±26.9 | | |
| FMD, Arm 2 | 38 | 24.2±17.1 | (18.8-29.7) | 22.2±16.4 | (17.0-27.4) | 0.35 | -2.0±13.0 | 0.53 | 0.84 |
| FMD, Arm 1 | 31 | 33.8±51.2 | (15.8-51.8) | 33.9±42.7 | (18.9-49.0) | 0.99 | 0.1±62.2 | | |
| FMD, Arm 1 and 2 | 69 | 28.5±36.6 | (19.7-37.3) | 27.5±31.4 | (19.9-35.0) | 0.84 | -1.0±42.4 | | |

*Fig. 13A-3*

Table 6. continued

| Variable | N= | Baseline Mean ± SD (95%CI) | FMD: 5 Days After 3rd FMD Cycle / CTRL: 3 months after Baseline | | | Efficacy p-value§ (FMD Arm 2 vs.) | |
| --- | --- | --- | --- | --- | --- | --- | --- |
| | | | Mean ± SD (95%CI) | p-value§ | Δ* | CTRL (Arm 1) | FMD (Arm 1) |
| Systolic Blood Pressure (mmHg) | | | | | | | |
| Control Diet, Arm 1 | 43 | 116.5±12.3 (112.7-120.3) | 115.8±13.6 (111.6-120.0) | 0.60 | -0.7±8.4 | | |
| FMD, Arm 2 | 38 | 118.0±13.4 (113.7-122.2) | 113.5±13.2 (109.3-117.7) | <0.0001 | -4.5±6.0 | 0.023 | |
| FMD, Arm 1 | 32 | 116.5±12.6 (112.6-120.9) | 113.6±11.5 (109.7-117.6) | 0.039 | -2.9±7.6 | | 0.32 |
| FMD, Arm 1 and 2 | 70 | 117.4±13.0 (114.2-120.4) | 113.6±12.4 (110.6-116.5) | <0.0001 | -3.8±5.8 | | |
| Diastolic Blood Pressure (mmHg) | | | | | | | |
| Control Diet, Arm 1 | 43 | 75.5±9.6 (72.5-78.5) | 74.8±10.0 (71.7-77.9) | 0.45 | -0.7±6.2 | | |
| FMD, Arm 2 | 38 | 75.7±8.0 (73.2-78.3) | 72.6±8.7 (70.5-76.0) | 0.0089 | -3.1±4.7 | 0.053 | |
| FMD, Arm 1 A | 32 | 75.6±9.8 (72.2-79.1) | 73.1±9.0 (70.0-76.2) | 0.021 | -2.6±5.9 | | 0.96 |
| FMD, Arm 1 and 2 | 70 | 75.7±8.8 (73.6-77.8) | 72.8±8.8 (70.7-74.9) | 0.0004 | -2.9±5.3 | | |
| Triglycerides (mg/dL) | | | | | | | |
| Control Diet, Arm 1 | 37 | 100.5±68.2 (77.7-123.2) | 101.5±57.1 (82.5-120.6) | 0.85 | 1.0±35.0 | | |
| FMD, Arm 2 | 30 | 83.0±39.5 (69.1-96.9) | 74.9±37.6 (61.7-88.2) | 0.19 | -8.1±33.5 | 0.27 | |
| FMD, Arm 1 A | 25 | 114.6±56.4 (92.4-136.8) | 108.3±51.8 (88.0-128.6) | 0.48 | -6.2±43.4 | | 0.86 |
| FMD, Arm 1 and 2 | 55 | 97.4±50.4 (83.74-111.0) | 90.2±47.5 (77.3-103.0) | 0.16 | -7.2±38.2 | | |
| Total Cholesterol (mg/dL) | | | | | | | |
| Control Diet, Arm 1 | 37 | 195.9±38.9 (182.9-208.9) | 183.9±35.2 (172.1-195.6) | 0.0015 | -120±21.3 | | |
| FMD, Arm 2 | 30 | 175.3±25.3 (166.4-184.2) | 164.4±23.4 (156.1-172.6) | 0.0012 | -10.9±17.0 | 0.81 | |
| FMD, Arm 1 A | 25 | 199.3±35.2 (185.3-213.1) | 190.2±29.8 (178.5-201.9) | 0.05 | -9.1±22.3 | | 0.73 |
| FMD, Arm 1 and 2 | 55 | 186.1±32.5 (177.3-194.9) | 176.2±29.4 (168.2-184.1) | 0.0004 | -9.9±19.5 | | |

Fig. 13B-1

| | N | | | | | | | | |
|---|---|---|---|---|---|---|---|---|---|
| LDL Cholesterol (mg/dL) | | | | | | | | | |
| Control Diet, Arm 1 | 37 | 111.2±35.6 | (99.4-123.1) | 104.0±31.8 | (93.4-114.6) | 0.018 | -7.2±17.7 | | |
| FMD, Arm 2 | 30 | 94.1±23.0 | (86.0-102.2) | 89.7±22.8 | (81.7-97.7) | 0.13 | -4.4±16.0 | 0.50 | 0.46 |
| FMD, Arm 1 A | 25 | 117.8±36.3 | (103.6-132.1) | 110.1±29.0 | (98.7-121.5) | 0.039 | -7.8±17.8 | | |
| FMD, Arm 1 and 2 | 55 | 104.9±32.0 | (96.2-113.5) | 99.2±27.6 | (91.8-106.7) | 0.0011 | -5.7±16.8 | | |
| HDL Cholesterol (mg/dL) | | | | | | | | | |
| Control Diet, Arm 1 | 37 | 64.3±16.1 | (59.2-69.9) | 59.3±14.9 | (54.3-64.3) | 0.0002 | -5.3±7.8 | | |
| FMD, Arm 2 | 30 | 64.8±17.2 | (58.6-70.6) | 59.6±12.8 | (55.1-64.2) | 0.0097 | -5.0±10.0 | -0.90 | 0.033 |
| FMD, Arm 1 A | 25 | 58.4±16.2 | (52.1-64.8) | 58.4±15.6 | (52.3-64.5) | 0.97 | 0.0±5.8 | | |
| FMD, Arm 1 and 2 | 55 | 61.7±16.9 | (57.1-66.3) | 58.9±14.1 | (55.1-62.7) | 0.020 | -2.8±8.7 | | |
| C-reactive Protein (mg/L) | | | | | | | | | |
| Control Diet, Arm 1 | 42 | 1.5±1.9 | (0.92-2.11) | 1.9±2.7 | (1.07-2.75) | 0.31 | 0.4±2.5 | | |
| FMD, Arm 2 | 38 | 1.1±1.3 | (0.71-1.52) | 1.0±1.2 | (0.61-1.37) | 0.61 | -0.1±1.5 | 0.27 | 0.096 |
| FMD, Arm 1 A | 31 | 1.9±3.0 | (0.89-2.98) | 0.9±1.2 | (0.47-1.35) | 0.053 | -1.0±2.8 | | |
| FMD, Arm 1 and 2 | 69 | 1.5±2.2 | (0.95-2.02) | 1.0±1.2 | (0.66-1.25) | 0.052 | -0.5±2.2 | | |

‡ The body-mass index is the weight in kilograms divided by the square of the height in meters.

¥ Analysed by dual energy x-ray absorptiometry.

§ p-values comparing within-group changes were calculated using paired two-tailed Student's t-test.

* Plus-minus values are mean ± SD rounded to the nearest tenth

Between-arm comparison was calculated using two-tailed two-sample equal variance t-tests.

*Fig. 13B-2*

Table 7. Changes in Risk Factors and Biomarkers of Adherence after the first FMD

| Variable | N= | Baseline Mean±SD (95% CI) | | After Completion of 1st FMD Cycle Mean±SD (95% CI) | | p-value§ | Δ* |
|---|---|---|---|---|---|---|---|
| Body Weight | | | | | | | |
| Kg | 71 | 76.3±16.9 | (72.30-80.32) | 73.8±16.3 | (69.98-77.66) | < 0.0001 | -2.5±1.1 |
| Body-mass Index‡ | | | | | | | |
| All Subjects | 71 | 26.7±4.8 | (25.58-27.86) | 25.9±4.7 | (24.76-26.96) | < 0.0001 | -0.8±0.3 |
| < 25 | 27 | 22.4±1.7 | (21.68-23.03) | 21.6±1.6 | (20.98-22.25) | < 0.0001 | -0.7±0.3 |
| 25-30 | 30 | 27.1±1.4 | (26.58-27.60) | 26.3±1.5 | (25.71-26.78) | < 0.0001 | -0.8±0.3 |
| > 30 | 14 | 34.4±3.5 | (32.37-36.36) | 33.2±3.2 | (31.37-35.10) | < 0.0001 | -1.2±0.4 |
| Total Body Fat* | | | | | | | |
| Abs. Volume | 70 | 21648±8594 | (19598-23697) | 20320±9326 | (17582-23058) | 0.075 | -1328±1714 |
| Rel. Volume % | 70 | 30.8±9.5 | (28.55-33.06) | 30.1±10.2 | (27.05-33.06) | 0.047 | -0.7±1.6 |
| Lean Body Mass* | | | | | | | |
| abs. Volume | 70 | 46281±11997 | (43240-49142) | 44469±11554 | (41077-47862) | < 0.0001 | -1812±1997 |
| rel. Volume % | 70 | 66.3±9.1 | (64.15-68.50) | 66.9±9.9 | (63.99-69.79) | 0.020 | 0.9±9.5 |
| Waist Circumference | | | | | | | |
| cm | 52 | 94.6±13.5 | (90.86-98.38) | 91.8±14.5 | (86.66-96.91) | < 0.0001 | -2.8±13.1 |
| Fasting Glucose | | | | | | | |
| Mg/dL | 66 | 91.0±9.0 | (88.78-93.19) | 80.1±9.2 | (77.78-82.31) | < 0.0001 | -10.9±10.1 |
| Beta-Hydroxybutyrate | | | | | | | |
| mM | 69 | 0.4±0.3 | (0.36-0.52) | 1.3±0.9 | (1.12-1.54) | < 0.0001 | 0.9±0.9 |

*Fig. 14A*

| | | | | | | |
|---|---|---|---|---|---|---|
| IGF-1 Ng/ml | 69 | 178.8±72.2 | (161.5-196.1) | 134.5±67.6 | (118.2-150.7) | < 0.0001 | -44.3±51.6 |
| IGFBP-1 Ng/ml | 69 | 28.5±36.6 | (19.73-37.32) | 48.3±43.6 | (37.79-58.73) | <0.0001 | 19.7±32.7 |
| Systolic Blood Pressure mmHg | 70 | 117.4±13.0 | (114.2-120.4) | 115.7±13.8 | (112.4-118.9) | 0.076 | -1.7±7.8 |
| Diastolic Blood Pressure mmHg | 70 | 75.7±8.8 | (73.59-77.78) | 73.3±9.7 | (70.98-75.62) | 0.0003 | -2.4±5.3 |
| Triglycerides Mg/dL | 55 | 97.4±50.4 | (83.74-111.0) | 74.1±28.2 | (66.47-81.71) | <0.0001 | -23.3±39.3 |
| Cholesterol Total, mg/dL | 55 | 186.1±32.5 | (177.3-194.9) | 189.8±38.1 | (179.5-200.1) | 0.12 | 3.7±17.7 |
| LDL, mg/dL | 55 | 104.9±32.0 | (96.23-113.5) | 112.4±39.2 | (101.8-123.0) | 0.0026 | 7.5±17.8 |
| HDL, All subjects | 55 | 61.7±16.9 | (57.12-66.26) | 62.5±16.5 | (58.06-67.00) | 0.29 | 0.8±5.8 |
| C-reactive Protein Mg/L | 69 | 1.5±2.2 | (0.95-2.02) | 1.6±1.9 | (1.10-2.03) | 0.75 | 0.1±2.1 |

‡ The body-mass index is the weight in kilograms divided by the square of the height in meters.

⚹ Analysed by dual energy x-ray absorptiometry.

§ p-values comparing within-group changes were calculated using paired two-tailed Student's t-test.

* Plus-minus values are meant ± SD rounded to the nearest tenth

*Fig. 14B*

Table 8. Changes in Risk Factors and Biomarkers of Adherence after the first FMD

| Variable | N= | Baseline Mean±SD (95% CI) | | After Completion of 1st FMD Cycle Mean±SD (95% CI) | | p-value§ | Δ* |
|---|---|---|---|---|---|---|---|
| Body Weight | | | | | | | |
| All subjects | 48 | 77.0±17.9 | (71.79-82.17) | 75.6±17.3 | (70.54-80.60) | 0.0002 | -1.4±2.5 |
| Body-mass Index‡ | | | | | | | |
| All Subjects | 48 | 26.7±4.8 | (25.33-28.10) | 26.2±4.6 | (24.88-27.57) | 0.0002 | -0.5±0.9 |
| < 25 | 18 | 22.5±1.8 | (21.62-23.39) | 22.1±1.9 | (21.14-23.05) | 0.041 | -0.4±0.8 |
| 25-30 | 20 | 26.8±1.3 | (26.22-27.41) | 26.5±1.5 | (25.78-27.19) | 0.094 | -0.3±0.8 |
| > 30 | 10 | 34.1±3.7 | (31.46-36.72) | 33.1±3.6 | (30.56-35.70) | 0.010 | -1.0±0.9 |
| Total Body Fat¥ | | | | | | | |
| Abs. Volume | 45 | 21267±8582 | (18689-23845) | 20388±8393 | (17866-22910) | 0.0065 | -879±2064 |
| Rel. Volume % | 45 | 30.3±9.5 | (27.41-33.10) | 29.6±9.5 | (26.76-32.43) | 0.060 | -0.7±2.3 |
| Lean Body Mass¥ | | | | | | | |
| abs. Volume | 45 | 47054±12829 | (43200-50909) | 46460±12377 | (42741-50178) | 0.0040 | -595±1315 |
| rel. Volume % | 45 | 66.9±9.1 | (64.14-69.62) | 67.5±9.1 | (64.73-70.18) | 0.089 | 0.6±2.2 |
| Waist Circumference (cm) | | | | | | | |
| All subjects | 36 | 93.2±13.6 | (88.63-97.81) | 91.4±13.3 | (86.92-95.89) | 0.0048 | -1.8±3.6 |

Fig. 15A

| | n | | | | |
|---|---|---|---|---|---|
| Fasting Glucose (mg/dL) | | | | | |
| All subjects | 44 | 91.2±9.1 (88.40-93.61) | 89.6±7.8 (87.23-91.95) | 0.31 | -1.6±10.0 |
| > 99 mg/dL | 9 | 105.1±5.1 (101.2-109.0) | 94.6±5.4 (90.40-98.71) | 0.0019 | -10.6±7.0 |
| IGF-1 (ng/mL) | | | | | |
| All subjects | 41 | 175.7±69.3 (153.8-197.6) | 161.0±59.3 (142.3-179.8) | 0.061 | -14.7±48.8 |
| > 225 ng/mL | 9 | 282.7±47.0 (246.6-318.8) | 212.0±59.0 (166.6-257.4) | 0.0007 | -70.7±39.9 |
| Systolic Blood Pressure (mmHg) | | | | | |
| All subjects | 48 | 118.2±13.9 (114.2-122.2) | 116.1±12.3 (112.6-119.7) | 0.046 | -2.1±7.0 |
| > 120 mmHg | 17 | 133.3±9.8 (128.2-138.2) | 128.0±9.6 (123.1-132.9) | 0.0064 | -5.2±6.9 |
| Diastolic Blood Pressure mmHg | | | | | |
| All subjects | 48 | 75.9±9.4 (73.13-78.56) | 73.1±9.0 (70.52-75.76) | 0.0005 | -2.8±5.0 |
| > 80 mmHg | 11 | 89.4±7.3 (84.44-94.29) | 83.9±10.5 (76.85-90.92) | 0.010 | -5.5±5.7 |
| Triglycerides (mg/dL) | | | | | |
| All subjects | 37 | 96.0±46.3 (80.58-111.5) | 88.6±45.5 (73.40-103.7) | 0.065 | -7.5±23.8 |
| > 100 mg/dL | 14 | 144.2±35.9 (123.5-164.9) | 132.6±41.6 (108.6-156.6) | 0.22 | -11.6±33.4 |

Fig. 15B

| Cholesterol | | | | | | |
|---|---|---|---|---|---|---|
| Total, All subjects | 37 | 181.8±29.6 | (171.9-191.6) | 182.3±26.2 | (173.5-191.0) | 0.86 | 0.5±17.1 |
| Total, > 199 mg/dL | 8 | 222.1±24.3 | (201.8-242.4) | 208.8±28.8 | (184.7-232.8) | 0.11 | -13.4±21.0 |
| LDL, All subjects | 37 | 98.8±28.8 | (89.17-108.4) | 98.4±25.5 | (90.66-107.0) | 0.98 | -04±11.5 |
| LDL, > 199 mg/dL   Total | | | | | | |
| Cholesterol | 8 | 134.1±27.5 | (111.1-157.1) | 124.9±28.9 | (100.7-149.0) | 0.085 | -9.3±13.0 |
| HDL, All subjects | 10 | 63.8±16.9 | (58.18-69.44) | 65.7±15.7 | (60.46-70.95) | 0.24 | 1.9±9.7 |
| HDL, > 50 mg/dL | | 44.9±4.1 | (41.93-47.87) | 48.5±5.4 | (44.64-52.36) | 0.021 | 3.6±4.1 |
| C-reactive Protein (mg/L) | | | | | | |
| All subjects | 47 | 1.3±2.1 | (0.63-1.88) | 1.0±1.1 | (0.63-1.30) | 0.39 | -0.3±2.2 |
| < 1 mg/L | 16 | 3.0±2.9 | (1.46-4.57) | 1.6±1.2 | (0.99-2.32) | 0.13 | -1.4±3.4 |

‡ The body-mass index is the weight in kilograms divided by the square of the height in meters.

¥ Analysed by dual energy x-ray absorptiometry.

§ p-values comparing within-group changes were calculated using paired two-tailed Student's t-test.

* Plus-minus values are meant ± SD rounded to the nearest tenth

FASTING MIMICKING DIET

CROSS-REFERENCE TO RELATED APPLICATIONS

This application is a continuation of U.S. patent application Ser. No. 15/432,803 filed Feb. 14, 2017, the disclosure of which is hereby incorporated in its entirety by reference herein.

TECHNICAL FIELD

The present invention, in general, relates to compositions that mimicking fasting while still providing nutrients to a subject.

BACKGROUND

Recently, fasting mimicking diets have been found to provide a number of health benefits. For example, fasting mimicking diets have been found to be useful in alleviating symptoms of chemotherapy, diabetes, and hypertension.

Metabolic syndrome is defined by co-occurrence of 3 out of 5 of the following conditions: abdominal obesity, elevated fasting glucose, elevated blood pressure, high serum triglycerides, and low levels of high-density cholesterol (HDL) (1). Affecting 47 million Americans (2), it is associated with a major increase in the risk of cardiovascular disease, and all-cause mortality (3). Although prolonged fasting or very low calorie fasting-mimicking diets (FMDs) can ameliorate the incidence of diseases such as cancer and multiple sclerosis in mice (4-6), randomized trials to assess fasting's ability to reduce risk factors for aging and major age-related diseases have not been carried out (7-9). Prolonged fasting, in which only water is consumed for 2 or more days, reduces pro-growth signaling and activates cellular protection mechanisms in organisms ranging from single cell yeast to mammals (10). This is achieved in part by temporarily reducing glucose and circulating insulin-like growth factor 1 (IGF-1), a hormone well-studied for its role in metabolism, growth, and development, as well as for its association with aging and cancer (11-16). In fact, severe growth hormone receptor and IGF-1 deficiencies are associated with a reduced risk of cancer, diabetes and overall mortality in humans (17, 18).

Mice fed periodically with the FMD show extended health-span and multi-system regeneration, reduced inflammation and cancer incidence, and enhanced cognitive performance (5). Despite its potential for disease prevention and treatment, prolonged fasting is difficult to implement in human subjects and may exacerbate pre-existing nutritional deficiencies, making it not feasible and/or safe for children, the elderly, frail individuals and even for the majority of healthy adults.

Accordingly, there is a need for the development of additional diet protocols that may be useful in treating human diseases.

SUMMARY

Against this prior art background, a fasting mimicking diet is provided. The fasting mimicking diet (FMD) is found to be more practical and safer than fasting while providing ingredients at levels expected to enhance the effects of fasting to affect markers or risk factors for aging and diseases. The FMD is based on a diet previously tested in animals and designed to achieve effects similar to those caused by fasting on IGF-1, IGFBP1, glucose, and ketone bodies but not restricted to those (17). To prevent nutrient deficiency, the FMD provides between 3000 kJ and 4600 kJ per day, as well as high micronutrient nourishment, to each human subject (5). The safety and feasibility of this intervention had been previously evaluated in 19 study participants who consumed 3 monthly cycles of this FMD lasting 5 days each (5).

In an embodiment, a fasting mimicking diet package providing daily meal portions for a predetermined number of days is provided. The fasting mimicking diet package includes a kale cracker composition, a first vegetable broth composition, a mushroom soup composition, a tomato soup composition, a quinoa-containing minestrone soup composition, a bean-containing minestrone soup composition, and a pumpkin soup composition. Characteristically, the daily meal portions are packaged into meal servings or into a total daily serving to be divided into meals.

In another embodiment, another fasting mimicking diet package providing daily meal portions for a predetermined number of days is provided. The fasting mimicking diet package includes a nut-containing nutrition bar, a cocoa-containing nutrition bar, a first olive-containing composition, a kale cracker composition, a vegetable soup composition, and a first vegetable broth composition, a tea composition that includes spearmint, a energy drink composition, a micronutritional composition, and a algal oil composition. Characteristically, the daily meal portions are packaged into meal servings or into a total daily serving to be divided into meals.

Advantageously, the fasting mimicking diet packages set forth herein can be used to alleviate symptoms of chemotherapy, promote cell regeneration, alleviate symptoms of aging, treat or prevent diabetes, treat or prevent metabolic disorder, treat or prevent hypertension and help prevent cancer when administered to a subject identified has having symptoms of these ailments.

DRAWINGS

FIG. 1A is a schematic illustration of a fasting mimicking diet package.

FIG. 1B. Consort Diagram. Consort Diagram of 102 contacted subjects of which 100 were enrolled into the study two arms. Arm 1 (N=48), the "Control" group, maintained their normal caloric intake for a three months monitoring period. Data were collected at enrollment and again after 3 months. Participants in arm 2 (N=52) started the fasting-mimicking diet (FMD) after randomization. The FMD is provided for 5 days/month for 3 consecutive cycles. Data were collected at enrollment, immediately after completion of the 1$^{st}$ FMD cycle but before resuming normal dietary intake, and on average 5 days after subjects resumed their normal diet after the final FMD cycle. After the initial 3 month period, subjects in arm 1 then also started the FMD. An optional follow-up visit in the clinic for analysis was offered to all participants approximately 3 months after the completion of the third FMD cycle.

FIGS. 2A, 2B, 2C, 2D, 2E, 2F, 2G, 2H, 2I, 2J, 2K, 2L, 2M, 2N, and 2O. Change analysis of metabolic variables during the randomization. Effects on aging/disease markers and risk factors in all subjects that completed the randomized analysis in either the control arm or in the FMD arm (5-7 days after the third cycle of FMD). The A change represents a comparison to baseline. All data are presented as mean±SD. Between-arm comparisons were calculated using two-tailed two-sample equal variance t-tests. For some of the 100 enrolled participants, the nurses were unable to collect all the samples/measurements from all subjects. We therefore excluded subjects with incomplete measurements from a particular marker group. See Table 2 for details.

FIGS. 3A, 3B, 3C, 3D, 3E, 3F, 3G, 3H, 3I, and 3J. Post-hoc analysis of metabolic variables in subgroups identified by severity of risk factors. Subjects from both study arms who completed three FMD cycles were post-hoc stratified based on being either in normal-risk or at-risk subgroups for factors associated with age-related diseases and conditions. The A change shown represents comparisons to baseline. All data are presented as mean±SD. Between-arm comparisons were calculated using two-tailed two-sample equal variance t-tests. One-way analysis of variance was used for the BMI groups. See Table 4 for details.

FIG. 4. Subject self-reported adverse effects based on Common Terminology Criteria for Adverse Effects.

FIG. 5. Comparison of participants that completed the trial vs. dropouts.

FIGS. 6A-1, 6A-2, 6A-3, and 6A-4. BMI: Baseline to 3 months before/after comparison of individual subjects in the control cohort and all subjects that completed the FMD.

FIGS. 6B-1, 6B-2, and 6B-3. Baseline to 3 months before/after comparison of individual subjects in the control cohort and all subjects that completed the FMD.

FIGS. 6C-1, 6C-2, and 6C-3. Diastolic blood pressure: Baseline to 3 months before/after comparison of individual subjects in the control cohort and all subjects that completed the FMD.

FIGS. 6D-1, 6D-2, and 6D-3. Fasting Glucose: Baseline to 3 months before/after comparison of individual subjects in the control cohort and all subjects that completed the FMD.

FIGS. 6E-1, 6E-2, and 6E-3. ICF-1: Baseline to 3 months before/after comparison of individual subjects in the control cohort and all subjects that completed the FMD.

FIGS. 6F-1, 6F-2, and 6F-3. Triglycerides: Baseline to 3 months before/after comparison of individual subjects in the control cohort and all subjects that completed the FMD.

FIGS. 6G-1, 6G-2, and 6G-3. Total Cholesterol: Baseline to 3 months before/after comparison of individual subjects in the control cohort and all subjects that completed the FMD.

FIGS. 6H-1, 6H-2, and 6H-3. LDL: Baseline to 3 months before/after comparison of individual subjects in the control cohort and all subjects that completed the FMD.

FIGS. 6I-1, 6I-2, and 6I-3. HDL: Baseline to 3 months before/after comparison of individual subjects in the control cohort and all subjects that completed the FMD.

FIGS. 6J-1, 6J-2, and 6J-3. Baseline to 3 months before/after comparison of individual subjects in the control cohort and all subjects that completed the FMD.

FIGS. 7A, 7B, 7C, 7D, 7E, 7F, 7G, and 7H. Nutritional Information of the Fasting Mimicking Diet.

FIG. 8 is Table 1 which provides the baseline characteristics of the Subjects.

FIGS. 9A and 9B are Table 2 which provides study arm-specific biomarkers of adherence and changes in risk factors.

FIG. 10 is Table 3 which provides comparisons of changes in risk factors by baseline subgroups.

FIGS. 11A and 11B are Table 4 which provides post hoc analysis of risk factors for age-related diseases and conditions, diabetes and cardio-vascular disease in at-risk subjects.

Figure 1B:
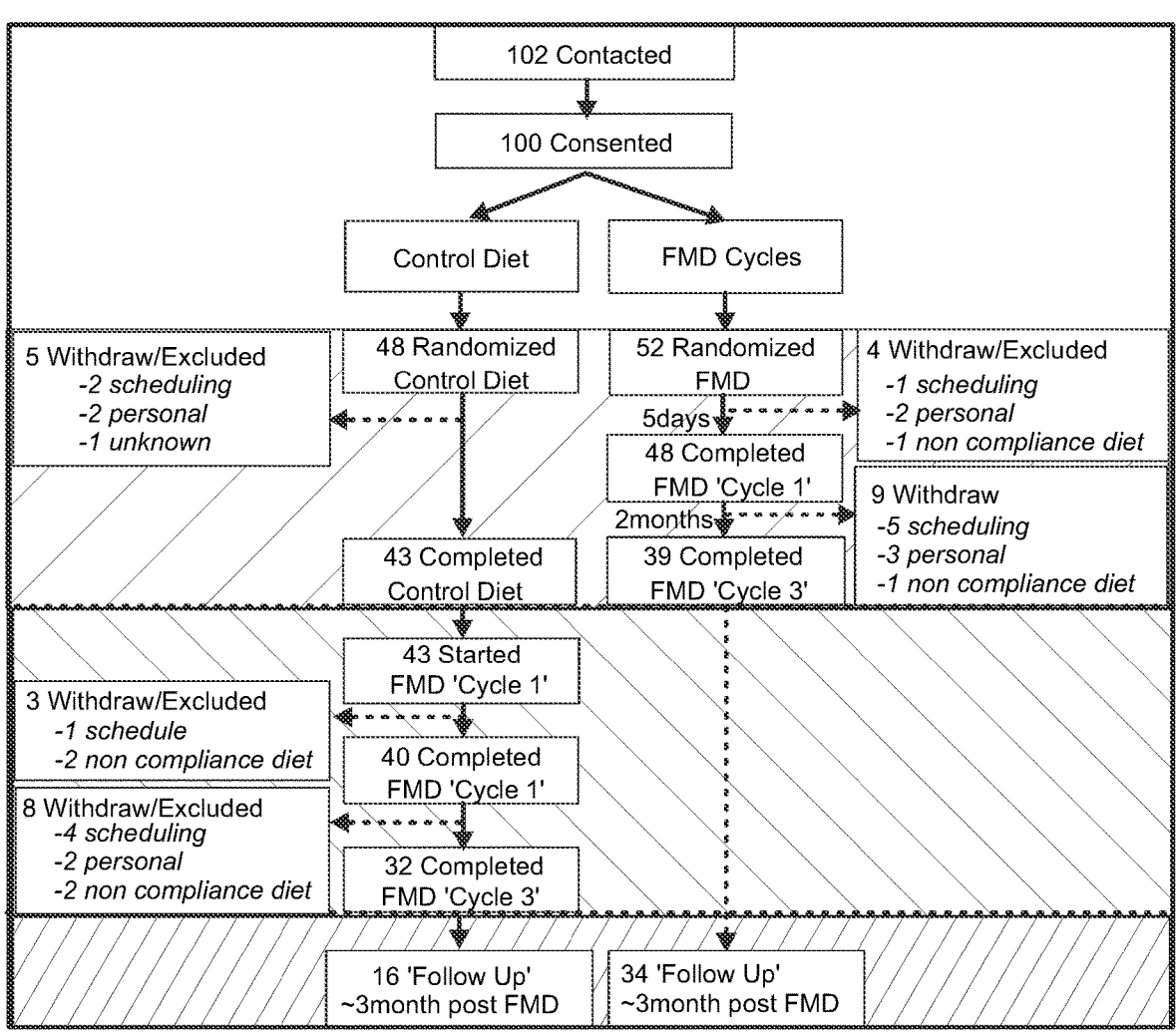
Figure 2E:
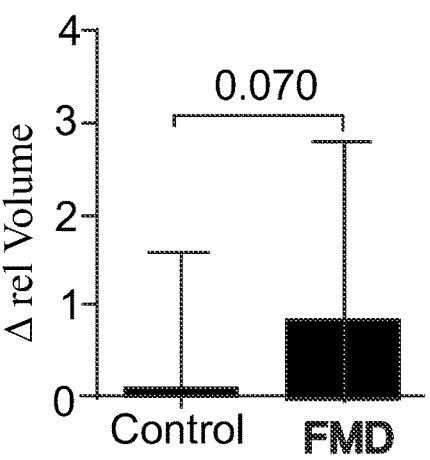
Figure 2F:
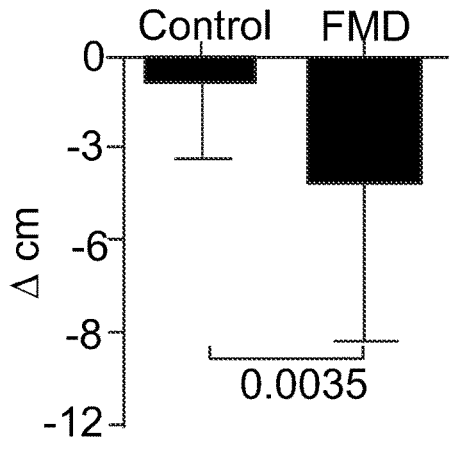
Figure 2G:
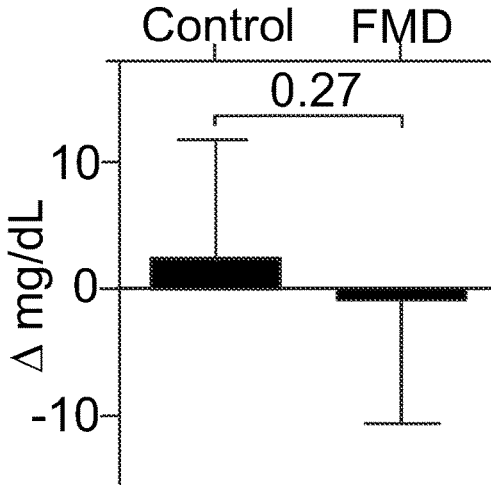
Figure 2H:
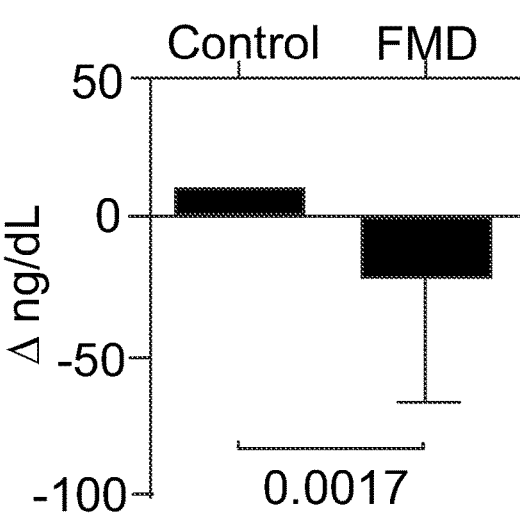
Figure 2I:
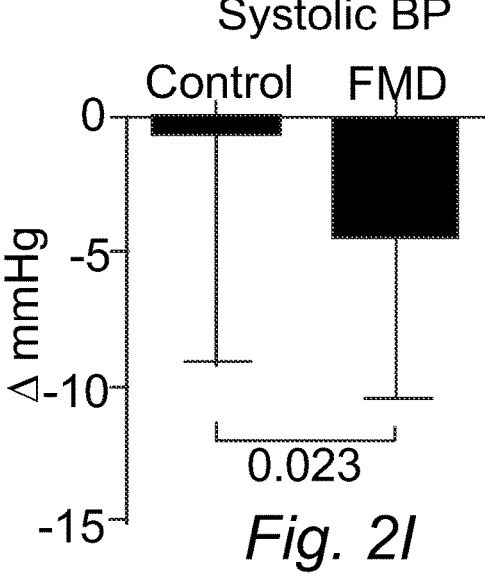
Figure 2J:
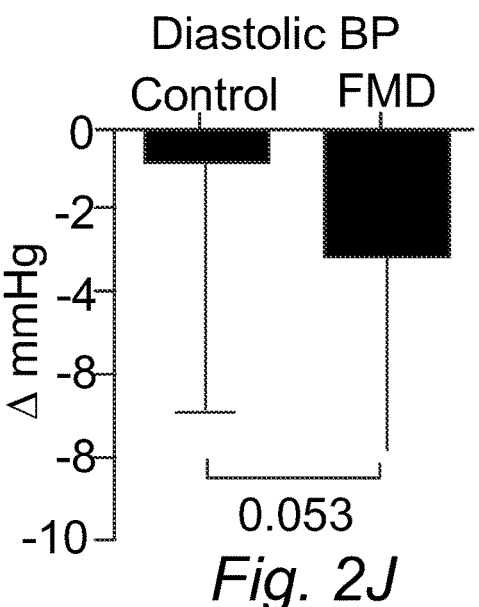
Figure 2K:
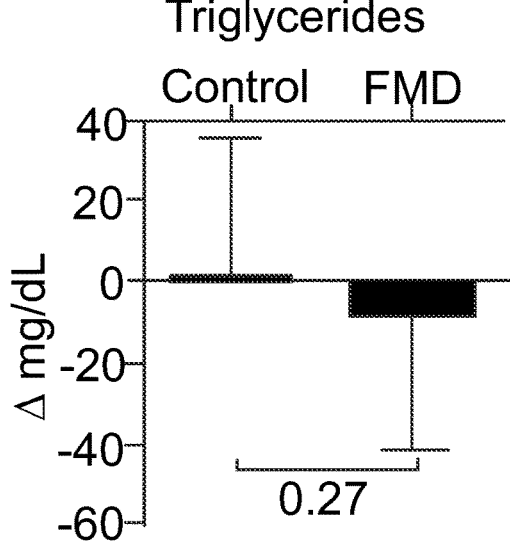
Figure 2L:
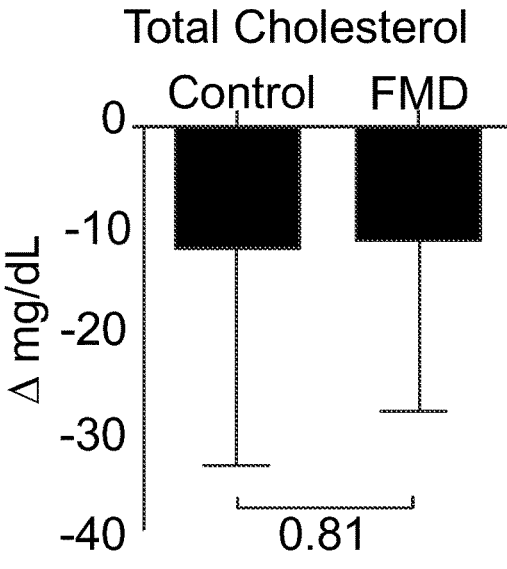
Figure 3A:
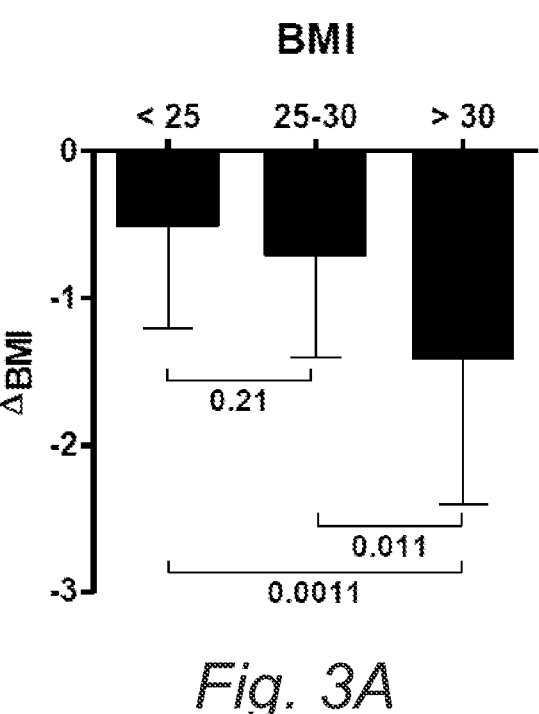
Figure 3B:
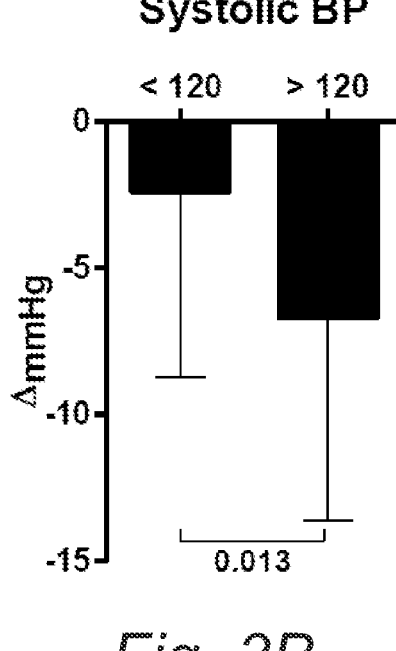
Figure 3C:
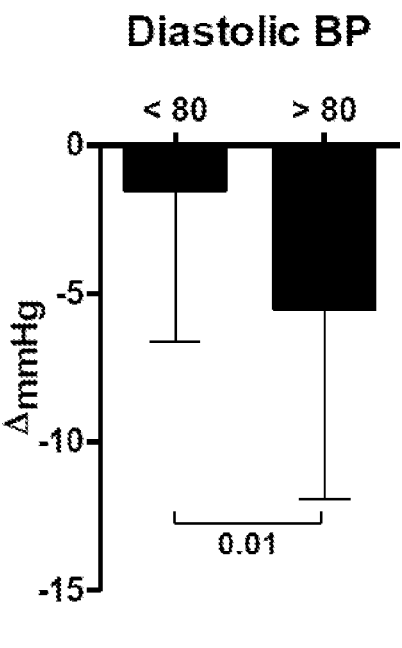
Figure 3D:
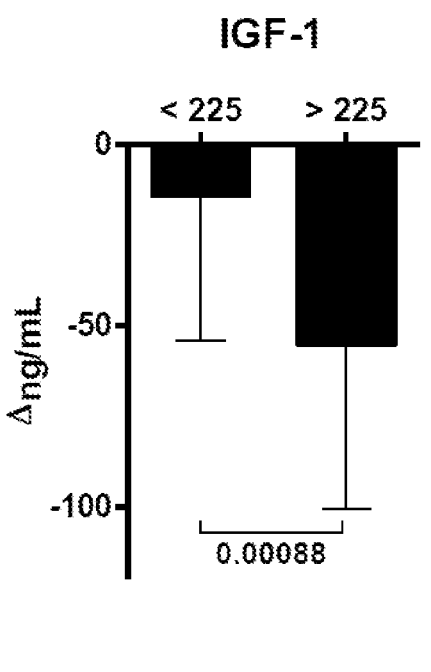
Figure 3E:
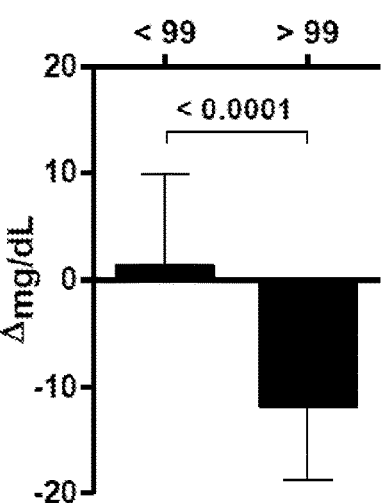
Figure 3F:
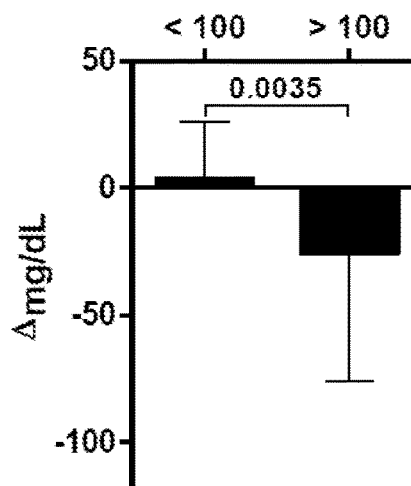
Figure 3G:
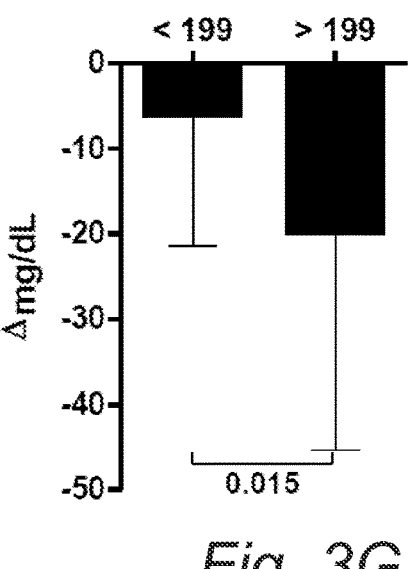
Figure 3H:
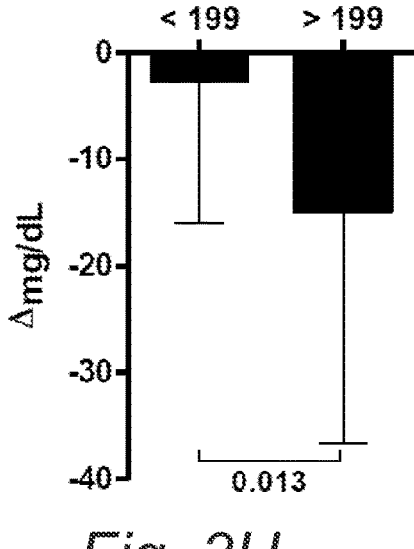
Figure 3I:
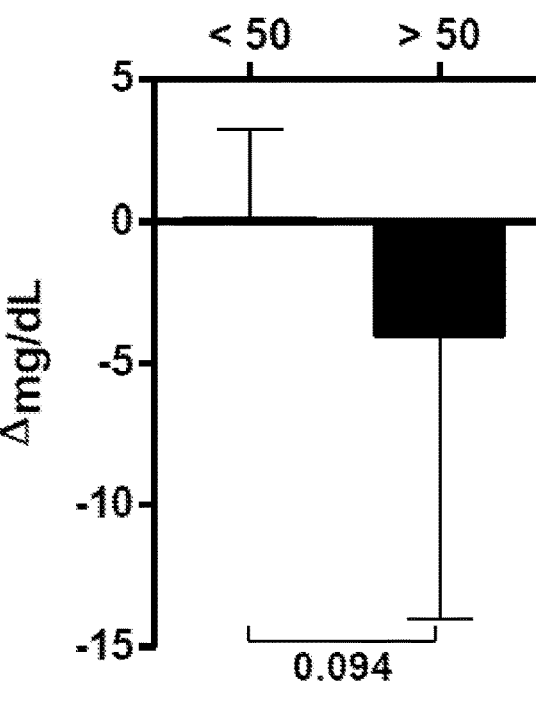
Figure 3J:
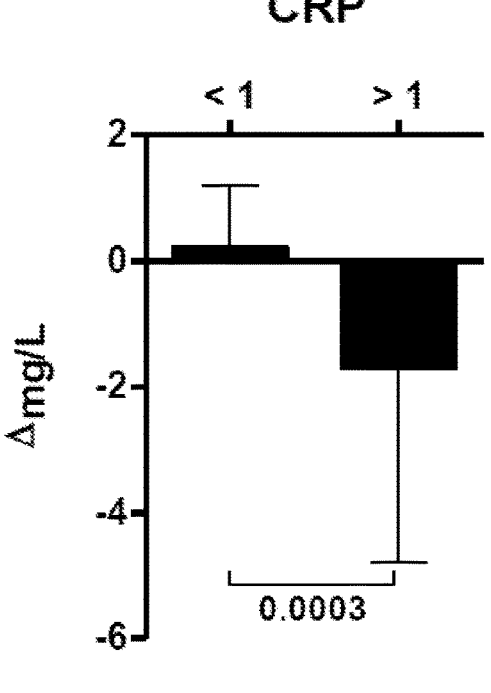

FIGS. 12A, 12B, and 12C are Table 5 which provides Complete Metabolic Panel.

FIGS. 13A-1, 13A-2, 13A-3, 13B-1 and 13B-2 are Table 6 which provides Arm-specific Markers of Adherence and Changes in Risk factors, including Arm 1 after Cross-over to FMD, and Summary of FMD Arm 1 and 2.

FIGS. 14A and 14 B are Table 7 which provides Changes in Risk factors and Metabolic markers of Adherence after the first FMD.

FIGS. 15A, 15 B, and 15 C are Table 8 which provides Changes in Risk factors and Metabolic markers of Adherence 3 months after Intervention.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The term "subject" refers to a human or animal, including all mammals such as primates (particularly higher primates), sheep, dog, rodents (e.g., mouse or rat), guinea pig, goat, pig, cat, rabbit, and cow.

The term "fasting mimicking and enhancing diet" means a diet that mimics the effects of fasting typically by providing a subject with at most 50-75% of their normal caloric intake. However, if the fasting mimicking diet composition is maintained, based on our current and previous findings, partial disease prevention and treatment effects are anticipated even if 100% of the normal caloric intake is provided to subjects. The term "fasting mimicking and enhancing diet" is sometimes simply referred to as a "fasting mimicking diet." These diets include those diets that have been referred to as fasting mimicking diets. Examples of useful fasting mimicking and enhancing diets and method for monitoring the effects of these diets on markers such as IGF-1 and IGFBP1 in the context of the present invention are set forth in U.S. patent application Ser. No. 14/273,946 filed May 9, 2014; Ser. No. 14/497,752 filed Sep. 26, 2014; Ser. No. 12/910,508 filed Oct. 22, 2010; Ser. No. 13/643,673 filed Oct. 26, 2012; Ser. No. 13/982,307 filed Jul. 29, 2013; Ser. No. 14/060,494 filed Oct. 22, 2013; Ser. No. 14/178,953 filed Feb. 12, 2014; Ser. No. 14/320,996 filed Jul. 1, 2014; Ser. No. 14/671,622 filed Mar. 27, 2015; the entire disclosure of these patent applications is hereby incorporated by reference. The fasting mimicking diet set forth in U.S. patent application Ser. Nos. 14/060,494 and 14/178,953 are found to be particularly useful in the present invention.

In an embodiment of the present invention, a diet package for administering a fasting mimicking diet is provides. The fasting mimicking diet package provides daily meal portions for a predetermined number of days. Typically, the predetermined number of days is from 1 to 10 days (i.e., 1, 2, 3, 4, 5, 6, 7, 8, 9, or 10 days). In a particularly useful variation, the predetermined number of days is 5 or 6 days. In some variations, the fasting mimicking diets set forth herein provide a subject at most, in increasing order of preference, 75%, 50%, 40%, 30%, or 10% of the subject's normal caloric intake or the daily recommended caloric intake for a subject. In a refinement, the fasting mimicking diet provides at least, in increasing order of preference, 5%, 10%, or 20% of the subject's normal caloric intake or the daily recommended caloric intake for a subject. However, if the fasting mimicking diet composition is maintained, based on our current and previous findings, partial disease prevention and treatment effects are anticipated even if 100% of the normal caloric intake is provided to subjects. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the fasting mimicking diet provides the subject with 700 to 1200 kcal/day. In a particularly useful refinement, the fasting mimicking diet provides a male subject of average weight with about 1100 kcal/day and a female subject of average weight with 900 kcal/day. In some variation, the diet from the diet package is administered on consecutive days. In another variation, the daily meal portions provided for only one day a week for at least a month.

In one embodiment, the fasting mimicking diet package providing daily meal portions for a predetermined number of days as set forth above. The fasting mimicking diet package includes a kale cracker composition, a first vegetable broth composition, a mushroom soup composition, a tomato soup composition, a quinoa-containing minestrone soup composition, a bean-containing minestrone soup composition, and a pumpkin soup composition. Characteristically, the daily meal portions are packaged into meal servings or into a total daily serving to be divided into meals. In a refinement, the fasting mimicking diet package further includes a nut-containing nutrition bar, a cocoa-containing nutrition bar, a first olive-containing composition, a first vegetable broth composition, a tea composition that includes spearmint, a energy drink composition, a micronutritional composition, and a algal oil composition. In a further refinement, the fasting mimicking diet package further includes a second olive-containing composition, a second vegetable broth composition, a tea composition that includes spearmint and lemon, and a tea composition that includes hibiscus.

In a variation of the embodiments set forth above, the fasting mimicking diet package includes daily meal portions that provide less than 40 grams of sugar for day 1, less than 30 grams of sugar for days 2 to 5 and any remaining days, less than 28 grams of protein for day 1, less than 18 grams of protein for days 2 to 5 and any remaining days, 20-30 grams of monounsaturated fats or more to reach the desired caloric intake (i.e., a predetermined caloric intake) for day 1, 6-10 grams of polyunsaturated fats or more to reach the desired caloric intake for day 1, 2-12 grams of saturated fats or more to reach the desired caloric intake for day 1, 10-15 grams of monounsaturated fats or more to reach the desired caloric intake for days 2 to 5 and any remaining days, 3-5 grams of polyunsaturated fats or more to reach the desired caloric intake for days 2 to 5 and any remaining days, 1-6 grams of saturated fats or more to reach the desired caloric intake for days 2 to 5, or any remaining days, and a micronutrient composition on each day and any remaining days.

In another variation of the embodiments set forth above, the fasting mimicking diet package includes daily meal portions 8-10 kcal per kilogram body weight for each diet day. In this variation, the fasting mimicking diet provides less than 30 grams of sugar for each diet day, less than 18 grams of protein for each diet day, 9-15 grams of monounsaturated fats or more to reach the desired caloric intake for each diet day, and 2.5-4.5 grams of polyunsaturated fats or more to reach the desired caloric intake for each diet day and 1-5.5 grams of saturated fats or more to reach the desired caloric intake for each diet day. Higher levels of the fats listed above can be provided for higher FMD formulation providing up to 100% of the normal caloric intake to subjects.

In still another variation of the embodiments set forth above, the fasting mimicking diet package includes daily meal portions that provide 5-8 kcal per kilogram body weight for each diet day. In this variation, the fasting mimicking diet provides less than 20 grams of sugar for each diet day, less than 12 grams of protein for each diet day, and 6.5-10 grams of monounsaturated fats or more to reach the desired caloric intake for each diet day, 2.5-4.5 grams of polyunsaturated fats or more to reach the desired caloric intake for each diet day and 1.5-4 grams of saturated fats or more to reach the desired caloric intake for each diet day.

In still another variation of the embodiments set forth above, the fasting mimicking diet package includes daily meal servings that provide 0-3 kcal per kilogram body weight for each diet day. In this variation, the fasting mimicking diet provides less than 5 grams of sugar for each diet day, less than 3 grams of protein for each diet day, and less than 2.5 grams of monounsaturated fats for each diet day, less than 1 grams of polyunsaturated fats for each diet day and less than 1 grams of saturated fats for each diet day.

In an embodiment, the nutritional requirements for the fasting mimicking diet set forth above can be realized by a diet package with certain specific meal components. In one variation as depicted in FIG. 1A, the fasting mimicking diet package 10 provides daily meal portions for a predetermined number of days are set forth above (e.g., 1, 2, 3, 4, 5, 6, 7, 8, 9, or 10 days). The fasting mimicking diet package 10 includes a kale cracker composition (item 12), a first vegetable broth composition (item 14), a mushroom soup composition (item 16), a tomato soup composition (item 18), a quinoa-containing minestrone soup composition (item 20), a bean-containing minestrone soup composition (item 22), and a pumpkin soup composition (item 24), Characteristically, the daily meal portions are packaged into meal servings or into a total daily serving to be divided into meals. In a refinement, the fasting mimicking diet package further includes a nut-containing nutrition bar (item 26), a cocoa-containing nutrition bar (item 28), a first olive-containing composition (item 30), a first vegetable broth composition (item 32), a tea composition that includes spearmint (item 34), a energy drink composition (item 36), a micronutritional composition (item 38), and a algal oil composition (item 40). In a further refinement, the fasting mimicking diet package further includes a second olive-containing composition (item 42), a second vegetable broth composition (item 44), a tea composition that includes spearmint and lemon (item 46), and a tea composition that includes hibiscus (item 48). It should be appreciated that each of the soup, broth, tea and energy compositions set forth herein are designed to have added water when consumed.

In another variation of a fasting mimicking diet package, diet package 10 includes a nut-containing nutrition bar (item 26), a cocoa-containing nutrition bar (item 28), a first olive-containing composition (item 30), a kale cracker composition (item 12), a vegetable soup composition (item 14), a first vegetable broth composition (item 14), a tea composition that includes spearmint (item 34), a energy drink composition (item 36), a micronutritional composition (item 38), and a algal oil composition (item 40). Characteristically, the daily meal portions are packaged into meal servings or into a total daily serving to be divided into meals. This diet package also includes daily meal portions for a predetermined number of days as set forth above with the daily meal portions being packaged into meal servings or into a total daily serving to be divided into meals. In a refinement, the fasting mimicking diet package further includes a mushroom soup composition (item 16), a tomato soup composition (item 18), a quinoa-containing minestrone soup composition (item 20), and a pumpkin soup composition. In a further refinement, the fasting mimicking diet package further includes a second olive-containing composition (item 42), a second vegetable broth composition (item 44), a bean-containing minestrone soup composition (item 22), a tea composition that includes spearmint and lemon (item 46), and a tea composition that includes hibiscus (item 48).

As set forth above, the fasting mimicking diet packages includes specific meal components. Typically, compositions are as follows. The nut-containing nutrition bar includes almond meal and macadamia nuts. The cocoa-containing nutrition bar includes almond butter, almonds, and brown rice crispy (e.g., brown puffed rice). The mushroom soup composition includes brown rice powder, carrots, inulin, and mushrooms. The bean-containing minestrone soup composition includes white beans, cabbage, and potatoes. The first vegetable broth composition includes carrots, maltodextrin, celery, spinach, and tomatoes. The second vegetable broth composition includes carrots, maltodextrin, celery, spinach, soy lecithin, and tomatoes. The energy drink composition includes glycerin and water. The algal oil composition includes schizocatrium algae oil. The micronutrient composition includes beet root powder, calcium carbonate, carrots, collard leaf, kale leaf, and tomatoes. In a refinement, the micronutrient composition includes Vit A, Vit C, Ca, Fe, Vit D3, Vit E, Vit K, Vit B1, Vit B2, Vit B3, Vit B5, Vit B6, Vit B7, Vit B9, Vit B12, Cr, Cu, I, Mg, Mn, Mo, Se, and Zn.

In a refinement, the nut-containing nutrition bar (L-Bar Nut based) includes almond meal and macadamia nuts. In a refinement, the nut-containing nutrition bar (L-Bar Nut based) includes almond meal preferably in an amount of 20 to 35 weight %; coconut preferably in an amount of 2 to 10 weight %; coconut oil preferably in an amount of 1 to 8 weight %; flax seed meal preferably in an amount of 1 to 8 weight %; honey preferably in an amount of 10 to 30 weight %; macadamia nuts preferably in an amount of 10 to 30 weight %; pecans preferably in an amount of 10 to 25 weight %; salt preferably in an amount of 0.1 to 0.8 weight %; and optionally vanilla preferably in an amount of 0.3 to 1.5 weight %.

In a refinement, the cocoa-containing nutrition bar (L-Bar ChocoCrisp) includes almond butter, almonds, and brown rice crispy (PGP10235). In a refinement, the cocoa-containing nutrition bar (L-Bar ChocoCrisp) includes almond butter preferably in an amount of 10 to 25 weight %; almonds preferably in an amount of 3 to 12 weight %; brown rice crispy (PGP10235) preferably in an amount of 10 to 25 weight %; brown rice syrup preferably in an amount of 2 to 8 weight %; chocolate liquor preferably in an amount of 1 to 4 weight %, cocoa butter preferably in an amount of 0.4 to 1.6 weight %; cocoa powder preferably in an amount of 4 to 12 weight %; fiber syrup SF75 preferably in an amount of 18 to 38 weight %, flax seed oil preferably in an amount of 1 to 3 weight %; salt preferably in an amount of 0.1 to 0.4 weight % and sugar preferably in an amount of 1 to 6 weight %.

In a refinement, the first olive-containing composition (sea salt version) incudes olives, olive oil, and sea salt. In a refinement, the first olive-containing composition (sea salt) includes lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; and thyme preferably in an amount of 0.1 to 0.5 weight %.

In a refinement, the second olive-containing composition (garlic version) incudes olives, olive oil, and garlic. In a refinement, the second olive-containing composition (garlic) includes garlic preferably in an amount of 0.1 to 0.6 weight %; lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; thyme preferably in an amount of 0.1 to 0.5 weight %.

In a refinement, the kale cracker composition includes kale, almonds, tapioca flour, and optionally sesame seeds. In another refinement, the kale cracker composition includes almonds preferably in an amount of 15 to 40 weight %; black pepper preferably in an amount of 0.1 to 0.4 weight %; chia seeds preferably in an amount of 3 to 10 weight %; chili pepper preferably in an amount of 0.4 to 1.2 weight %; cumin seeds preferably in an amount of 0.3 to 0.9 weight %; flax seeds preferably in an amount of 3 to 10 weight %; garlic preferably in an amount of 0.02 to 0.04 weight %; kale preferably in an amount of 2 to 6 weight %; oil (sun flower) preferably in an about of 2 to 7 weight %; onion (powder, minced) typically in an amount of 0.3 to 0.9 weight %; oregano preferably in an amount of 0.01 to 0.06 weight %; salt preferably in an amount of 1 to 4 weight %; sesame seeds preferably in an amount of 15 to 35 weight %; sugar (coconut) preferably in an amount of 1 to 5 weight %; tapioca flour preferably in an amount of 10 to 30 weight %; vinegar (coconut) preferably in an amount of 1 to 4 weight %; water (purified) preferably in an amount of 2 to 12 weight %; and yeast extract preferably in an amount of 0.3 to 1 weight %.

In another refinement, the kale cracker composition includes kale, flax seeds golden, sesame seeds, and sunflower seeds. In another refinement, the apple cider vinegar preferably in an amount 1 to 3 weight %; black pepper preferably in an amount of 0.4 to 1.3 weight %; cashews preferably in an amount of 4 to 13 weight %; dill weed preferably in an amount of 0.4 to 1.3 weight %; flax seeds golden preferably in an amount of 13 to 40 weight %; hemp seeds preferably in an amount of 0.7 to 2 weight %; kale preferably in an amount of 14 to 42 weight %; onion, white, dried, (powder, minced) preferably in an amount of 0.5 to 1.6 weight %; pumpkin seeds preferably in an amount of 0.7 to 2 weight %; salt (reg., kosher, sea salt) preferably in an amount of 0.7 to 2 weight %; Sesame seeds preferably in an amount of 2 to 8 weight %; sunflower seeds preferably in an amount of 10 to 30 weight %; and yeast extract preferably in an amount of 1 to 5 weight %.

In a refinement, the vegetable soup composition includes onions, tomatoes, spinach, green tree extract, optionally rice flour, optionally brown rice powder, optionally carrots, and optionally inulin, leeks, In a refinement, the vegetable soup composition includes basil (whole leaf, dried) preferably in an amount of 0.3 to 0.9 weight %; brown rice powder (whole grain) preferably in an amount of 3 to 12 weight %; carrot (dehydrated, puffed, powder, pieces) preferably in an amount of 4 to 14 weight %; green tea extract preferably in an amount of 0.02 to 0.06 weight %; inulin preferably in an amount of 5 to 15 weight %; leeks (granules −10+40) preferably in an amount of 1 to 5 weight %; oil (olive) preferably in an amount of 1 to 6 weight %; onion (powder, minced) preferably in an amount of 4 to 15 weight %;

parsley preferably in an amount of 0.3 to 0.8 weight %; red bell peppers preferably in an amount of 1 to 5 weight %; rice flour preferably in an amount of 18 to 50 weight %; salt preferably in an amount of 2 to 7 weight %; spinach (leaf, powder) preferably in an amount of 0.4 to 1.5 weight %; tomatoes (fruit powder, sun dried, granules) preferably in an amount of 4 to 14 weight %; yeast extract preferably in an amount of 0.5 to 1.8 weight %. In the vegetable soup composition and any of the compositions set forth herein having rice flour, the rice flour can be glutinous or non-glutinous, milled or unmilled.

In another refinement, the vegetable soup composition includes carrots, inulin, leeks, onions and rice flour. In a refinement, the vegetable soup composition includes basil, whole leaf, dried preferably in an amount of 0.3 to 1 weight %; carrot (dehydrated, puffed, powder, pieces) preferably in an amount of 4 to 12 weight %; inulin preferably in an amount of 6 to 18 weight %; leeks in an amount of 1 to 5 weight %; oil (olive) preferably in an amount of 1 to 3 weight %; Onion, white, dried, (powder, minced) preferably in an amount of 10 to 30 weight %; parsley preferably in an amount of 0.3 to 1 weight %; potato preferably in an amount of 1 to 5 weight %; red pepper preferably in an amount of 1 to 6 weight %; rice flour in an amount of 13 to 40 weight %; salt (reg., kosher, sea salt) in an amount of 4 to 12 weight %; spinach (leaf, powder) preferably in an amount of 0.2 to 1 weight %; and tomatoes, (fruit powder, sun dried granules) preferably in an amount of 3 to 13 weight %.

In a refinement, the mushroom soup composition includes mushrooms, green tea extract, optionally brown rice powder, optionally carrots, and optionally inulin. In a refinement, the mushroom soup composition includes brown rice powder (whole grain) preferably in an amount of 10 to 30 weight %; carrot (dehydrated, puffed, powder, pieces) preferably in an amount of 3 to 12 weight %; green tea extract preferably in an amount of 0.02 to 0.06 weight %; inulin preferably in an amount of 3 to 12 weight %; mushrooms (European mix, powder, pieces) preferably in an amount of 6 to 18 weight %; oil (olive) preferably in an amount of 1 to 6 weight %; onion preferably in an amount of powder, minced) preferably in an amount of 3 to 12 weight %; parsley preferably in an amount of 0.1 to 0.5 weight %; rice flour preferably in an amount of 18 to 50 weight %; salt preferably in an amount of 2 to 8 weight %; yeast extract preferably in an amount of 0.5 to 1.5 weight %.

In another refinement, the mushroom soup composition includes carrots, inulin, mushrooms, onions, and rice flour. In another refinement, the mushroom soup composition includes carrot (dehydrated, puffed, powder, pieces) preferably in an amount of 7 to 22 weight %; inulin preferably in an amount of 7 to 22 weight %; mushrooms (European mix), (powder & pieces) dehydrated preferably in an amount of 7 to 22 weight %; oil (olive) preferably in an amount of 0.6 to 2 weight %; Onion, white, dried, (powder, minced) preferably in an amount of 7 to 22 weight %; parsley preferably in an amount of 0.3 to 0.9 weight %; potato preferably in an amount of 0.6 to 2 weight %; rice flour preferably in an amount of 15 to 45 weight %; salt (reg., kosher, sea salt) preferably in an amount of 6 to 18 weight %; and yeast extract preferably in an amount of 0.7 to 2.2 weight %.

In a refinement, the tomato soup composition includes tomatoes, green tea extract, optionally inulin, and optionally onions. In a refinement, the tomato soup composition (new) includes basil (whole leaf, dried) preferably in an amount of 0.2 to 0.7 weight %; brown rice powder (whole grain) preferably in an amount of 1 to 5 weight %; green tea extract preferably in an amount of 0.02 to 0.06 weight %; inulin preferably in an amount of 7 to 20 weight %; oil (olive) preferably in an amount of 3 to 9 weight %; onion preferably (powder, minced) preferably in an amount of 4 to 12 weight %; parsley preferably in an amount of 0.1 to 0.6 weight %; rice flour preferably in an amount of 18 to 50 weight %; salt preferably in an amount of 2 to 9 weight %; tomatoes (fruit powder, sun dried, granules) preferably in an amount of 12 to 36 weight %; and yeast extract preferably in an amount of 0.5 to 3 weight %.

In another refinement, the tomato soup composition includes tomatoes, inulin, olives, onions, potatoes, and rice flour. In still another refinement, the tomato soup composition includes basil, whole leaf, dried preferably in an amount of 0.3 to 1 weight %; inulin preferably in an amount of 6 to 18 weight %; oil (olive) preferably in an amount of 4 to 14 weight %; onion, white, dried, (powder, minced) preferably in an amount of 8 to 24 weight %; parsley preferably in an amount of 0.3 to 0.9 weight %; potato preferably in an amount of 6 to 18 weight %; rice flour preferably in an amount of 9 to 27 weight %; salt (reg., kosher, sea salt) preferably in an amount of 4 to 14 weight %; tomatoes, (fruit powder, sun dried granules) preferably in an amount of 8 to 24 weight %; and yeast extract preferably in an amount of 0.7 to 2.2 weight %.

In a refinement, the quinoa-containing minestrone soup composition includes quinoa, green tea extract, optionally olive oil, optionally cabbage, optionally potatoes, optionally rice flour, and optionally tomatoes and optionally no tumeric. In a refinement, the quinoa-containing minestrone soup composition includes basil (whole leaf, dried preferably in an amount of 0.7 to 2 weight %; broccoli powder preferably in an amount of 0.6 to 2 weight %; cabbage white (flakes) preferably in an amount of 3 to 10 weight %; carrot (dehydrated, puffed, powder, pieces) preferably in an amount of 3 to 10 weight %; celery preferably in an amount of 1 to 4 weight %; celery seeds (powder) preferably in an amount of 0.07 to 0.2 weight %; garlic preferably in an amount of 0.7 to 2 weight %; green tea extract preferably in an amount of 0.02 to 0.06 weight %; inulin preferably in an amount of 1 to 5 weight %; leeks (granules –10+40), preferably in an amount of 0.7 to 2 weight %; oil (olive) preferably in an amount of 0.6 to 2 weight %; onion (powder, minced) preferably in an amount of 2 to 8 weight %; peas preferably in an amount of 3 to 10 weight %; potato preferably in an amount of 7 to 20 weight %; quinoa preferably in an amount of 7 to 20 weight %; rice flour preferably in an amount of 7 to 20 weight %; salt, preferably in an amount of 1 to 6 weight %; spinach (leaf, powder) preferably in an amount of 0.5 to 2 weight %; tomatoes (fruit powder, sun dried, granules) preferably in an amount of 2 to 6 weight %; yeast extract preferably in an amount of 0.6 to 2 weight %; zucchini (powder, diced) preferably in an amount of 2 to 8 weight %.

In another refinement, the quinoa-containing minestrone soup includes quinoa, cabbage, potatoes, and rice flour. In still another refinement, the quinoa-containing minestrone soup includes basil, whole leaf, dried preferably in an amount of 0.7 to 2.2 weight %; broccoli powder preferably in an amount of 0.7 to 2.2 weight %; cabbage white (flakes) preferably in an amount of 0.6 to 2.2 weight %; carrot (dehydrated, puffed, powder, pieces) preferably in an amount of 3 to 10 weight %; celeriac preferably in an amount of 2 to 6 weight %; celery seeds powder preferably in an amount of 0.6 to 1.8 weight %; garlic preferably in an amount of 1 to 3 weight %; Onion, white, dried, (powder, minced) preferably in an amount of 3 to 9 weight %; peas preferably in an amount of 3 to 10 weight %; potato preferably in an amount of 6 to 20 weight %; quinoa preferably in an amount of 8 to 23 weight %; rice flour preferably in an amount of 7 to 22 weight %; salt (reg., kosher, sea salt) preferably in an amount of 2 to 7 weight %; savoy cabbage preferably in an amount of 3 to 10 weight %; spinach (leaf, powder) preferably in an amount of 0.7 to 2.2 weight %; turmeric preferably in an amount of 0.6 to 1.8 weight %; yeast extract preferably in an amount of 3 to 10 weight %; and zucchini (powder, diced) preferably in an amount of 1 to 5 weight %.

In a refinement, the bean-containing minestrone soup composition includes white beans (e.g., great northern beans), great tea extract, optionally cabbage, and optionally potatoes. In a refinement, the bean-containing minestrone soup composition includes beans (great northern) preferably in an amount of 3 to 10 weight %; cabbage white (flakes) preferably in an amount of 2 to 8 weight %; carrot (dehydrated, puffed, powder, pieces) preferably in an amount of 2 to 8 weight %; celery preferably in an amount of 1 to 4 weight %; green tea extract preferably in an amount of 0.02 to 0.06 weight %; inulin preferably in an amount of 2 to 10 weight %; leeks (granules –10+40) preferably in an amount of 2 to 7 weight %; oil (olive) preferably in an amount of 2 to 7 weight %; onion (powder, minced) preferably in an amount of 2 to 7 weight %; parsley preferably in an amount of 0.2 to 1 weight %; peas preferably in an amount of 3 to 9 weight %; potato preferably in an amount of 15 to 45 weight %; rice flour preferably in an amount of 6 to 18 weight %; salt preferably in an amount of 2 to 8 weight %; spinach (leaf, powder) preferably in an amount of 0.5 to 1.5 weight %; tomatoes (fruit powder, sun dried, granules) preferably in an amount of 2 to 7 weight %; and yeast extract preferably in an amount of 0.5 to 1.5 weight %.

In a refinement, the bean-containing minestrone soup composition includes brown beans, carrots, peas, potato, and rice flour. In another refinement, the bean-containing minestrone soup composition includes carrot (dehydrated, puffed, powder, pieces) preferably in an amount of 4 to 14 weight %; celeriac preferably in an amount of 1 to 5 weight %; celery preferably in an amount of 0.5 to 1.6 weight %; leeks preferably in an amount of 2 to 8 weight %; oil (olive) preferably in an amount of 2 to 8 weight %; Onion, white, dried, (powder, minced) preferably in an amount of 3 to 10 weight %; parsley preferably in an amount of 0.5 to 1.5 weight %; peas preferably in an amount of 5 to 18 weight %; potato preferably in an amount of 8 to 24 weight %; rice flour preferably in an amount of 5 to 18 weight %; salt (reg., kosher, sea salt) preferably in an amount of 4 to 14 weight %; spinach (leaf, powder) preferably in an amount of 0.5 to 1.5 weight %; tomatoes, (fruit powder, sun dried granules) preferably in an amount of 0.9 to 2.8 weight %; turmeric preferably in an amount of 0.3 to 1.2 weight %; and yeast extract preferably in an amount of 0.5 to 1.5 weight %.

In a refinement, the pumpkin soup composition includes pumpkin, green tree extract, optionally rice flour, optionally carrots, and optionally brown rice powder. In a refinement, the pumpkin soup composition includes (new) includes brown rice powder (whole grain) preferably in an amount of 3 to 9 weight %; carrot (dehydrated, puffed, powder, pieces) preferably in an amount of 2 to 8 weight %; green tea extract preferably in an amount of 0.02 to 0.06 weight %; inulin preferably in an amount of 2 to 10 weight %; oil (olive) preferably in an amount of 1 to 7 weight %; onion (powder, minced) preferably in an amount of 1.0 to 3 weight %; pumpkin powder preferably in an amount of 20 to 60 weight %; rice flour preferably in an amount of 15 to 45 weight %;

salt preferably in an amount of 2 to 10 weight %; and yeast extract preferably in an amount of 0.3 to 1 weight %.

In a refinement, the first vegetable broth includes carrots, maltodextrin, celery, spinach, and tomatoes. In a refinement, the first vegetable broth includes carrot (dehydrated, puffed, powder, pieces) preferably in an amount of 6 to 18 weight %; celery preferably in an amount of 3 to 10 weight %; garlic preferably in an amount of 3 to 10 weight %; maltodextrin preferably in an amount of 8 to 25 weight %; oil (canola) preferably in an amount of 0.5 to 2 weight %; onion (powder, minced) preferably in an amount of 6 to 18 weight %; parsley preferably in an amount of 3 to 10 weight %; potato preferably in an amount of 1 to 3 weight %; salt preferably in an amount of 7 to 21 weight %; spinach (leaf, powder) preferably in an amount of 3 to 10 weight %; tomatoes (fruit powder, sun dried, granules) preferably in an amount of 6 to 18 weight %; and yeast extract preferably in an amount of 1 to 6 weight %.

In a refinement, the second vegetable broth (chicken flavoring) includes carrots, chicken flavoring, maltodextrin, celery, spinach, soy lecithin, and tomatoes. In a refinement, the second vegetable broth composition includes carrot (dehydrated, puffed, powder, pieces) preferably in an amount of 3 to 10 weight %; celery preferably in an amount of 3 to 12 weight %; garlic preferably in an amount of 3 to 9 weight %; maltodextrin preferably in an amount of 8 to 25 weight %; oil (canola) preferably in an amount of 0.5 to 2 weight %; onion preferably in an amount of powder, minced) preferably in an amount of 3 to 12 weight %; parsley preferably in an amount of 3 to 10 weight %; potato preferably in an amount of 1 to 6 weight %; salt preferably in an amount of 8 to 25 weight %; soy lecithin preferably in an amount of 0.5 to 3 weight %; spinach (leaf, powder) preferably in an amount of 3 to 12 weight %; tomatoes (fruit powder, sun dried, granules) preferably in an amount of 6 to 18 weight %; xanthan gum preferably in an amount of 0.5 to 4 weight %; and yeast extract preferably in an amount of 4 to 12 weight %.

In a refinement, the energy drink composition includes glycerin preferably in an amount of 20 to 60 weight %; water (purified) preferably in an amount of 40 to 80 weight %.

In a refinement, the tea composition that includes spearmint includes spearmint leaves organic preferably in an amount of 70 to 100 weight %.

In a refinement, the tea composition that includes lemon and spearmint includes lemon myrtle organic preferably in an amount of 3 to 12 weight %; lemon peel organic preferably in an amount of 10 to 25 weight %; spearmint leaves organic preferably in an amount of 50 to 95 weight %.

In a refinement, the tea composition that includes hibiscus includes hibiscus tea leaves organic preferably in an amount of 80 to 100 weight %.

In a refinement, the algal oil composition includes schizocatrium algae oil (DHA Omega-3) preferably in an amount of 80 to 100 weight %.

In a refinement, the nutrient replenishment composition (NR-1) includes beet root powder, calcium carbonate, carrots, collard leaf, kale leaf, and tomatoes. In a refinement, the nutrient replenishment composition (NR-1) includes ascorbic acid preferably in an amount of 1 to 3 weight %; beet root powder preferably in an amount of 6 to 20 weight %; beta carotene preferably in an amount of 0.05 to 0.15 weight %; calcium carbonate preferably in an amount of 6 to 20 weight %; carrot (dehydrated, puffed, powder, pieces) preferably in an amount of 6 to 20 weight %; cholecaliciferol preferably in an amount of 0.00 weight %; chromuim Picolinate preferably in an amount of 0.00 weight %; collard leaf powder preferably in an amount of 6 to 20 weight %; cupric sulfate preferably in an amount of 0.01 to 0.06 weight %; cyanocobalamin, 0.00; Dl-alpha tocopherol acetate preferably in an amount of 0.3 to 1 weight %; ferrous fumarate preferably in an amount of 0.2 to 1 weight %; folic acid preferably in an amount of 0.00 weight %; kale leaf preferably in an amount of 6 to 20 weight %; magnesium stearate preferably in an amount of 1 to 6 weight %; manganese sulfate preferably in an amount of 0.04 to 0.08 weight %; niacinamide preferably in an amount of 0.3 to 1 weight %; pantothenic acid preferably in an amount of 0.1 to 0.6 weight %; phytonadione preferably in an amount of 0.00 weight %; potassium iodine preferably in an amount of 0 weight %; pyriodoxine HCl preferably in an amount of 0.03 to 0.1 weight %; riboflavin preferably in an amount of 0.02 to 0.1 weight %; sodium molybdate preferably in an amount of 0.00 weight %; sodium selenate preferably in an amount of 0.00 weight %; spinach (leaf, powder) preferably in an amount of 6 to 20 weight %; thiamine mononitrate preferably in an amount of 0.02 to 0.1 weight %; tomatoes (fruit powder, sun dried, granules) preferably in an amount of 6 to 20 weight %; tribasic calcium phosphate preferably in an amount of 0.5 to 2 weight %; and zinc oxide preferably in an amount of 0.2 to 0.8 weight %.

In a variation, the each of the components of the fasting mimicking diet package and therefore the fasting mimicking diet, is substantially gluten free (e.g., each component has less than 20 ppm gluten) or very low gluten (e.g., each component has 20-100 ppm). In other variations, each of the components are provided in a serving size from 20 to 60 g. In other variations, the nut-containing nutrition bar is provided in a serving size from 30 to 60 g; cocoa-containing nutrition bar is provided in a serving size from 15 to 40 g; the olive containing composition (sea salt version) in a serving size from 10 to 20 g; the olive containing composition (garlic version) in a serving size from 10 to 20 g; kale cracker composition is provides in a serving size from 30 to 60 g; In another variation, the kale cracker compositions are provided in a serving size from 20 to 50 g; the vegetable soup compositions are provided in a serving size from 20 to 50 g; the mushroom soup compositions are provided in a serving size from 20 to 50 g; the tomato soup compositions are provided in a serving size from 20 to 50 g; the bean-containing minestrone soup compositions are provided in a serving size from 20 to 50 g; the quinoa-containing minestrone soup compositions are provided in a serving size from 20 to 50 g; the pumpkin soup compositions are provided in a serving size from 20 to 50; the first vegetable both compositions are provided in a serving size from 5 to 15; the second vegetable both compositions are provided in a serving size from 3 to 15; and Energy Drink composition is provided in serving size of of 1 to 5 oz.

FIGS. 7A-H provide nutritional information for each of the meal components. It should be appreciated that variations of these values can vary by +/−30 percent. In other variations, the meal components are provide is sufficient amounts to meet the caloric and nutritional requirements in these figures.

The table set forth below provides a schedule of administration for two FMD meal plans to be administered to a subject. The Prolon Meal plan is useful for weight loss, treating or preventing hypertension, metabolic disease, diabetes, and the like. The Chemolieve meal plan is useful for alleviating the side effect of chemotherapy. Therefore, the diet packages set forth herein can include instruction providing the schedules and instructions for administering the FMD to treat various conditions as set forth in the methods below.

Table of Meal Schedules

| COMPONENTS (single servings) | MEAL PLAN - PROLON US | | | | | MEAL PLAN CHEMOLIEVE US | | | | |
|---|---|---|---|---|---|---|---|---|---|---|
| | DAY 1 | DAY 2 | DAY 3 | DAY 4 | DAY 5 | DAY 1 | DAY 2 | DAY 3 | DAY 4 | DAY 5 |
| nut-containing nutrition bar (L-Bar Nut based) | 2 | 1 | 1 | 1 | 1 | 1 | — | — | — | 1 |
| cocoa-containing nutrition bar (L-Bar ChocoCrisp) - .83 oz. | 1 | 1 | — | 1 | — | — | — | — | — | — |
| First olive-containing composition (Sea Salt) - 0.73 oz | 1 | 1 | — | 1 | — | — | — | — | — | — |
| Second olive-containing composition (Garlic) - 0.73 oz | — | 1 | — | 1 | — | — | — | — | — | — |
| kale cracker composition, (35 g) | 1 | — | 1 | — | 1 | 1 | 1 | — | — | — |
| vegetable soap composition | — | — | — | 1 | — | 1 | — | — | 1 | — |
| mushroom soap composition | — | 1 | — | — | — | — | 1 | — | — | — |
| tomato soap composition | 1 | — | 1 | — | 1 | 1 | — | — | — | 1 |
| quinoa-containing minestrone soup composition | — | 1 | — | 1 | — | — | — | — | — | — |
| bean-containing minestrone soup composition | 1 | — | 1 | — | 1 | — | — | — | — | — |
| pumpkin soup composition, | — | — | — | — | — | — | — | 1 | — | — |
| First vegetable broth composition | — | — | — | — | — | — | — | 1 | — | 1 |
| Second vegetable broth composition (chicken) | — | — | — | — | — | — | 1 | — | 1 | — |
| Energy Drink | — | 1 | 1 | 1 | 1 | 1 | 1 | — | — | — |
| Tea - Spearmint | 1 | 1 | 1 | 1 | 1 | 1 | 1 | 1 | 1 | 1 |
| Tea - Lemon Spearmint | 1 | 1 | 1 | 1 | 1 | 1 | 1 | 1 | 1 | 1 |
| Tea - Hibiscus | — | 2 | 2 | 2 | 2 | — | — | — | — | — |
| Algal oil | 1 | — | — | — | 2 | 2 | — | — | — | 1 |
| NR-1 | 2 | 1 | 1 | 1 | 1 | 2 | 1 | 1 | 1 | 1 |

In another embodiment, a method for inducing differential effects on disease factors and markers associated with aging is provided. This method includes a step of identifying a subject in need of modifying disease factors and markers associated with aging. Expression of the factors and marker might be decreased or increased depending on which direct results in a health benefit. The fasting mimicking diet provided by the diet packages set forth above is administered to a subject for a predetermined period of time as set forth above. Examples of such disease factors and markers are insulin-like growth factor-1, blood glucose, systolic or diastolic blood pressure insulin-like growth factor-1, blood glucose, systolic blood pressure, diastolic blood pressure, cholesterol, CRP, triglycerides, or abdominal/visceral fats.

In another embodiment, a method of promoting and inducing beneficial long-lasting effects on disease factors and markers associated with aging is provided. This method includes a step of identifying a subject in need of modifying disease factors and markers associated with aging. Expression of the factors and marker might be decreased or increased depending on which direct results in a health benefit. The fasting mimicking diet provided by the diet packages set forth above is administered to a subject for a predetermined period of time as set forth above. Examples of such disease factors and markers are insulin-like growth factor-1, blood glucose, systolic blood pressure, diastolic blood pressure, cholesterol, CRP, triglycerides, or abdominal/visceral fats.

In still another embodiment, a method for promoting and inducing stem-cell based regeneration of multiple organs and systems is provided. This method includes a step of identifying a subject in need of promoting and inducing stem-cell based regeneration of multiple organs and systems. The fasting mimicking diet provided by the diet packages set forth above is administered to a subject for a predetermined period of time as set forth above. Examples of stem-cell based regeneration of multiple organs and systems include, but are not limited to, neurogenesis, hematopoiesis, or promotion of pancreatic beta-cells.

In still another embodiment, a method for promoting and inducing stem cell-based rejuvenation of multiple organs and systems is provided. This method includes a step of identifying a subject in need of promoting and inducing stem-cell based rejuvenation of multiple organs and systems. The fasting mimicking diet provided by the diet packages set forth above is administered to a subject for a predetermined period of time as set forth above. Examples of stem cell-based regeneration of multiple organs and systems include, but are not limited to, neurogenesis, hematopoiesis, or promotion of pancreatic beta-cells.

The following examples illustrate the various embodiments of the present invention. Those skilled in the art will recognize many variations that are within the spirit of the present invention and scope of the claims.

We report the results of a randomized controlled trial of 100 subjects, 71 of whom completed 3 cycles of the FMD either in a randomized phase (N=39) or after being crossed over from a control diet group to the FMD group (N=32). We evaluated the effects of the FMD on risk factors and markers for aging, cancer, metabolic syndrome and cardiovascular diseases in generally healthy participants ranging from 20 to 70 years of age.

Baseline Data for all Subjects.

From April 2013 until July 2015, 100 study participants were randomized and assigned to either arm 1 (N=48) or arm 2 (N=52). At enrollment, independent of whether they completed the trial or not, subjects in the two arms were comparable for age, sex, race, and body weight (FIG. 8, Table 1). Hispanics (27%) were underrepresented in the study population in comparison to their representation (~45%) in the greater Los Angeles area (California, USA) (42). The participants in control arm 1 were asked to continue their normal diet for 3 months, while participants in arm 2 started the FMD intervention. Two participants withdrew from arm 1 due to scheduling conflicts before completion of the informed consent. In the randomized comparison (FIG. 1B), 18 participants or 5 of 48 (10%) in the control arm and 13 of 52 participants in the FMD arm (25%), were excluded or withdrew from the study. Of the 48 subjects enrolled in the control arm, 2 withdrew because of scheduling conflicts, 2 due to unspecified personal issues, and one for unknown reasons. Six of the 52 subjects enrolled in the FMD arm withdrew from the study due to scheduling conflicts, 5 because of unspecified personal issues, and 2 participants were excluded from the study because of non-compliance to the FMD protocol.

Adverse Effects and Safety.

Figure 4:
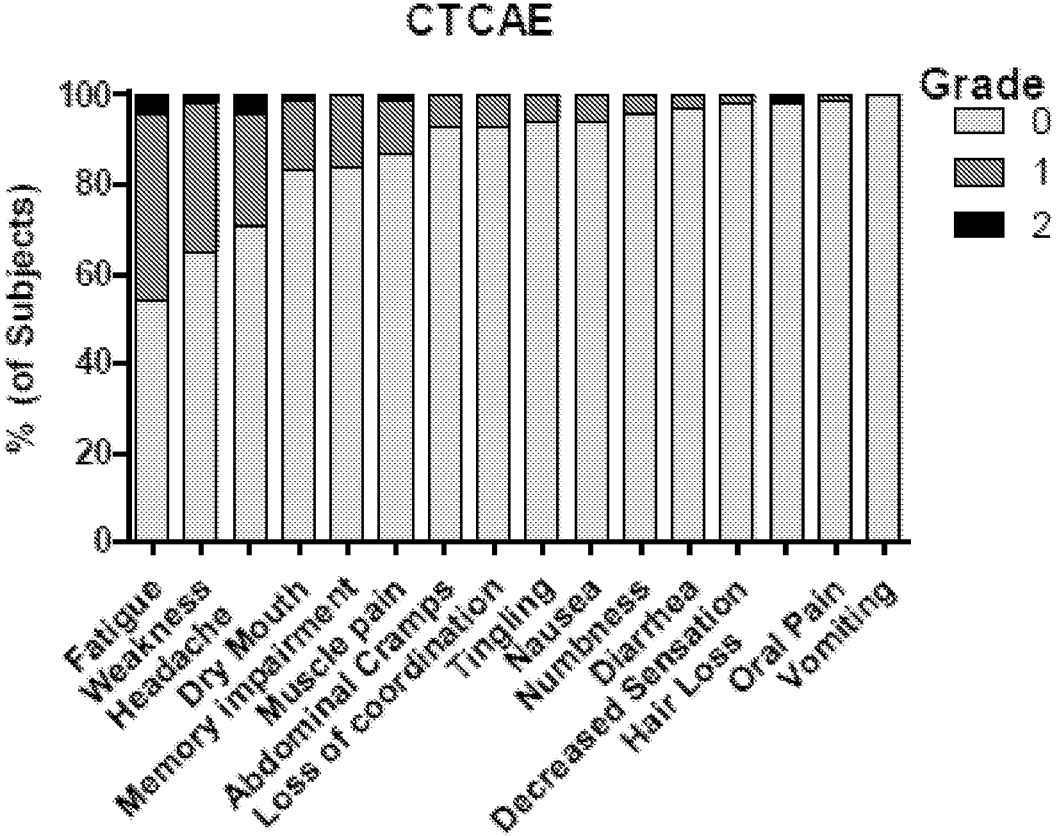

Following the Common Terminology Criteria for Adverse Events (CTCAE, v4.0), 54% to 100% (depending on the adverse event) of the participants reported no adverse effects during the FMD cycles (FIG. 4). The most common self-reported grade 1 (mild) or grade 2 (moderate) symptoms experienced by the participants were fatigue, weakness and headaches. No adverse effects of grade 3 or higher were reported. A comprehensive metabolic panel that measured changes in metabolic markers and liver and kidney function showed no negative effects of 3 cycles of the FMD (FIG. 12, Table 5). In summary, after 3 cycles of the FMD subjects reported only some mild and very few moderate side effects.

Baseline Risk Factors and Metabolic Markers: Comparison of Randomized Control and FMD Subjects Who Completed the Trial.

At baseline, there were no significant differences in metabolic markers or risk factors for age-related diseases and conditions between the subjects who successfully completed the randomized trial in arm 1 (normal diet) and arm 2 (FMD), including body weight (p=0.39), BMI (p=0.24), total body fat (p=0.11), trunk fat (p=0.087), lean body mass (p=0.15), waist circumference (p=0.34), fasting glucose (p=0.55), IGF-1 (p=0.51), systolic and diastolic blood pressure (p=0.60 and p=0.91, respectively), triglycerides (p=0.21) and C-reactive protein (p=0.28). The notable exception was that total cholesterol (p=0.014) and low-density lipoprotein (p=0.024), but not high-density lipoprotein (p=0.99), were significantly lower at baseline for subjects who were enrolled and completed arm 2 (FIG. 9, Table 2). In summary, the values for disease markers and risk factors at baseline were comparable between the control diet and FMD groups, with the exception of total and LDL cholesterol.

Changes in Risk Factors and Metabolic Markers: Comparison of Randomized Control and FMD Groups.

Figures 1, 2, 6B:
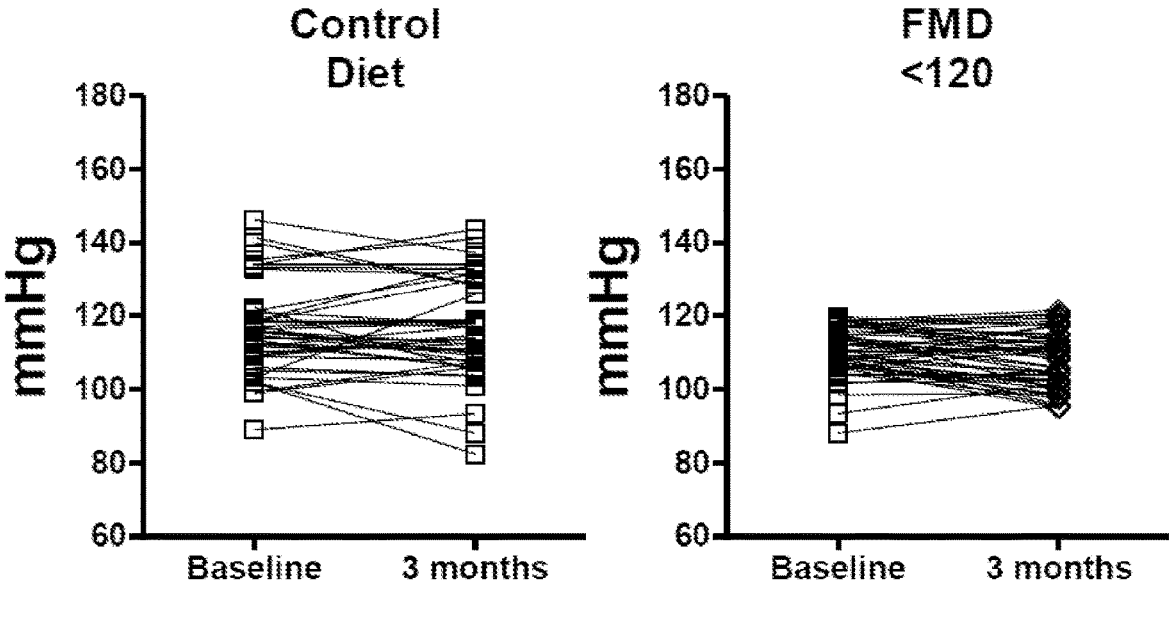
Figures 3, 6B:
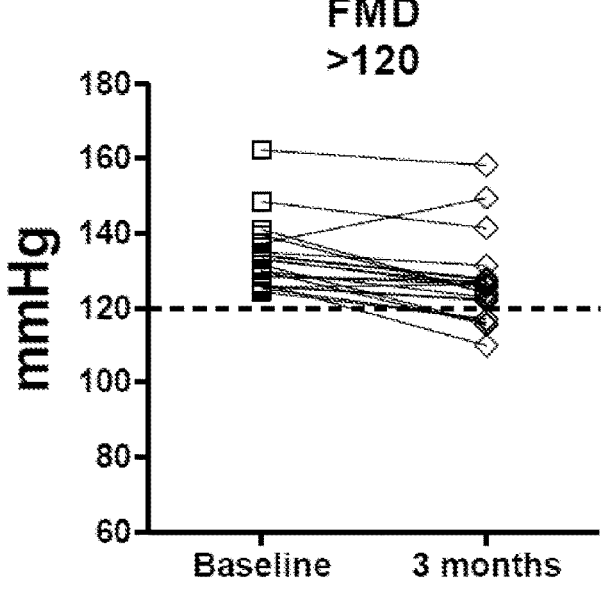
Figure 6C:
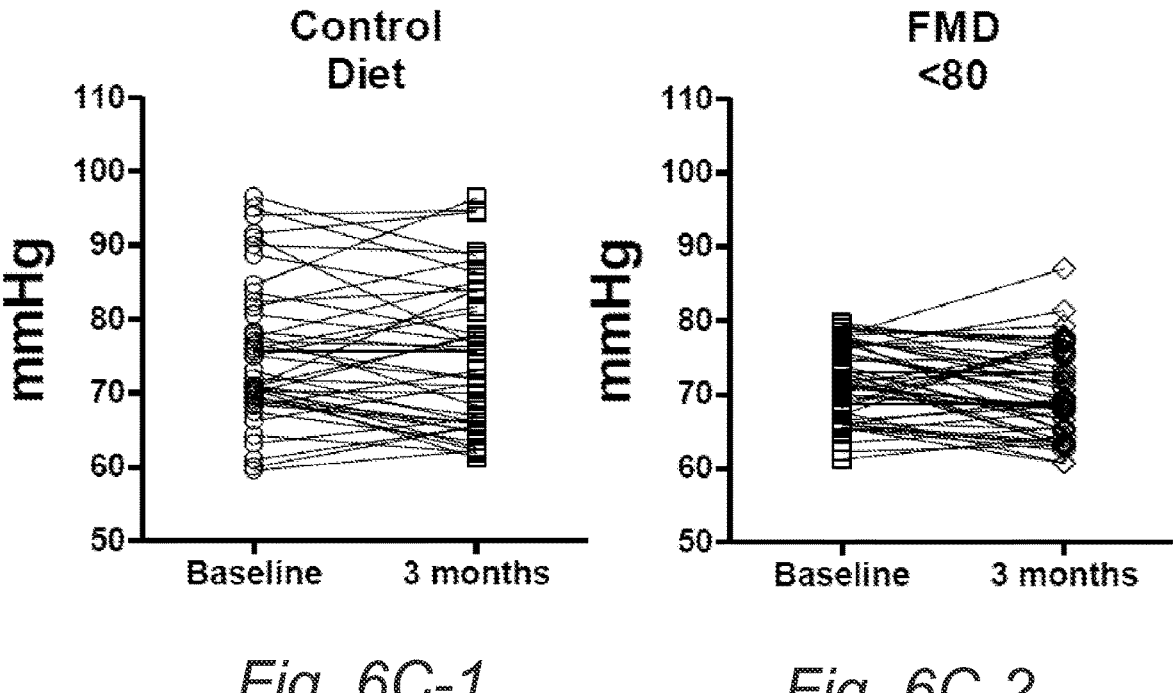
Figure 3:
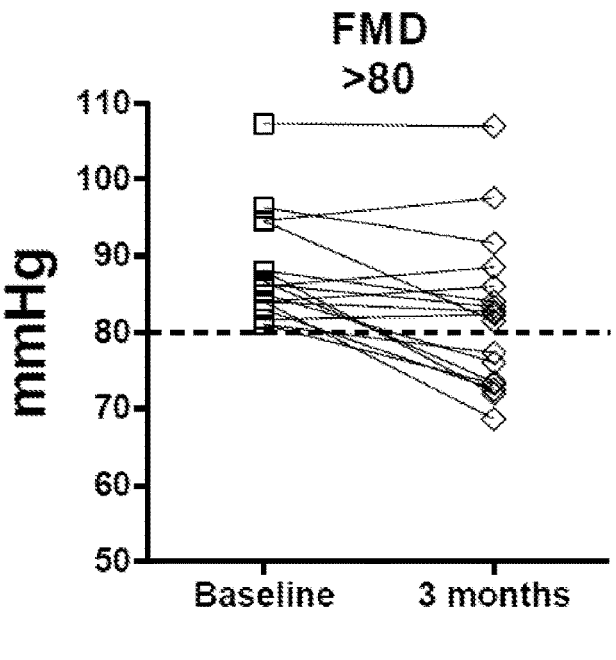
Figure 6D:
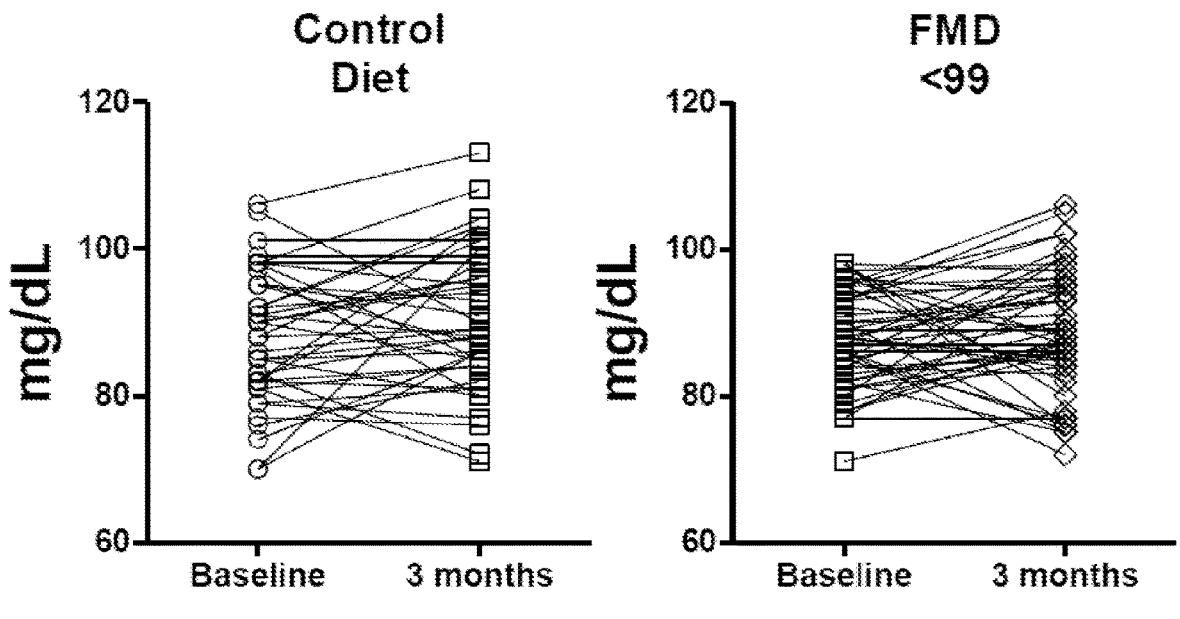
Figure 3:
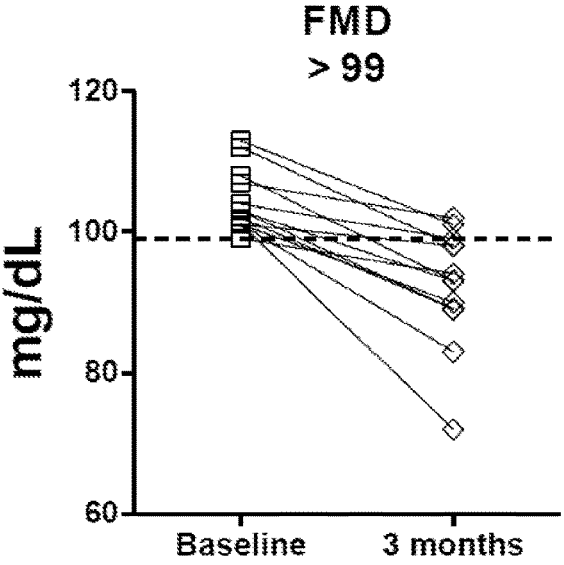
Figures 3, 6E:
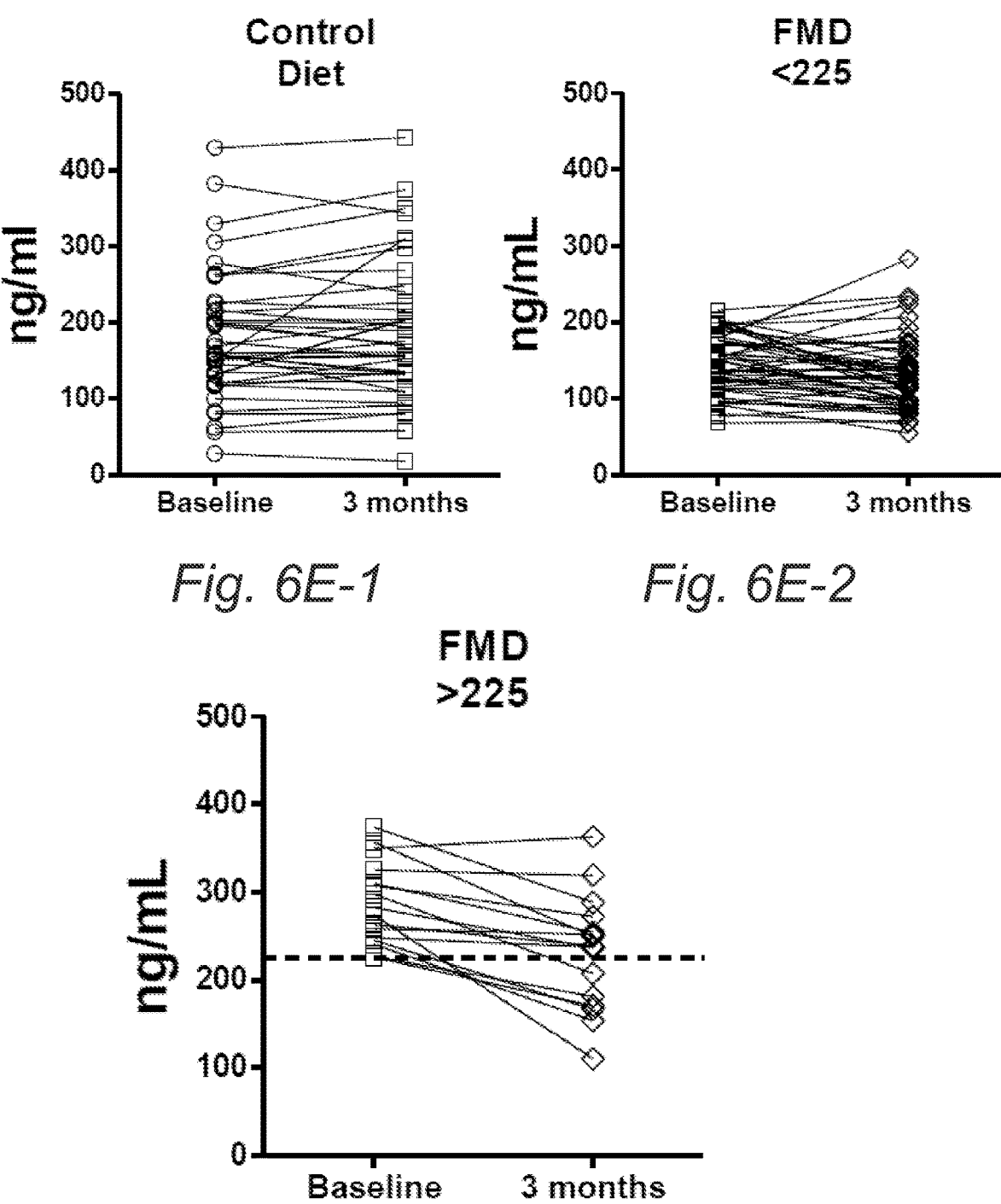
Figures 1, 2, 3, 6F:
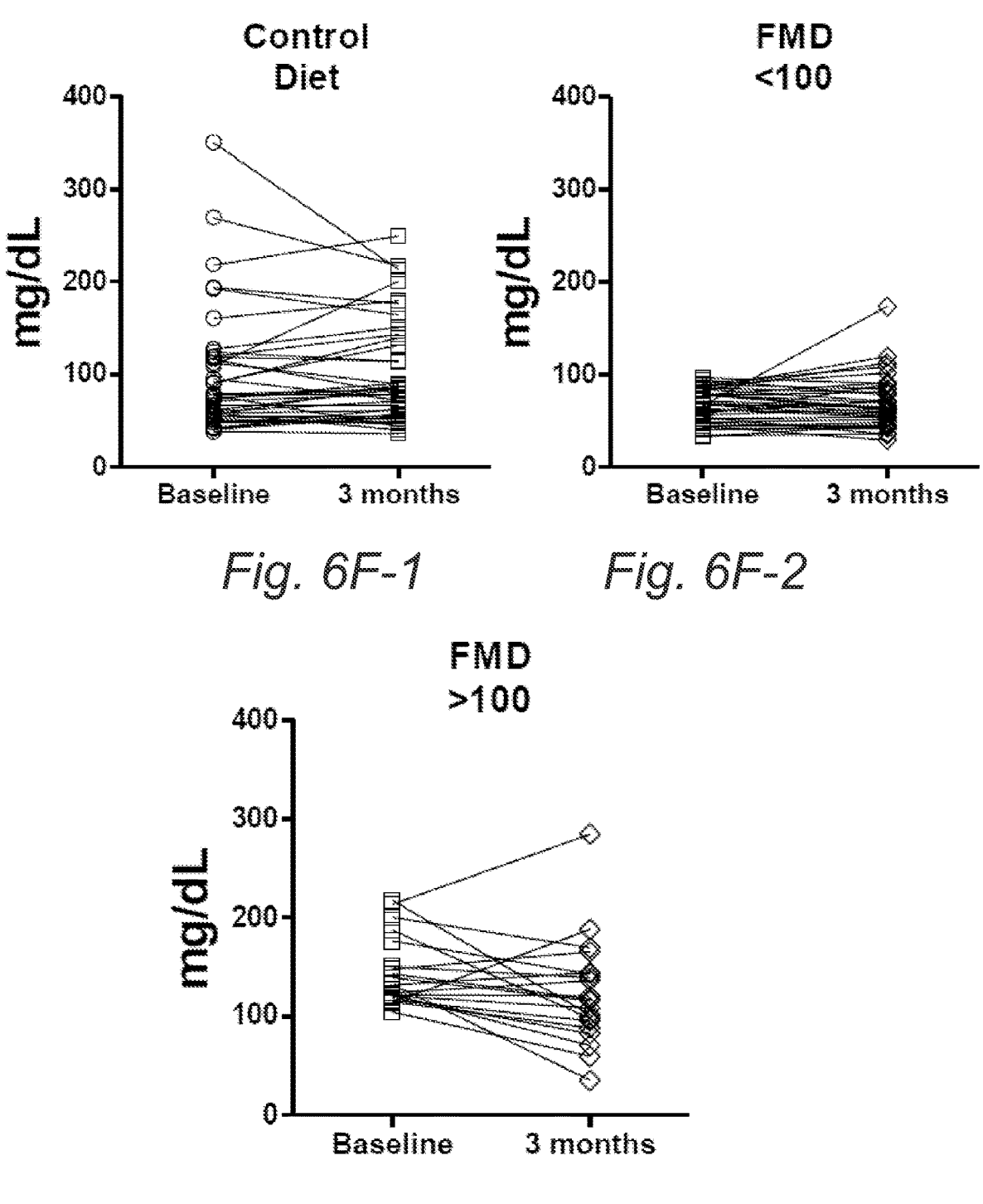
Figure 6G:
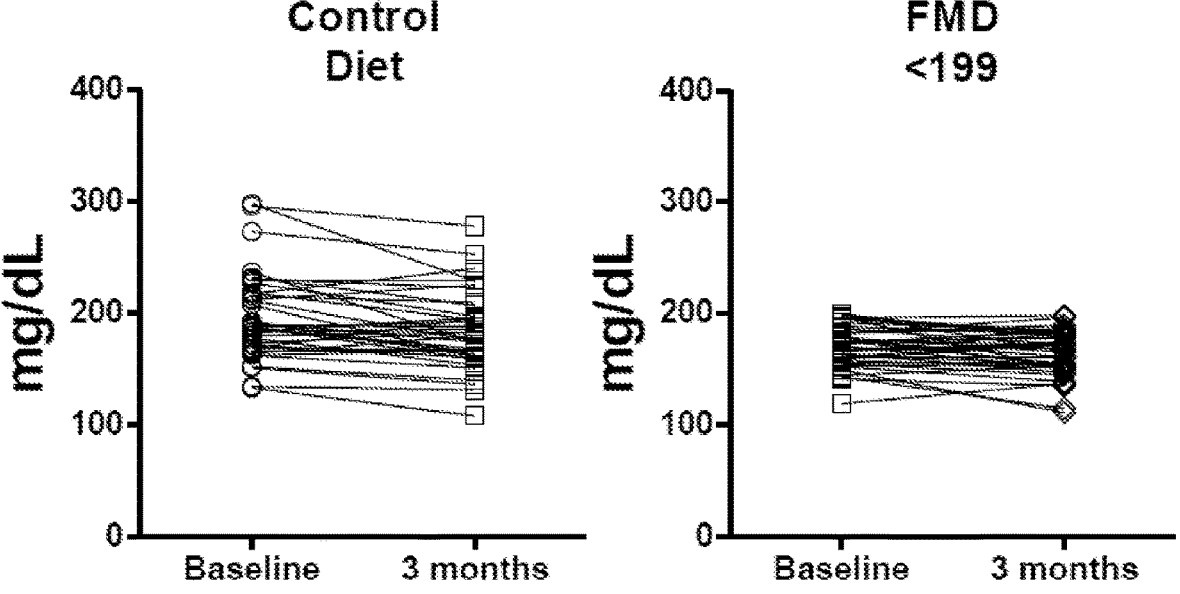
Figure 3:
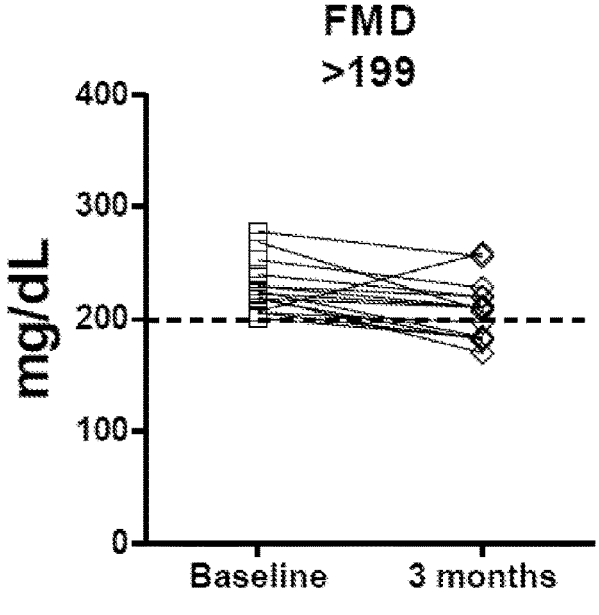
Figures 1, 2, 6H:
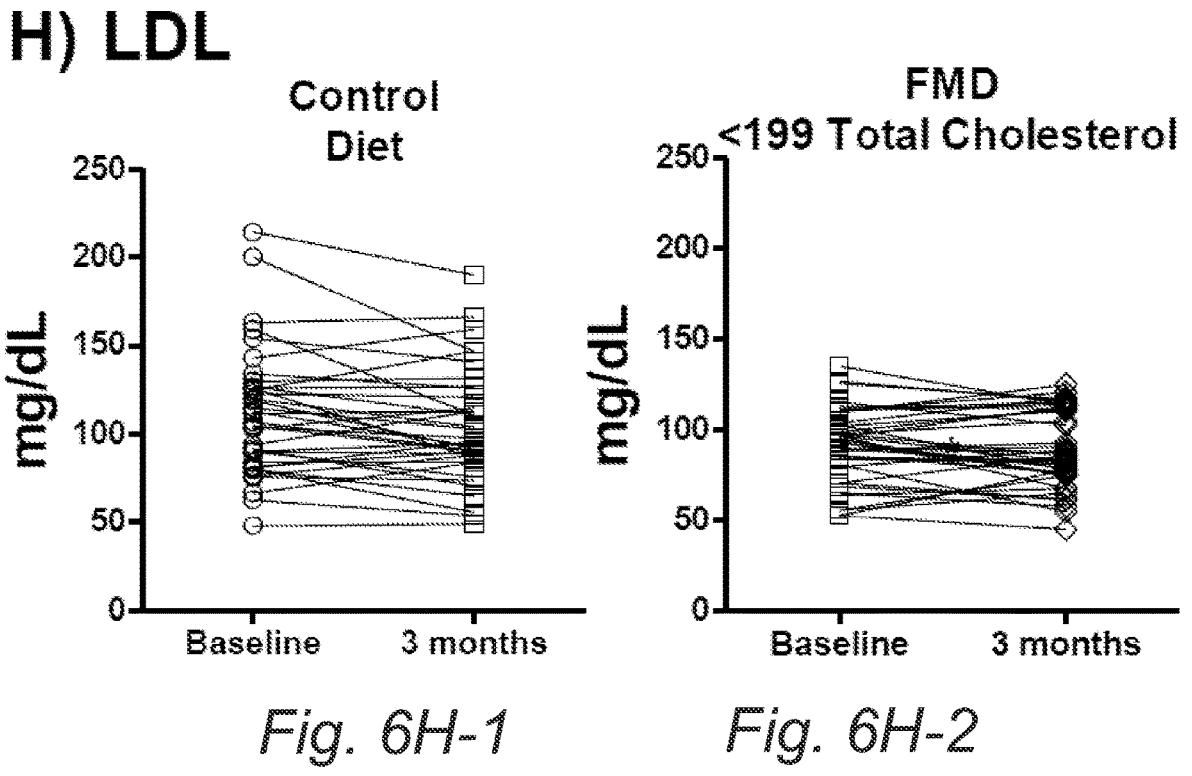
Figures 3, 6H:
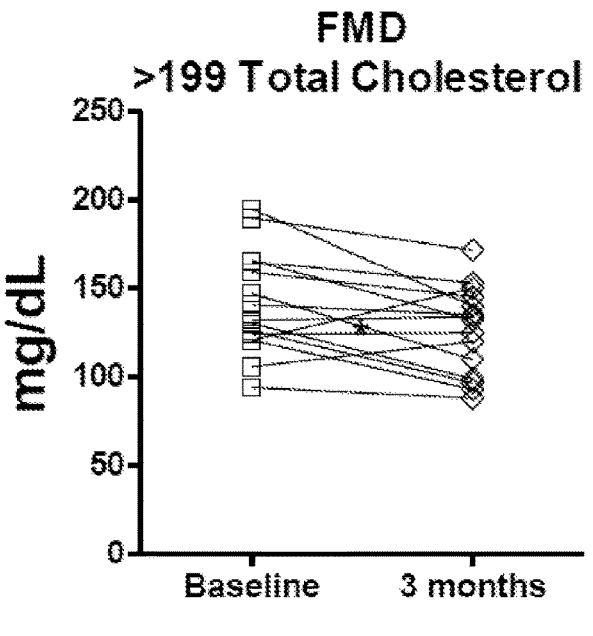
Figures 1, 2, 3, 6J:
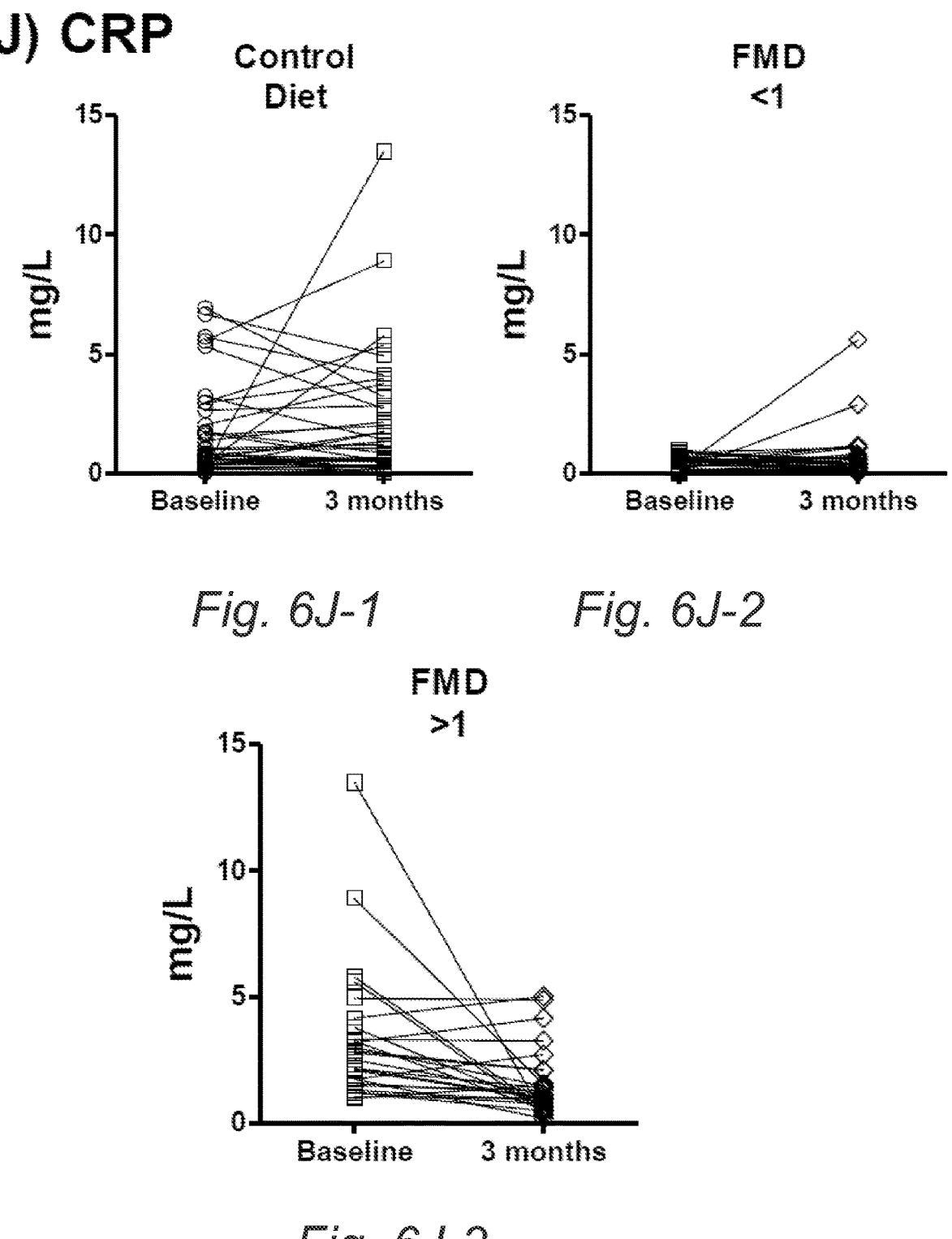

Next, we evaluated the effects of the FMD by assessing the changes in marker/risk factor values between baseline and 5-7 days following the end of the third cycle of the FMD and compared them to those occurring in the control arm within the same 3-months period (FIG. 2 and Tables 2 (FIG. 9) and 6 (FIG. 13)). Participants in the FMD arm (arm 2) lost on average 2.6±2.5 kg (±SD) (p<0.0001) of weight, which was accompanied by a reduction in total body fat (absolute values and relative volume % of total mass) and trunk fat (absolute values) (Tables 2 (FIG. 9), 6 (FIG. 13)). Subjects on the control diet did not lose body weight (0.1±2.1 kg). After controlling the false discovery rate of 0.05 between the control and FMD groups, no change in the percentage of lean body mass was observed (relative to the total mass; p=0.07), although absolute lean body mass was reduced in arm 2 (p=0.004) (Tables 2 (FIG. 9), Table 6 (FIG. 13)). Waist circumference measured after 3 FMD cycles was reduced by 4.1±5.2 cm (p=0.0035 between groups). The FMD cycles also resulted in a decrease in IGF-1 concentrations of 21.7±46.2 ng/mL (p=0.0017 between groups). Systolic blood pressure was reduced by 4.5±6.0 mmHg (p=0.023 between groups) and diastolic blood pressure was reduced by 3.1±4.7 mmHg (p=0.053 between groups). Fasting glucose (p=0.27), triglycerides (p=0.27), cholesterol (total p=0.81; LDL p=0.50; HDL p=0.90) and the acute-phase inflammatory marker C-reactive protein (CRP; p=0.27) did not differ significantly between groups. A graphical summary of these data is presented in FIG. 2. In conclusion, 3 cycles of the FMD reduced body weight, trunk and total body fat, blood pressure and IGF-1 in comparison to a standard diet.

Changes in Risk Factors and Metabolic Markers of Age-Related Diseases and Conditions: Observational Pre Post FMD Comparison.

Figure 5:
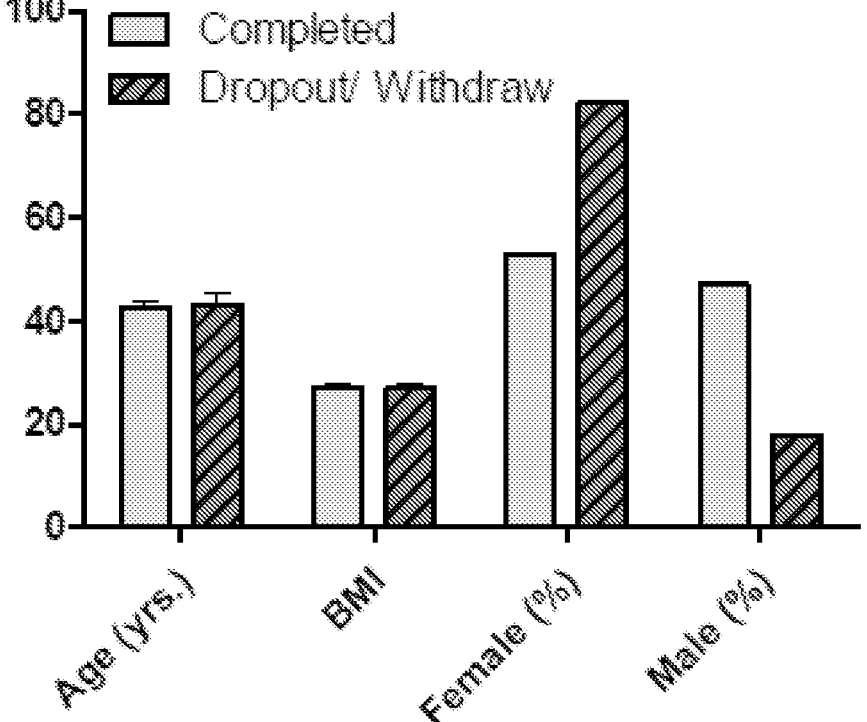

After 3 months, 43 subjects from the control arm were crossed over to the FMD intervention. 11 (26%) of these subjects withdrew before completing 3 FMD cycles (FIG. 1B). Five of these participants withdrew due to scheduling issues and 2 subjects opted to leave the trial for unspecific personal reasons. We also excluded 4 participants based on non-adherence to the FMD protocol. The causes for withdrawal/exclusion were comparable between the arms. Considering both FMD treatment arms, 24 of the 95 participants (25%) were excluded or withdrew from the study prior to completion of the 3 FMD cycles (arm 2 N=13 FMD and arm 1 N=11 after FMD crossover) due to scheduling conflicts (total N=11; arm 2 N=6 FMD and arm 1 N=5 after FMD crossover), personal issues (total N=7; arm 2 N=5 FMD; arm 1 N=2 after FMD crossover), or dislike of the diet and/or non-adherence to the dietary protocol (total N=6; arm 2 N=2 FMD; arm 1 N=4 after FMD crossover) (FIG. 1B). The 25% dropout rate for participants during the FMD is higher than the 10% dropout rate observed during control diet in arm 1, but this is expected considering that subjects in control diet group only dropped out because of scheduling conflicts since they were was allowed to remain on their own diet. 95 subjects (95%) completed 1 cycle and 71 (71%) completed 3 cycles of the FMD. Compared to the 71 participants who completed the 3 FMD cycles in arms 1 and 2, the 24 subjects who dropped out were not different in age (42.5±11.6 vs. 43.3±13.1 years) or BMI (27.1±4.9 vs. 26.9±4.7) but were mostly female (18% male vs. 82% female, p=0.0045 Fisher's exact test; FIG. 5).

Because the differential dropout rate during the FMD treatment period (25% in FMD in the randomized arm 2 and/or after arm 1 cross-over vs. 10% in the randomized arm 1 control) may have induced biases in estimates of the FMD treatment effect, we compared the changes in trial outcomes between the two groups who completed 3 FMD cycles (N=39 FMD randomized arm 2, N=32 after arm 1 crossover to FMD) using sensitivity-analysis. 3 FMD cycles had comparable effects between subjects in arm 1 (after cross over) and arm 2 (randomized) with the exception of HDL, which underwent a greater reduction in arm 2 (p=0.03) and the decrease in absolute lean body mass, which was observed in arm 2 but not arm 1 (Table 6 (FIG. 13)).

Because the FMD had similar effects in both arms, we combined the results from the two arms to assess the changes in metabolites and risk factors during the first FMD cycle (at day 5 of the FMD and before re-feeding, Table 7 (FIG. 14) and after completion of 3 FMD cycles (5-7 days after terminating the third FMD cycle, Table 6 (FIG. 13)).).

At the end of the first FMD cycle and before resuming the normal diet, body weight (p<0.0001), BMI (p<0.0001), absolute lean body mass (p<0.0001), waist circumference (p<0.0001), fasting glucose (p<0.0001), IGF-1 (p<0.0001), diastolic blood pressure (p<0.0003), triglycerides (p<0.0001), and LDL (p<0.0026) were significantly reduced compared to baseline. In contrast, relative lean body mass (p=0.02), β-hydroxybutyrate (p<0.0001) and IGFBP-1 (p<0.0001) were increased. Both absolute and relative total body fat (p=0.075 and p=0.047, respectively), systolic blood pressure (p=0.076), as well as CRP (p=0.75) were not significantly changed after completion of the first FMD cycle compared to baseline (Table 7 (FIG. 14)). These results confirm that subjects did follow the dietary changes imposed by the FMD and responded to them as anticipated.

In subjects who completed 3 FMD cycles (combining both FMD arms) and who returned to the normal diet for 5-7 days, body weight (p<0.0001, N=71), BMI (p<0.0001, N=71), total body fat (absolute and relative p<0.0001, respectively, N=70), trunk fat (absolute p<0.001, relative p=0.0002, N=70), absolute lean body mass (p=0.0001, N=70), waist circumference (p<0.0001, N=52), IGF-1 (p<0.0001, N=69), systolic and diastolic blood pressure (p<0.0001 and p<0.0004, respectively, N=70), total cholesterol (p=0.004, N=55), LDL (p<0.0011, N=55) and HDL (p=0.02, N=55) were significantly reduced and relative lean body mass (p=0.0002, N=70) was increased. Fasting glucose (p=0.28, N=66), β-hydroxybutyrate (p=0.23, N=69), IGFBP-1 (p=0.84, N=69), triglycerides (p=0.16, N=55) and CRP (p=0.052, N=69) were not significantly changed 5-7 days after the third FMD cycle compared to baseline (Table 6 (FIG. 13)). In summary, the combined FMD groups from arm 1 and arm 2 confirmed that the FMD cycles promoted potent effects on many metabolic markers and disease risk factors, which are maintained after subjects return to their normal diet.

FMD Effects Stratified by Baseline Risk Factor Values: A Post-Hoc Observational Pre-Post FMD Comparison.

Age-related physiological changes that lead to increased risk factors occur before diseases can be diagnosed (19, 20). We utilized the aggregated FMD data of both study arms and performed a post hoc analysis of the FMD effect on risk factors for cardiovascular disease and metabolic syndrome, defined as 3 out of 5 of the following conditions: abdominal obesity, elevated fasting glucose, elevated blood pressure, high serum triglycerides, and low HDL cholesterol (1). We selected clinically relevant cut-offs and compared normal and at-risk subjects for each risk factor: total cholesterol >199 mg/dL and LDL cholesterol levels >130 mg/dL are associated with an increased risk of cardiovascular disease (CVD) (21), fasting glucose >99 mg/dL indicates impaired fasting glucose/pre-diabetes (22), triglyceride levels >100 mg/dL (23) as well as CRP >1 mg/L are associated with increased risk for CVD (24). For serum IGF-1, no clinically relevant risk level has been established but a number of epidemiological studies have associated IGF-1 levels above 200 ng/ml with various cancers (17, 25). We therefore compared the effect of FMD cycles on subjects in the highest quartile of IGF-1 expression (>225 ng/ml) with that on subjects with IGF-1 levels ≤225 ng/ml.

In a post hoc analysis, we tested how the changes in the FMD normal and at-risk sub-groups compared to those in the control diet normal and at-risk sub-groups, as defined by their baseline levels of various risk factors (Table 3). We saw a significant benefit of the FMD, but not the control diet, on BMI in all BMI subgroups (p-value for interaction=0.03), although the FMD was particularly beneficial among subjects who were obese (BMI>30) at baseline. The FMD-dependent reduction in IGF-1 was also significantly larger in persons with baseline IGF-1 ≥225 ng/mL (p-value for interaction=0.018) and it was not observed in the two control diet groups.

Next, we evaluated the effect size, i.e. efficacy in normal and at-risk subjects (Table 4) in subjects stratified by risk factor. Subjects with a BMI over 30 (obese) experienced a greater reduction in BMI by the end of the 3 FMD cycles than subjects with a BMI less than 25 (between-group p=0.011), and 25 to 30 (between-group p=0.0011). Systolic blood pressure was reduced by 2.4±6.3 mmHg in subjects with baseline systolic blood pressure ≤120 but by 6.7±6.9 mmHg in subjects with systolic blood pressure >120 (between-group p=0.013), and diastolic blood pressure was reduced by 1.5±5.1 mmHg in subjects with diastolic blood pressure ≤80 but by 5.5±6.4 mmHg in those with baseline levels above 80 (between-group p=0.01). Fasting glucose did not change from baseline levels for participants with baseline levels ≤99 mg/dl but was reduced by 11.8±6.9 mg/dL in participants with baseline fasting glucose over 99 mg/dl (between-group p<0.0001); notably this reduction brought glucose in these subjects within the healthy range. IGF-1 levels in subjects with baseline levels above 225 ng/ml were reduced by 55.1±45.6 ng/mL, nearly 4 times more (between-group p<0.001) than the 14.1±39.9 ng/mL reduction observed in participants with IGF-1 concentrations below 225 ng/ml. Triglyceride levels were reduced more in participants with baseline levels >100 mg/dL (between-group p=0.0035). Total cholesterol was reduced significantly more in participants with total cholesterol higher than 199 mg/dL at baseline (between-group p=0.015). LDL was reduced by 14.9±21.7 mg/dL in those with total cholesterol baseline levels above 199 mg/dL but was not reduced by FMD cycles in normal-range subjects (between-group p=0.013). There was no reduction (between-group p=0.094) in HDL levels for those study participants with HDL levels below or above 50 mg/dl at baseline. CRP was not reduced for subjects with levels below 1 mg/L but was reduced by 1.6±1.3 mg/L and returned to the normal levels in most subjects with baseline CRP levels higher than 1 mg/L (between-group p=0.0003). A graphical summary of these data is presented in FIG. 3; before-after dot plots of individual subjects in the control cohort as well as in normal and at-risk subjects in the FMD cohort are presented in FIG. 6.

This post hoc analysis indicates that the FMD had more pronounced effects in at-risk participants than in those subjects who had risk factor values within the normal range, with the exception of HDL. Larger randomized trials are necessary to confirm the results on the efficacy of the FMD in the treatment of patients at risk for diseases.

Voluntary Follow-Up 3-Month after FMD.

We invited participants to return on a voluntary basis approximately 3 months (actual mean follow up time, 3.2±1.3 months; N=50) after their third and final FMD cycle. In these subjects, the FMD's effects on body weight, BMI, waist circumference, glucose (in at-risk subjects), IGF-1, systolic (in at-risk subjects) and diastolic blood pressure persisted for at least 3 months after the final FMD cycle (Table 8 (FIG. 15)).). Subjects with low HDL levels at baseline displayed increased HDL levels at the three months follow-up, while CRP levels remained significantly lower in study participants with baseline CRP levels above 1 mg/L.

Notably, some of the at-risk groups include only a few subjects, and thus larger studies are needed to establish long-term effects of the FMD on disease risk factors.

These results indicate that some of the beneficial effects of multiple cycles of the FMD may last for several months. Although subjects were not advised to change their nutrition or exercise regimen after the FMD cycles ended, we cannot rule out that some of the changes after the additional 3 months may be a result of lifestyle changes such as healthier diets and/or improved physical activity after the completion of this trial.

Discussion

This randomized phase 2 trial indicates that three cycles of a 5-day per month FMD are feasible, safe and effective in reducing body weight, waist circumference and BMI, absolute total body and trunk fat, systolic blood pressure, as well as IGF-1. Metabolic markers such as fasting glucose, triglycerides, CRP, as well as total-, HDL- and LDL-cholesterol, which were within the normal range at baseline, were not significantly affected in the randomized comparison after 3 FMD cycles. After 3 months, subjects from the control arm were crossed over to the FMD intervention. Our post hoc analysis of the aggregated data from all 71 subjects that completed 3 FMD cycles confirmed the effects of the FMD on trunk and total body fat, blood pressure, and IGF-1. A post hoc analysis also allowed us to analyze subjects with elevated risk factors or metabolic markers associated with metabolic syndrome and age-related diseases, such as high BMI, blood pressure, fasting glucose, triglycerides, CRP, cholesterol and IGF-1. The FMD had more pronounced effects on all these markers in at-risk participants than in those subjects who had risk factor values within the normal range, with the exception of HDL. Some of these metabolic markers, namely CRP, systolic/diastolic blood pressure, and serum lipids, have been proposed as markers of biological aging (26). However, other markers affected by the FMD, including IGF-1 and glucose have been strongly implicated in aging and age-related diseases (5, 18, 27).

Study participants were instructed not to alter their lifestyle for the duration of the trial and were allowed to consume food of their choice during the normal diet periods, i.e. subjects were not placed on a pre-specified or calorie-restricted diet. We observed changes that were both positive (total cholesterol and LDL) and negative (HDL) in arm 1 subjects during the control diet period, potentially explained by dietary habit changes in preparation for the FMD, despite no change in weight, BMI, body fat, or lean mass. Similarly, the persistent effects of the FMD three months after study completion that we observed may result from changes in dietary habits and/or physical activity. The composition of the diet tested in this trial was based on the FMD that is known to extend healthspan in mice. Similarly to the study in mice (5), we expect the FMD effects to be mostly independent of an overall caloric restriction, since both groups likely consumed similar levels of calories per month: e.g. estimating a 2000 kilocalorie diet for each of the 25-26 non-restricted days and about 4000 kilocalories for the 5 days of FMD per month, the between group difference in consumed calories is expected to be approximately 10%. In addition, this difference may be overestimated, because it is likely that subjects have an elevated calorie intake after the FMD period, as we have shown for mice (5).) Day 1 of the FMD supplies 4600 kJ (11% protein, 46% fat, 43% carbohydrate), whereas days 2-5 provide 3000 kJ per day (9% protein, 44% fat, 47% carbohydrate); thus fat and complex carbohydrates are the major source of calories in the FMD.

Our studies in cells and mice indicate that both glucose and proteins will interfere with the protective and regenerative effects of fasting (28). Because our previous data indicate that dietary composition can be equally or more important than calorie restriction, it will be important to test the effects of a similarly restricted diet that provides higher proportions of carbohydrates and/or proteins. It remains to be established whether part of the effects of FMD that we observed are mediated by stem cell-based regeneration or rejuvenation, as indicated by our mouse studies (5).

The FMD-induced reduction in serum glucose and IGF-1 is of interest given their role in pro-aging signaling pathways and cancer (17, 29-32). In addition to a marker for insulin resistance and a metabolic input for cancer cells, glucose is associated with cellular sensitization to toxins and senescence (27, 33, 34). Growth hormone receptor deficiency, resulting in reduced IGF-1 levels, is associated with a major reduction in pro-aging signaling, cancer and diabetes in humans (18). The observed reduction in IGF-1 in our study, but not following 6 months of either intermittent energy restriction (IER) (35) or after 6 years of 20% CR (36), is probably related to the long-lasting effects of the low protein/amino acid content of the FMD (average 5 days FMD 11.5% vs. 21% IER or 24% long term CR). In fact, 28 vegans consuming a moderately protein-restricted (10%) diet for about 5 years had reduced IGF-1 levels compared to a group that consumed a chronic 20% calorie restricted diet (36). We also previously showed that IGF-1 levels were positively associated with protein consumption in 2,253 participants of the NHANES cohort (17). Specific ingredients, e.g. high levels of unsaturated fats and micronutrients, may also positively contribute to some of the beneficial effects of the FMD.

It is of note that 25% of the subjects that tested the FMD dropped out of the trial, whereas 10% of the participants opted out of the control arm. This indicates that, despite our efforts to reduce the burden of low calorie/protein diets, adherence to this dietary regimen requires committed study participants. Further, compared to the control diet arm, the FMD arm imposed an additional day-long visit to the clinic, which may have contributed to reduced compliance. Compliance with prescribed therapies, even placebo, may be an identifiable marker for an overall healthy behavior of study participants (37). Thus, this kind of volunteer, who is seeing a benefit and thus not dropping out, could introduce potential bias into the analysis of our trial. The overall comparability at baseline between the control and both FMD arms, as well as the comparable response to the FMD (arm 2 and arm 1 after cross over) suggests no major differences in response for those subjects that completed the trial. Further, those subjects who dropped out of this trial were not different in age or BMI compared to those who completed the trial. It remains to be established why we experienced a gender difference (82% of dropouts were female). The 25% overall dropout rate (all causes) of study participants before the completion of the 3$^{rd}$ FMD cycle is in the range observed in other trials aimed at evaluating dietary interventions in adults. For example, 16 weeks of dieting in combination with physical exercise yielded a discontinuation rate of approximately 30% (38) and a hypocaloric diet in 28 overweight/obese women resulted in a dropout rate of 40% after 6 months (39). In a trial assessing the effect of intermittent energy/carbohydrate restriction and daily energy restriction on weight loss and metabolic disease risk markers in overweight women, Harvie et al. reported a 23% dropout rate (40). Nonetheless, there are limitations of our trial that should be considered: 1) the relatively small number of subjects in the randomized comparison; 2) despite providing nourishment and calories for the duration of the FMD, we experienced a higher dropout rate during the FMD intervention than in the control arm; 3) the findings that the FMD reduced metabolic markers more effectively in at-risk subjects is based on a non-randomized post hoc analysis of the individual factors in generally healthy participants and thus it needs further evaluation in subjects with diagnosed disease.

Other, less-restrictive diets such as those requiring a very low calorie intake twice a week would impose 8 days per month of a severe restriction compared to the 5 days per month or per several months of a less restrictive intervention tested here (40). Yet an advantage of these diets is that they may not require as much medical supervision as the longer FMD. FMDs or any type of prolonged fasting interventions lasting more than 12 hours, particularly those lasting several days, require supervision, preferably from a healthcare professional familiar with prolonged fasting. Although our results suggest that cycles of the plant-based FMD might be safe for elderly individuals, additional studies are necessary to determine its safety for subjects that are 70 and older.

In summary, and with the limitations outlined above, these results indicate that the periodic FMD cycles are effective in improving the levels of an array of metabolic markers/risk factors associated with poor health and aging and with multiple age-related diseases. As suggested by pre-clinical studies, interventions that promote longevity should also extend healthspan. Further investigations in larger clinical trials focused on subjects with diagnosed metabolic syndrome, diabetes, and cardiovascular diseases as well as subjects at high risk for developing cancer and other age-related diseases are needed.

Methods

Subjects 100 participants without a diagnosed medical condition in the preceding six months were enrolled (clinicaltrials.gov NCT02158897). All participants provided written informed consent and the University of Southern California Institutional Review Board (IRB) approved the protocol. Recruitment of subjects was based on fliers, the clinicaltrials.gov and usc.com websites, and/or word-of-mouth. Because this was a dietary intervention study, it was not possible for participants or all study personnel to be blinded to group assignment. However, study personnel involved in data collection and specimen analysis were blinded to group assignments.

Study Design

Flow of participant enrollment and participation was prepared following the CONSORT standards for randomized clinical trials with crossover design. All data were collected at the USC Diabetes & Obesity Research Institute. Subjects were recruited from April 2013 until July 2015 under protocols approved by the USC IRB (HS-12-00391), based on established inclusion (generally healthy adult volunteers, 18-70 years of age, body mass index: 18.5 and up) and exclusion (any major medical condition or chronic diseases, mental illness, drug dependency, hormone replacement therapy [DHEA, estrogen, thyroid, testosterone], pregnant or nursing female, special dietary requirements or food allergies, alcohol dependency, medications known to affect body weight) criteria. Intention to treat analysis was performed by including all available observations. Eligible participants were randomly assigned, using a random-number generator, to either arm 1 or arm 2 of the study. All participants completed a health habits questionnaire. Pre-specified outcome measures included safety and feasibility, and evaluation of changes in metabolic risk factors for diabetes and cardiovascular disease and metabolic markers associated with age-related diseases and mortality; these outcomes were measured at baseline, during and after completion of the intervention. Lab examinations included height, weight, body composition (including total and trunk body fat, soft lean tissue, and bone mineral content) measured by dual energy x-ray absorptiometry (DEXA), oscillometric blood pressure measurements and over-night fasting blood draw through venipuncture.

Arm 1 (Control): Participants completed anthropometric measurements and blood collection at enrollment and after 3 months to provide an estimate of non-diet related changes (FIG. 1). Participants were instructed to maintain their regular eating habits. After 3 months, subjects were crossed over to the experimental fasting mimicking diet (FMD) group (FIG. 1).

Arm 2 (Fasting mimicking diet): Participants were instructed to consume the FMD, which was provided in a box, for 5 continuous days, and to return to their normal diet after completion until the next cycle that was initiated approximately 25 days later. Participants completed 3 cycles of this 5-day FMD (FIG. 1). Participants completed baseline and follow-up examinations at the end of the $1^{st}$ FMD (before resuming normal diet to measure the acute FMD effects) and after a wash out period of 5-7 days of normal caloric intake following the $3^{rd}$ FMD cycle. An optional follow-up assessment 3 months after the third FMD cycle was offered.

Experimental Fasting Mimicking Diet

The fasting mimicking diet is a plant-based diet designed to attain fasting-like effects on the serum levels of IGF-1, IGFBP1, glucose and ketone bodies while providing both macro- and micronutrients to minimize the burden of fasting and adverse effects (5). Day 1 of the FMD supplies 4600 kJ (11% protein, 46% fat, 43% carbohydrate), whereas days 2-5 provide 3000 kJ (9% protein, 44% fat, 47% carbohydrate) per day. The FMD comprises proprietary formulations of vegetable-based soups, energy bars, energy drinks, chip snacks, tea, and a supplement providing high levels of minerals, vitamins and essential fatty acids (FIG. 7). All items to be consumed per day were individually boxed to allow the subjects to choose when to eat while avoiding accidentally consuming components of the following day.

Common Terminology Criteria for Adverse Events

Study participants were asked about adverse events at each study visit; events were graded according to the general CTCAE guidelines. See supplementary material for details.

Blood Tests and Serum Markers

Complete metabolic and lipid panels (over-night fasting) were completed at the Clinical Laboratories at the Keck Medical Center of USC and analyzed immediately following the blood draw of each visit. See supplementary material for details.

Statistical Analysis

The primary comparisons of randomized groups involved changes in outcomes observed in the control period of arm 1 vs. the changes observed in the FMD group (arm 2) after completion of 3 FMD cycles. Secondary observational analyses involved (1) comparing the FMD effects in arm 2 (randomized to FMD) vs. arm 1 (receiving FMD after completion of the randomized control period), and (2) summarizing the changes for arms 1 and arm 2 combined after completion of the $1^{st}$ and $3^{rd}$ FMD cycles. Changes from baseline were normally distributed. Comparison of changes from baseline within the treatment arms was performed using paired two-tailed Student's t-tests and p-values <0.05 were considered significant. The between-arm comparison of treatment changes from baseline was performed using two-tailed two-sample equal variance t-tests and p-values <0.05 were considered significant. To control for multiple testing, the Benjamini-Hochberg false discovery rate (FDR) method was used. All reported p-values are nominal two-sided p-values; those that met the FDR criteria and remained "significant" at p<0.05 are indicated with an asterisk.

MW generated the random allocation sequence, enrolled and assigned participants to interventions. MW was not involved in outcome assessments. For this initial randomized trial, the sample size of 100 total subjects was based on detection of a 25% reduction in mean IGF-1, with a two-sided alpha of 0.05 and 70% power. The estimated control group mean (SD) IGF-1 of 194 (97) used published data on males and females, aged 26-40 (41). Statistical analyses were performed on de-identified data. Baseline information and changes from baseline were summarized using mean±standard deviations for subjects randomized to the control (arm 1, N=48) and the diet group (arm 2, N=52). All subjects are included in the arm assigned regardless of treatment adherence (intention to treat); no attempt was made to impute missing values (primarily because if data after completion of the $3^{rd}$ FMD cycle was not available, other measurement time points were usually unavailable).

In post-hoc subgroup analyses, we compared FMD-control group differences over the randomized trial period (3 FMD cycles vs. control) within high/lower risk subgroups and tested if those treatment effects differed in the higher vs lower risk groups. This subgroup analysis was completed using analysis of variance, with main effects of treatment (FMD, control) and risk group (high, low); the interaction of treatment-by-risk group tested if the randomized FMD effect differed in high vs. low risk groups. In observational analyses of the pre-post FMD changes combining the two treatment arms, pre-post changes in markers within risk subgroups were tested using paired t-test; pre-post changes over risk subgroups were compared using two-sample t-test or analysis of variance.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. K. G. Alberti et al., Harmonizing the metabolic syndrome: a joint interim statement of the International Diabetes Federation Task Force on Epidemiology and Prevention; National Heart, Lung, and Blood Institute; American Heart Association; World Heart Federation; International Atherosclerosis Society; and International Association for the Study of Obesity. *Circulation* 120, 1640 (Oct. 20, 2009).
2. E. S. Ford, W. H. Giles, W. H. Dietz, Prevalence of the metabolic syndrome among US adults: findings from the third National Health and Nutrition Examination Survey. *Jama* 287, 356 (Jan. 16, 2002).
3. A. S. Gami et al., Metabolic syndrome and risk of incident cardiovascular events and death: a systematic review and meta-analysis of longitudinal studies. *Journal of the American College of Cardiology* 49, 403 (Jan. 30, 2007).

4. I. Y. Choi et al., A Diet Mimicking Fasting Promotes Regeneration and Reduces Autoimmunity and Multiple Sclerosis Symptoms. *Cell reports* 15, 2136 (Jun. 7, 2016).

5. S. Brandhorst et al., A Periodic Diet that Mimics Fasting Promotes Multi-System Regeneration, Enhanced Cognitive Performance, and Healthspan. *Cell metabolism* 22, 86 (Jul. 7, 2015).

6. V. D. Longo, S. Panda, Fasting, Circadian Rhythms, and Time-Restricted Feeding in Healthy Lifespan. *Cell metabolism* 23, 1048 (Jun. 14, 2016).

7. A. J. Bruce-Keller, G. Umberger, R. McFall, M. P. Mattson, Food restriction reduces brain damage and improves behavioral outcome following excitotoxic and metabolic insults. *Ann Neurol* 45, 8 (January, 1999).

8. A. L. Hartman, J. E. Rubenstein, E. H. Kossoff, Intermittent fasting: a "new" historical strategy for controlling seizures? *Epilepsy research* 104, 275 (May, 2013).

9. H. Muller, F. W. de Toledo, K. L. Resch, Fasting followed by vegetarian diet in patients with rheumatoid arthritis: a systematic review. *Scandinavian journal of rheumatology* 30, 1 (2001).

10. V. D. Longo, M. P. Mattson, Fasting: Molecular Mechanisms and Clinical Applications. *Cell metabolism* 19, 181 (Feb. 4, 2014).

11. C.-W. Cheng et al., Prolonged Fasting Reduces IGF-1/PKA to Promote Hematopoietic-Stem-Cell-Based Regeneration and Reverse Immunosuppression. *Cell Stem Cell* 14, 810 (Jun. 5, 2014).

12. W. E. Sonntag et al., Pleiotropic effects of growth hormone and insulin-like growth factor (IGF)-1 on biological aging: inferences from moderate caloric-restricted animals. *The journals of gerontology. Series A, Biological sciences and medical sciences* 54, B521 (December, 1999).

13. Y. Ikeno, R. T. Bronson, G. B. Hubbard, S. Lee, A. Bartke, Delayed occurrence of fatal neoplastic diseases in ames dwarf mice: correlation to extended longevity. *The journals of gerontology. Series A, Biological sciences and medical sciences* 58, 291 (April, 2003).

14. K. Flurkey, J. Papaconstantinou, R. A. Miller, D. E. Harrison, Lifespan extension and delayed immune and collagen aging in mutant mice with defects in growth hormone production. *Proceedings of the National Academy of Sciences of the United States of America* 98, 6736 (Jun. 5, 2001).

15. S. E. Dunn et al., Dietary restriction reduces insulin-like growth factor I levels, which modulates apoptosis, cell proliferation, and tumor progression in p53-deficient mice. *Cancer research* 57, 4667 (Nov. 1, 1997).

16. M. S. Bonkowski et al., Disruption of growth hormone receptor prevents calorie restriction from improving insulin action and longevity. *PloS one* 4, e4567 (2009).

17. M. E. Levine et al., Low protein intake is associated with a major reduction in IGF-1, cancer, and overall mortality in the 65 and younger but not older population. *Cell metabolism* 19, 407 (Mar. 4, 2014).

18. J. Guevara-Aguirre et al., Growth hormone receptor deficiency is associated with a major reduction in pro-aging signaling, cancer, and diabetes in humans. *Sci Transl Med* 3, 70ra13 (Feb. 16, 2011).

19. M. W. Gillman, Developmental origins of health and disease. *The New England journal of medicine* 353, 1848 (Oct. 27, 2005).

20. L. Fontana, B. K. Kennedy, V. D. Longo, D. Seals, S. Melov, Medical research: treat ageing. *Nature* 511, 405 (Jul. 24, 2014).

21. M. Nayor, R. S. Vasan, Recent Update to the US Cholesterol Treatment Guidelines: A Comparison With International Guidelines. *Circulation* 133, 1795 (May 3, 2016).

22. Diagnosis and classification of diabetes mellitus. *Diabetes care* 37 Suppl 1, S81 (January, 2014).

23. M. Miller et al., Triglycerides and cardiovascular disease: a scientific statement from the American Heart Association. *Circulation* 123, 2292 (May 24, 2011).

24. T. A. Pearson et al., Markers of inflammation and cardiovascular disease: application to clinical and public health practice: A statement for healthcare professionals from the Centers for Disease Control and Prevention and the American Heart Association. *Circulation* 107, 499 (Jan. 28, 2003).

25. M. N. Pollack, Insulin, insulin-like growth factors, insulin resistance, and neoplasia. *The American journal of clinical nutrition* 86, s820 (September, 2007).

26. M. E. Levine, Modeling the rate of senescence: can estimated biological age predict mortality more accurately than chronological age? *The journals of gerontology. Series A, Biological sciences and medical sciences* 68, 667 (June, 2013).

27. L. Fontana, L. Partridge, V. D. Longo, Extending healthy life span—from yeast to humans. *Science* 328, 321 (Apr. 16, 2010).

28. S. Brandhorst, M. Wei, S. Hwang, T. E. Morgan, V. D. Longo, Short-term calorie and protein restriction provide partial protection from chemotoxicity but do not delay glioma progression. *Experimental gerontology*, (Feb. 21, 2013).

29. A. G. Renehan et al., Insulin-like growth factor (IGF)-I, IGF binding protein-3, and cancer risk: systematic review and meta-regression analysis. *Lancet* 363, 1346 (Apr. 24, 2004).

30. J. M. Chan et al., Insulin-like growth factor-I (IGF-I) and IGF binding protein-3 as predictors of advanced-stage prostate cancer. *Journal of the National Cancer Institute* 94, 1099 (Jul. 17, 2002).

31. N. E. Allen et al., A prospective study of serum insulin-like growth factor-I (IGF-I), IGF-II, IGF-binding protein-3 and breast cancer risk. *British journal of cancer* 92, 1283 (Apr. 11, 2005).

32. O. Fletcher et al., Polymorphisms and circulating levels in the insulin-like growth factor system and risk of breast cancer: a systematic review. *Cancer epidemiology, biomarkers & prevention: a publication of the American Association for Cancer Research, cosponsored by the American Society of Preventive Oncology* 14, 2 (January, 2005).

33. K. Rapp et al., Fasting blood glucose and cancer risk in a cohort of more than 140,000 adults in Austria. *Diabetologia* 49, 945 (May, 2006).

34. T. Stocks et al., Blood glucose and risk of incident and fatal cancer in the metabolic syndrome and cancer project (me-can): analysis of six prospective cohorts. *PLoS Med* 6, e1000201 (December, 2009).

35. M. N. Harvie et al., The effects of intermittent or continuous energy restriction on weight loss and metabolic disease risk markers: a randomized trial in young overweight women. *International journal of obesity* 35, 714 (May, 2011).

36. L. Fontana, E. P. Weiss, D. T. Villareal, S. Klein, J. O. Holloszy, Long-term effects of calorie or protein restriction on serum IGF-1 and IGFBP-3 concentration in humans. *Aging cell* 7, 681 (October, 2008).

37. R. D. Hays et al., The impact of patient adherence on health outcomes for patients with chronic disease in the Medical Outcomes Study. *Journal of behavioral medicine* 17, 347 (August, 1994).

38. T. P. Wycherley et al., A high-protein diet with resistance exercise training improves weight loss and body composition in overweight and obese patients with type 2 diabetes. *Diabetes care* 33, 969 (May, 2010).

39. D. Florakis et al., Effect of hypocaloric diet plus sibutramine treatment on hormonal and metabolic features in overweight and obese women with polycystic ovary syndrome: a randomized, 24-week study. *International journal of obesity* 32, 692 (April, 2008).

40. M. Harvie et al., The effect of intermittent energy and carbohydrate restriction v. daily energy restriction on weight loss and metabolic disease risk markers in overweight women. *The British journal of nutrition* 110, 1534 (October, 2013).

41. G. Brabant et al., Serum insulin-like growth factor I reference values for an automated chemiluminescence immunoassay system: results from a multicenter study. *Hormone research* 60, 53 (2003).

42. www.census.gov

What is claimed is:

1. A method for mimicking effects of fasting, the method comprising:

administering to a subject as the only source of calories for five consecutive days, a plant-based fasting-mimicking diet provided from a fasting-mimicking diet package that includes at least a tomato soup composition and a mushroom soup composition, the fasting-mimicking diet providing the subject with a predetermined caloric intake of 700 kcal/day to 1100 kcal/day, the fasting mimicking diet package including daily meal portions that provide less than 40 grams of sugar for day 1, less than 30 grams of sugar for days 2 to 5, less than 28 grams of protein for day 1, less than 18 grams of protein for days 2 to 5, 20-30 grams of monounsaturated fats or more to reach the predetermined caloric intake for day 1, 6-10 grams of polyunsaturated fats or more to reach the predetermined caloric intake for day 1, 2-12 grams of saturated fats or more to reach the predetermined caloric intake for day 1, 10-15 grams of monounsaturated fats or more to reach the predetermined caloric intake for days 2 to 5, 3-5 grams of polyunsaturated fats or more to reach the predetermined caloric intake for days 2 to 5, 1-6 grams of saturated fats or more to reach the predetermined caloric intake for days 2 to 5, and a micronutrient composition on each day and any remaining days, wherein compositions of the fasting-mimicking diet package are portioned to attain fasting-like effects on serum levels of IGF-1, IGFBP-1, glucose and ketone bodies while providing both macronutrients and micronutrients to minimize the burden of fasting and adverse effects.

2. The method of claim 1 wherein the fasting-mimicking diet package provides daily meal portions for a predetermined number of days, the daily meal portions being packaged into meal servings or into a total daily serving to be divided into meals.

3. The method of claim 1 wherein the fasting-mimicking diet package further includes a quinoa-containing minestrone soup composition and a pumpkin soup composition.

4. The method of claim 3 wherein the fasting-mimicking diet package further includes:

a nut-containing nutrition bar;

a cocoa-containing nutrition bar;

a first olive-containing composition;

a kale cracker composition;

a vegetable soup composition;

a first vegetable broth composition;

a tea composition that includes spearmint;

an energy drink composition;

a micronutritional composition; and an algal oil composition.

5. The method of claim 4 wherein the fasting-mimicking diet package further includes:

a second olive-containing composition;

a second vegetable broth composition;

a bean-containing minestrone soup composition;

a tea composition that includes spearmint and lemon; and a tea composition that includes hibiscus.

6. The method of claim 5 wherein:

the nut-containing nutrition bar includes almond meal and macadamia nuts;

the cocoa-containing nutrition bar includes almond butter, almonds, and brown rice crispy;

the mushroom soup composition includes brown rice powder, carrots, inulin, and;

the bean-containing minestrone soup composition includes white beans, cabbage, and potatoes;

the first vegetable broth composition includes carrots, maltodextrin, celery, spinach, and tomatoes;

the second vegetable broth composition includes carrots, maltodextrin, celery, spinach, soy lecithin, and tomatoes;

the energy drink composition includes glycerin and water;

the algal oil composition includes schizocatrium algae oil;

the kale cracker composition includes almonds, kale, sesame seeds, and tapioca flour;

the tomato soup composition includes tomatoes, inulin, and onions;

the quinoa-containing minestrone soup composition includes quinoa, cabbage, potatoes, rice flour, and tomatoes;

the bean-containing minestrone soup composition includes white beans, cabbage, and potatoes;

the pumpkin soup composition includes pumpkin, rice flour, carrots, and brown rice powder; and the micronutrient composition includes beet root powder, calcium carbonate, carrots, collard leaf, kale leaf, and tomatoes.

7. The method of claim 6 wherein the micronutrient composition includes Vit A, Vit C, Ca, Fe, Vit D3, Vit E, Vit K, Vit B1, Vit B2, Vit B3, Vit B5, Vit B6, Vit B7, Vit B9, Vit B12, Cr, Cu, I, Mg, Mn, Mo, Se, and Zn.

8. The method of claim 5 wherein:

the nut-containing nutrition bar comprises almond meal in an amount of 20 to 35 weight %; coconut in an amount of 2 to 10 weight %; coconut oil in an amount of 1 to 8 weight %; flax seed meal in an amount of 1 to 8 weight %; honey in an amount of 10 to 30 weight %; macadamia nuts in an amount of 10 to 30 weight %; pecans in an amount of 10 to 25 weight %; salt in an amount of 0.1 to 0.8 weight %; and optionally vanilla in an amount of 0.3 to 1.5 weight %;

the cocoa-containing nutrition bar comprises almond butter in an amount of 10 to 25 weight %; almonds in an amount of 3 to 12 weight %; brown rice crispy in an amount of 10 to 25 weight %; brown rice syrup in an amount of 2 to 8 weight %; chocolate liquor in an amount of 1 to 4 weight %, cocoa butter in an amount of 0.4 to 1.6 weight %; cocoa powder in an amount of 4 to 12 weight %; fiber syrup SF75 in an amount of 18 to 38 weight %, flax seed oil in an amount of 1 to 3 weight %; salt in an amount of 0.1 to 0.4 weight % and sugar in an amount of 1 to 6 weight %;

the first olive-containing composition comprises lactic acid in an amount of 0.3 to 1 weight %; olive oil in an amount of 2 to 6 weight %; olives in an amount of 50 to 97 weight %; salt in an amount of 0.8 to 3 weight %; and thyme in an amount of 0.1 to 0.5 weight %;

the second olive-containing composition comprises garlic in an amount of 0.1 to 0.6 weight %; lactic acid in an amount of 0.3 to 1 weight %; olive oil in an amount of 2 to 6 weight %; olives in an amount of 50 to 97 weight %; salt in an amount of 0.8 to 3 weight %; and thyme in an amount of 0.1 to 0.5 weight %;

the kale cracker composition comprises almonds in an amount of 15 to 40 weight %; black pepper in an amount of 0.1 to 0.4 weight %; chia seeds in an amount of 3 to 10 weight %; chili pepper in an amount of 0.4 to 1.2 weight %; cumin seeds in an amount of 0.3 to 0.9 weight %; flax seeds in an amount of 3 to 10 weight %; garlic in an amount of 0.02 to 0.04 weight %; kale in an amount of 2 to 6 weight %; sunflower oil in an about of 2 to 7 weight %; onion in an amount of 0.3 to 0.9 weight %; oregano in an amount of 0.01 to 0.06 weight %; salt in an amount of 1 to 4 weight %; sesame seeds in an amount of 15 to 35 weight %; sugar in an amount of 1 to 5 weight %; tapioca flour in an amount of 10 to 30 weight %; vinegar in an amount of 1 to 4 weight %; water in an amount of 2 to 12 weight %; and yeast extract in an amount of 0.3 to 1 weight %;

the first vegetable broth composition includes carrots in an amount of 6 to 18 weight %; celery in an amount of 3 to 10 weight %; garlic in an amount of 3 to 10 weight %; maltodextrin in an amount of 8 to 25 weight %; canola oil in an amount of 0.5 to 2 weight %; onion in an amount of 6 to 18 weight %; parsley in an amount of 3 to 10 weight %; potato in an amount of 1 to 3 weight %; salt in an amount of 7 to 21 weight %; spinach in an amount of 3 to 10 weight %; tomatoes in an amount of 6 to 18 weight %; and yeast extract in an amount of 1 to 6 weight %;

the second vegetable broth composition includes carrots in an amount of 3 to 10 weight %; celery in an amount of 3 to 12 weight %; garlic in an amount of 3 to 9 weight %; maltodextrin in an amount of 8 to 25 weight %; canola oil, in an amount of 0.5 to 2 weight %; onion in an amount of 3 to 12 weight %; parsley in an amount of 3 to 10 weight %; potato in an amount of 1 to 6 weight %; salt in an amount of 8 to 25 weight %; soy lecithin in an amount of 0.5 to 3 weight %; spinach in an amount of 3 to 12 weight %; tomatoes in an amount of 6 to 18 weight %; xanthan gum in an amount of 0.5 to 4 weight %; and yeast extract in an amount of 4 to 12 weight %;

the vegetable soup composition comprises includes basil in an amount of 0.3 to 0.9 weight %; brown rice powder in an amount of 3 to 12 weight %; carrots in an amount of 4 to 14 weight %; green tea extract in an amount of 0.02 to 0.06 weight %; inulin in an amount of 5 to 15 weight %; leeks in an amount of 1 to 5 weight %; olive oil in an amount of 1 to 6 weight %; onion in an amount of 4 to 15 weight %; parsley in an amount of 0.3 to 0.8 weight %; red bell peppers in an amount of 1 to 5 weight %; rice flour in an amount of 18 to 50 weight %; salt in an amount of 2 to 7 weight %; spinach in an amount of 0.4 to 1.5 weight %; tomatoes in an amount of 4 to 14 weight %; yeast extract in an amount of 0.5 to 1.8 weight %;

the mushroom soup composition comprises brown rice powder in an amount of 10 to 30 weight %; carrots in an amount of 3 to 12 weight %; green tea extract in an amount of 0.02 to 0.06 weight %; inulin in an amount of 3 to 12 weight %; mushrooms in an amount of 6 to 18 weight %; olive oil in an amount of 1 to 6 weight %; onion in an amount of 3 to 12 weight %; parsley in an amount of 0.1 to 0.5 weight %; rice flour in an amount of 18 to 50 weight %; salt in an amount of 2 to 8 weight %; yeast extract in an amount of 0.5 to 1.5 weight %;

the tomato soup composition comprises basil in an amount of 0.2 to 0.7 weight %; brown rice powder in an amount of 1 to 5 weight %; green tea extract in an amount of 0.02 to 0.06 weight %; inulin in an amount of 7 to 20 weight %; olive oil in an amount of 3 to 9 weight %; onion in an amount of 4 to 12 weight %; parsley in an amount of 0.1 to 0.6 weight %; rice flour in an amount of 18 to 50 weight %; salt in an amount of 2 to 9 weight %; tomatoes in an amount of 12 to 36 weight %; and yeast extract in an amount of 0.5 to 3 weight %;

the quinoa-containing minestrone soup composition comprises includes basil in an amount of 0.7 to 2 weight %; broccoli powder in an amount of 0.6 to 2 weight %; cabbage white in an amount of 3 to 10 weight %; carrots in an amount of 3 to 10 weight %; celery in an amount of 1 to 4 weight %; celery seeds in an amount of 0.07 to 0.2 weight %; garlic in an amount of 0.7 to 2 weight %; green tea extract in an amount of 0.02 to 0.06 weight %; inulin in an amount of 1 to 5 weight %; leeks, in an amount of 0.7 to 2 weight %; olive oil in an amount of 0.6 to 2 weight %; onion in an amount of 2 to 8 weight %; peas in an amount of 3 to 10 weight %; potato in an amount of 7 to 20 weight %; *quinoa* in an amount of 7 to 20 weight %; rice flour in an amount of 7 to 20 weight %; salt, in an amount of 1 to 6 weight %; spinach in an amount of 0.5 to 2 weight %; tomatoes in an amount of 2 to 6 weight %; yeast extract in an amount of 0.6 to 2 weight %; and zucchini in an amount of 2 to 8 weight %;

the bean-containing minestrone soup composition comprises white beans in an amount of 3 to 10 weight %; cabbage white in an amount of 2 to 8 weight %; carrots in an amount of 2 to 8 weight %; celery in an amount of 1 to 4 weight %; green tea extract in an amount of 0.02 to 0.06 weight %; inulin in an amount of 2 to 10 weight %; leeks in an amount of 2 to 7 weight %; olive oil in an amount of 2 to 7 weight %; onion in an amount of 2 to 7 weight %; parsley in an amount of 0.2 to 1 weight %; peas in an amount of 3 to 9 weight %; potato in an amount of 15 to 45 weight %; rice flour in an amount of 6 to 18 weight %; salt in an amount of 2 to 8 weight %; spinach in an amount of 0.5 to 1.5 weight %; tomatoes in an amount of 2 to 7 weight %; and yeast extract in an amount of 0.5 to 1.5 weight %;

the pumpkin soup composition comprises brown rice powder in an amount of 3 to 9 weight %; carrots in an amount of 2 to 8 weight %; green tea extract in an amount of 0.02 to 0.06 weight %; inulin in an amount of 2 to 10 weight %; olive oil in an amount of 1 to 7 weight %; onion in an amount of 1.0 to 3 weight %;

pumpkin powder in an amount of 20 to 60 weight %; rice flour in an amount of 15 to 45 weight %; salt in an amount of 2 to 10 weight %; and yeast extract in an amount of 0.3 to 1 weight %;

the tea composition that includes spearmint includes spearmint leaves organic in an amount of 70 to 100 weight %;

the tea composition that includes lemon and spearmint includes lemon myrtle organic in an amount of 3 to 12 weight %; lemon peel organic in an amount of 10 to 25 weight %; spearmint leaves organic in an amount of 50 to 95 weight %;

the tea composition that includes hibiscus includes hibiscus tea leaves organic in an amount of 80 to 100 weight %;

the energy drink composition comprises glycerin in an amount of 20 to 60 weight %; water in an amount of 40 to 80 weight %;

the algal oil composition comprises schizocatrium algae oil in an amount of 80 to 100 weight %;

the micronutritional composition comprises ascorbic acid in an amount of 1 to 3 weight %; beet root powder in an amount of 6 to 20 weight %; beta carotene in an amount of 0.05 to 0.15 weight %; calcium carbonate in an amount of 6 to 20 weight %; carrots in an amount of 6 to 20 weight %; cholecaliciferol in an amount of 0.00 weight %; chromium Picolinate in an amount of 0.00 weight %; collard leaf powder in an amount of 6 to 20 weight %; cupric sulfate in an amount of 0.01 to 0.06 weight %; cyanocobalamin, 0.00; DI-alpha tocopherol acetate in an amount of 0.3 to 1 weight %; ferrous fumarate in an amount of 0.2 to 1 weight %; folic acid in an amount of 0.00 weight %; kale leaf in an amount of 6 to 20 weight %; magnesium stearate in an amount of 1 to 6 weight %; manganese sulfate in an amount of 0.04 to 0.08 weight %; niacinamide in an amount of 0.3 to 1 weight %; pantothenic acid in an amount of 0.1 to 0.6 weight %; phytonadione in an amount of 0.00 weight %; potassium iodine in an amount of 0 weight %; pyriodoxine HCl in an amount of 0.03 to 0.1 weight %; riboflavin in an amount of 0.02 to 0.1 weight %; sodium molybdate in an amount of 0.00 weight %; sodium selenate in an amount of 0.00 weight %; spinach in an amount of 6 to 20 weight %; thiamine mononitrate in an amount of 0.02 to 0.1 weight %; tomatoes in an amount of 6 to 20 weight %; tribasic calcium phosphate in an amount of 0.5 to 2 weight %; and zinc oxide in an amount of 0.2 to 0.8 weight %.

9. The method of claim 1 wherein the fasting-mimicking diet package is administered to a subject in need of inducement of differential effects on disease factors and markers associated with aging, the method comprises administering the fasting-mimicking diet to a subject in need thereof.

10. The method of claim 9 wherein the disease factors and marking are insulin-like growth factor-1, blood glucose, systolic blood pressure, diastolic blood pressure, cholesterol, CRP, triglycerides, or abdominal/visceral fats.

11. The method of claim 1 wherein the fasting-mimicking diet package is administered to a subject in need of promotion and inducement of beneficial long-lasting effects on disease factors and markers associated with aging.

12. The method of claim 11 wherein the disease factors and marking are insulin-like growth factor-1, blood glucose, systolic or diastolic blood pressure.

13. The method of claim 1 wherein the fasting-mimicking diet package is administered to a subject in need of promotion and inducement of stem-cell based regeneration of multiple organs and systems.

14. The method of claim 13 wherein the stem-cell based regeneration of multiple organs and systems includes neurogenesis, hematopoiesis, or promotion of pancreatic beta-cells.

* * * * *